United States Patent
Meyhack et al.

(12) 
(10) Patent No.: US 6,410,272 B1
(45) Date of Patent: Jun. 25, 2002

(54) PRODUCTION OF THROMBIN INHIBITORS

(75) Inventors: Bernd Meyhack, Magden; Walter Märki, Möhlin; Jutta Heim, Pratteln, all of (CH)

(73) Assignee: Ciba-Geigy Corporation a Corp. of New York, Ardsley, NY (US)

( * ) Notice: Subject to any disclaimer, the term of this patent is extended or adjusted under 35 U.S.C. 154(b) by 0 days.

(21) Appl. No.: 07/488,513

(22) Filed: Feb. 27, 1990

Related U.S. Application Data

(63) Continuation of application No. 06/938,102, filed on Dec. 4, 1986, now abandoned.

(30) Foreign Application Priority Data

Dec. 12, 1985 (GB) .............................................. 85 30631
May 29, 1986 (GB) .............................................. 86 13088

(51) Int. Cl.$^7$ ................................................ C12P 21/04
(52) U.S. Cl. ..................... 435/71.1; 435/69.1; 435/483; 435/212; 435/226; 435/254; 435/254.21; 435/320.1; 536/23.1; 536/23.5; 536/24.1
(58) Field of Search ...................... 435/69.1, 91, 172.1, 435/172.3, 255, 256, 911, 940, 71.1, 483, 212, 226, 254.11, 254.21, 320.1; 536/27, 23.1, 23.5, 24.1; 935/6, 8, 9, 10, 11, 22, 23, 24, 27, 28, 34, 36, 37, 47, 48, 59, 60, 61, 66, 69

(56) References Cited

U.S. PATENT DOCUMENTS

| | | | | |
|---|---|---|---|---|
| 4,588,684 A | * | 5/1986 | Brake et al. | |
| 4,742,003 A | * | 5/1988 | Derynck et al. | |
| 4,752,576 A | * | 6/1988 | Brake et al. | |
| 5,010,003 A | * | 4/1991 | Chang | |

FOREIGN PATENT DOCUMENTS

| | | |
|---|---|---|
| EP | 0088632 | 9/1983 |
| EP | 0100561 | 2/1984 |
| EP | 0123294 | 10/1984 |
| EP | 0138111 | 4/1985 |
| EP | 0143081 | 5/1985 |
| EP | 0158564 | 10/1985 |
| EP | 0158986 | 10/1985 |
| EP | 0168342 | 1/1986 |
| EP | 0171024 | 2/1986 |
| EP | 0173619 | 3/1986 |
| EP | 0200655 | 11/1986 |
| EP | 0213593 | 3/1987 |
| EP | 0252854 | 1/1988 |
| ZA | 84/9068 | 7/1985 |

OTHER PUBLICATIONS

Gene Expression in Yeast, Proceedings of the Alko Yeast Symposium, Helsinki, pp. 157–163 (1983).
Michael Bröker et al., Biochimica et Biophysica Acta 908 (pp. 203–213) 1987.
Anthony J. Brake et al., Proc. Natl. Acad. Sci. USA, 81, pp. 4642–4646 (1984).
Wajeeh Bajwa et al., Nucleic Acids Research, 12, #20 pp. 1721–7739 (1984).
Marion Bayne et al., Gene, 66, pp. 235–244.
Current Communications in Molecular Biology, Anthony Brake et al., pp. 103–109 (1985).
Luppo Edens et al., Cell, 37, pp. 629–633, Jun. (1984).
Joachim F. Ernst et al., Biotechnology, 5 pp. 831–834.
Yeast Genetics and Molecular Biology, Abstracts—Twelfth International Conference, 9/84, p. 143.
M. A. Innis et al., Science, 228, pp. 21–26 (1985).
Yoshifumi Jigami et al., 43, pp. 273–279, (1986).
David Julius, Cell, 36, pp. 309–318 (1984).
Susan M. Kingsman et al., Biochem. and Genetic Engineering Reviews, 3, pp. 377–416.
Jeffrey F. Lemontt, et al., DNA, 4, #6, pp. 419–428 (1985).
G. Loison et al., Biotechnology, 6, pp. 72–77, (1988).
J. Mellor, et al., Gene, 24, pp. 1–14 (1983).
Yeast Genetics and Molecular Biology—Twelfth International Conference—p. 138 (9/84).
Donald Moir et al., Gene, 56 pp. 209–217 (1987).
Robert A. Smith et al., Science, 229, pp. 1219–1224, (1985).
Karl Kristian Thomsen, Carlsberg Res. Commun., 48, pp. 545–555 (1983).
Scott Emr, Yeast Cell Biology, pp. 202–203, (1989) Aug.
Gunnar Von Heijne, Eur. J. Biochem. 133 pp. 17–21 (1983).
Gunnar Von Heijne, The EMBO Journal, 3, No. 10, pp. 2315–2318 (1984).
M. Gerard Waters et al., The Journal of Biological Chemistry, 263, No. 13, pp. 6209–6214 (1988).
Clive R. Wood et al., Nature, 314, pp. 446–449 (1985).
S. M. Kingsman et al., Biotechnol. Genet. Engin. Revs. 3, 377–416 (1985).
Edens et al 1984 Cell 37:629–633.*
Chemical Abstracts 102:42980a Vectors for Interferon Expression Kramer, Richard EPA 124,874 Nov. 14, 1984.*
Derwent Abstract 86–293155/45, EP–200,655A.
Derwent Abstract, 85–261387/42, WO 8504–418–A.

* cited by examiner

*Primary Examiner*—Remy Yucel

(57) ABSTRACT

A method for the production and secretion of proteins with hirudin activity in an eukaryotic host organism is provided. There are also provided hybrid vectors comprising a DNA sequence encoding a signal peptide upstream of and in reading frame with the structural gene for desulphatohirudin, and eukaryotic host organisms transformed with said hybrid vectors.

14 Claims, 15 Drawing Sheets

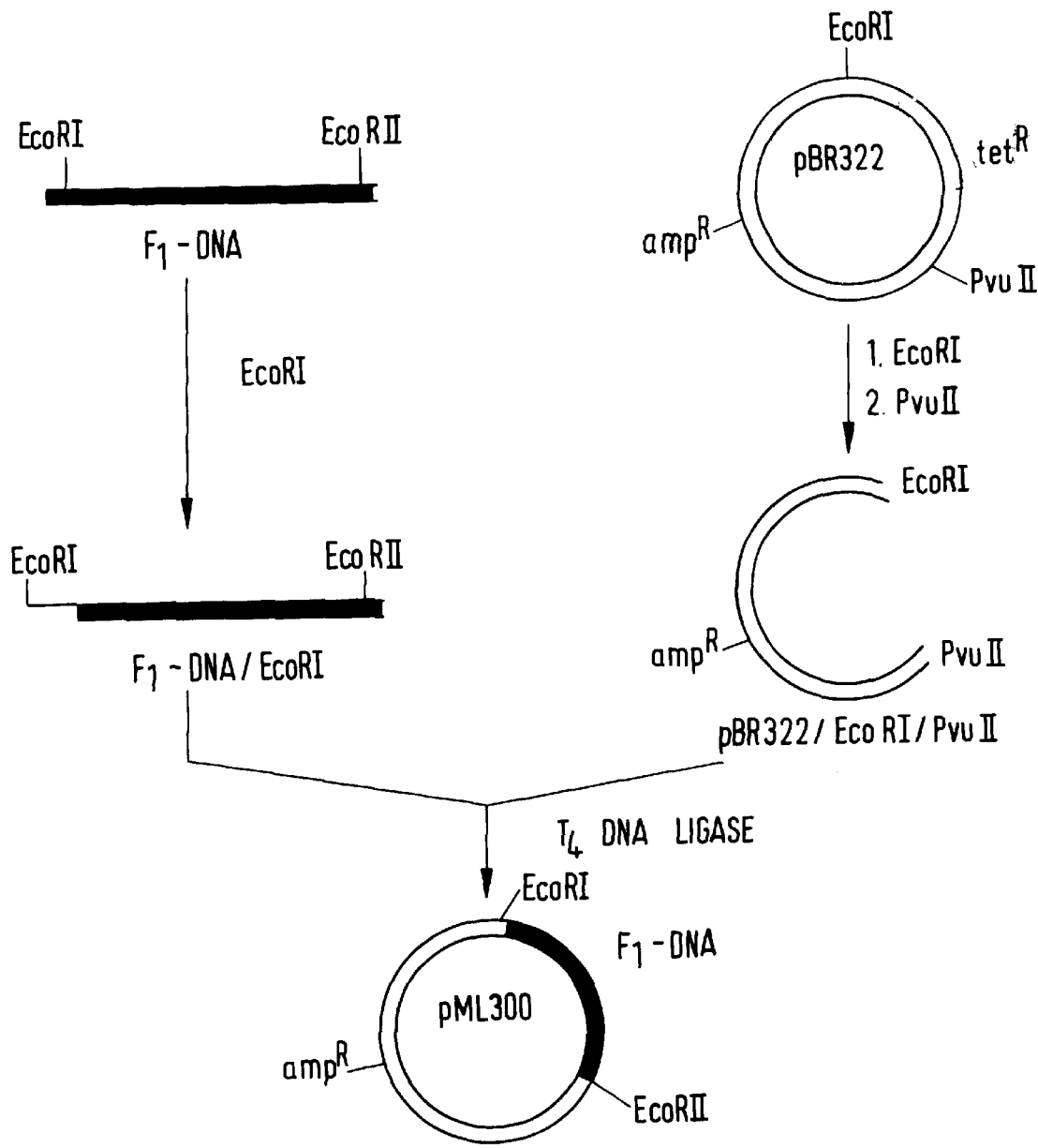
Fig. 1  CONSTRUCTION OF PLASMID pML300

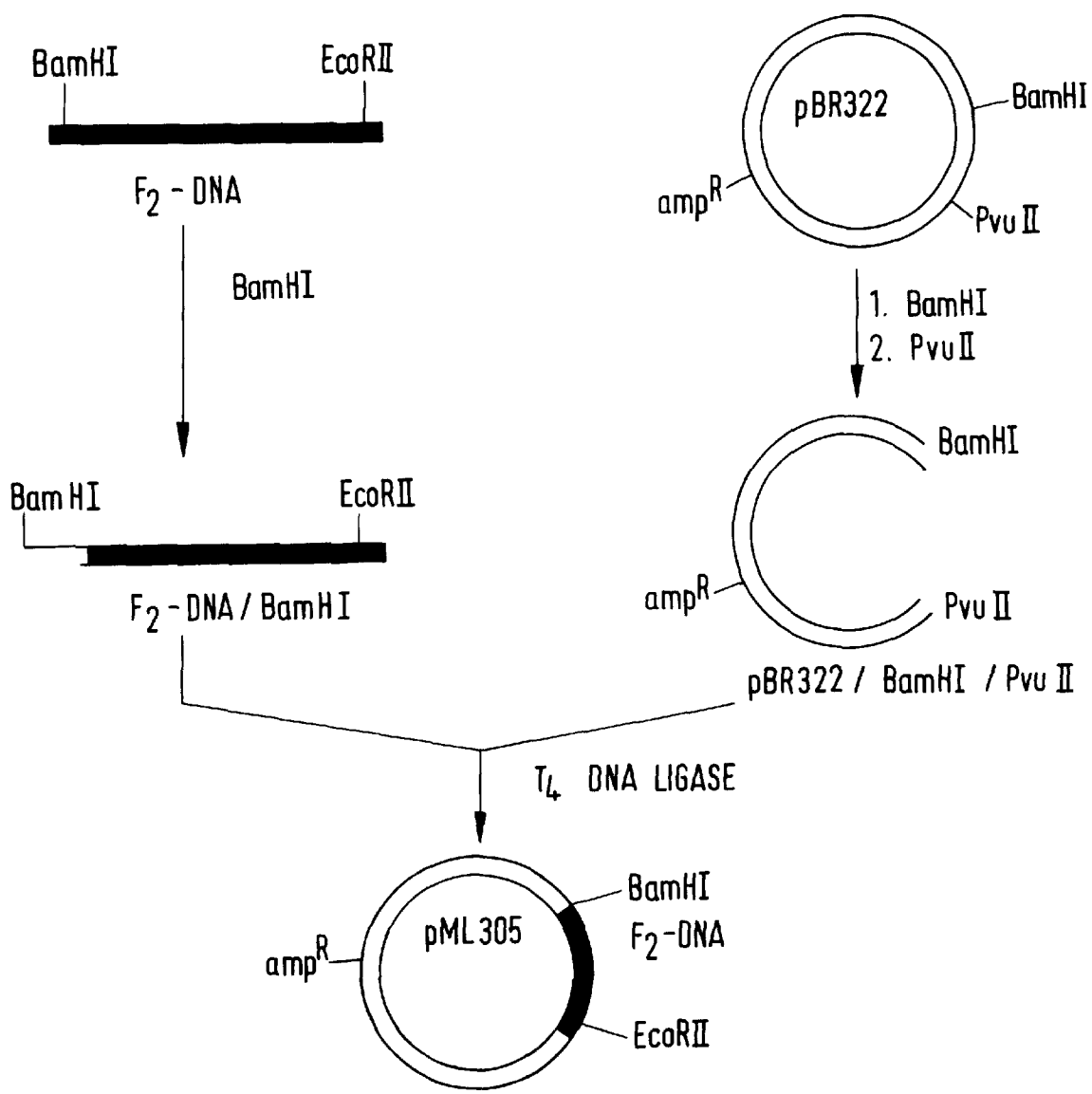
Fig. 2  CONSTRUCTION OF PLASMID pML305

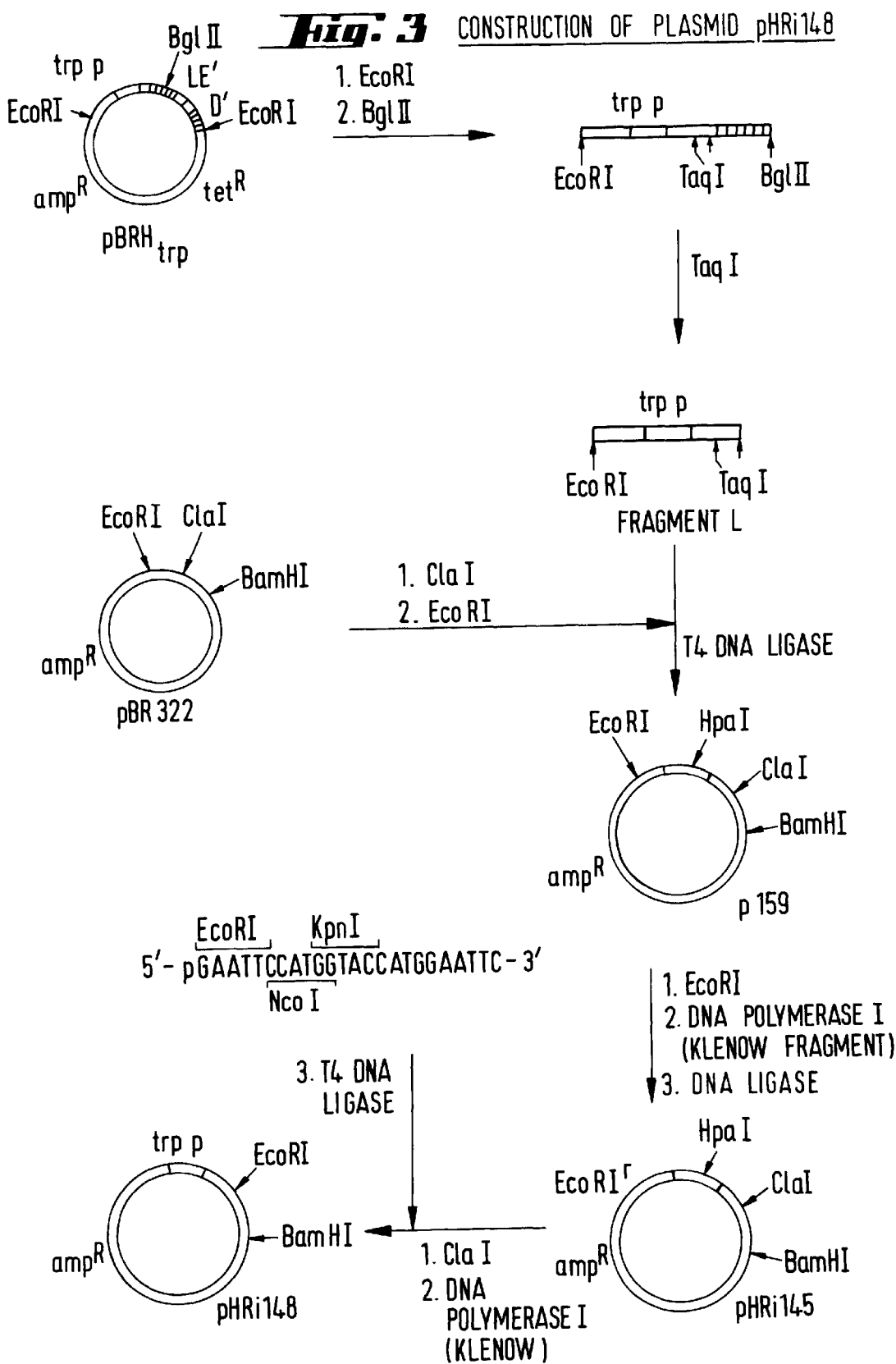

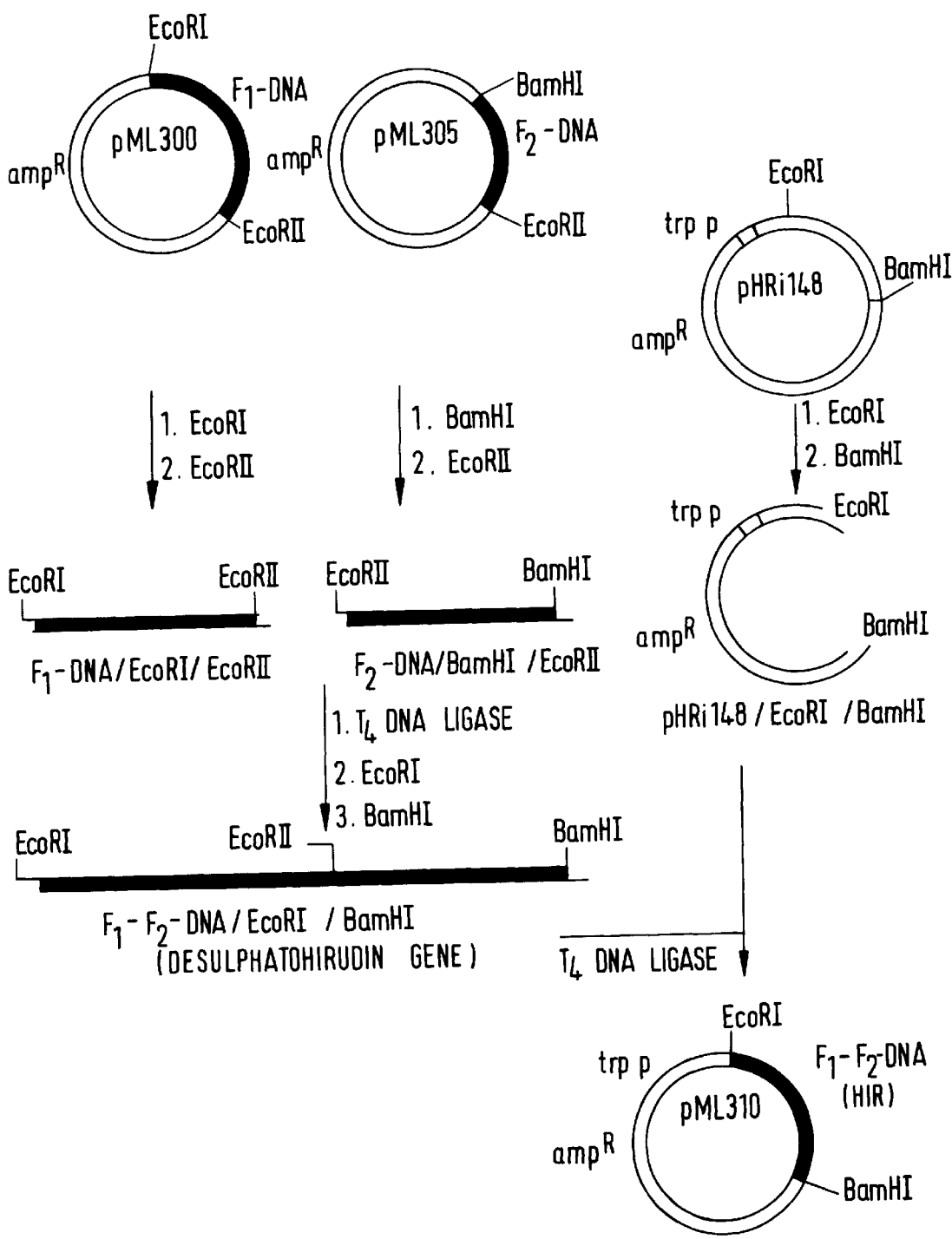
Fig. 4 CONSTRUCTION OF EXPRESSION PLASMID pML310

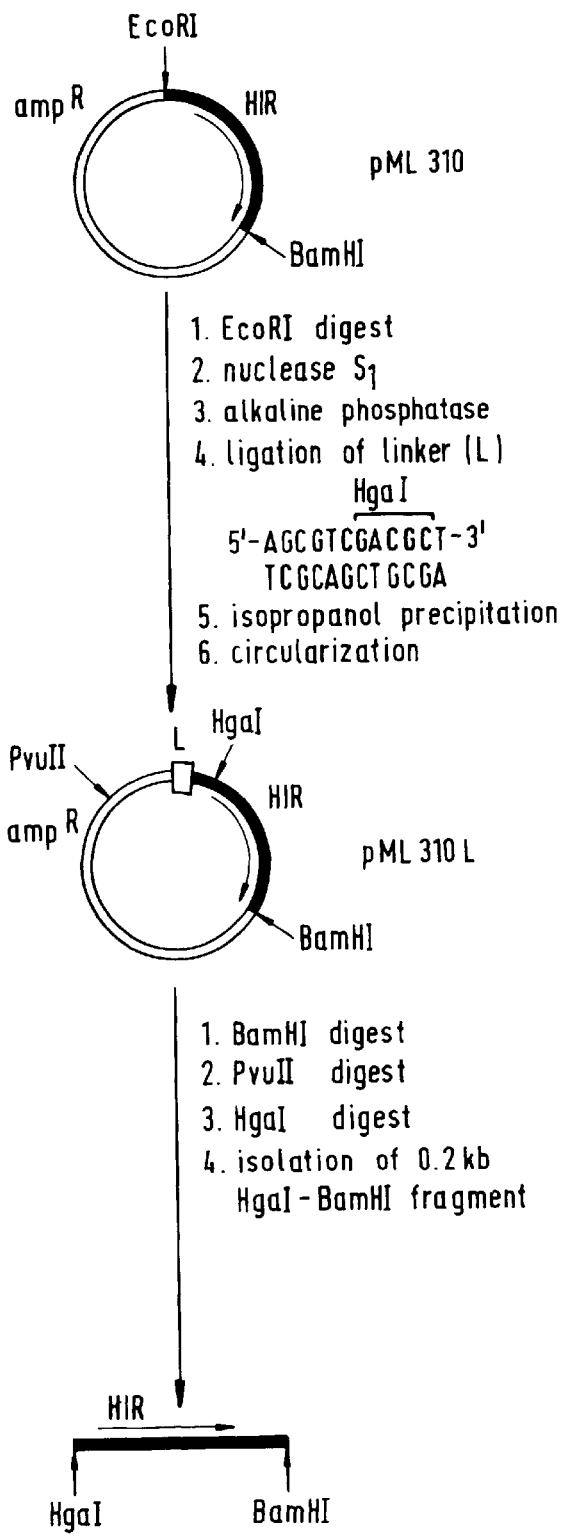
Fig. 5 ISOLATION OF A DNA FRAGMENT CODING FOR MATURE DESULPHATOHIRUDIN

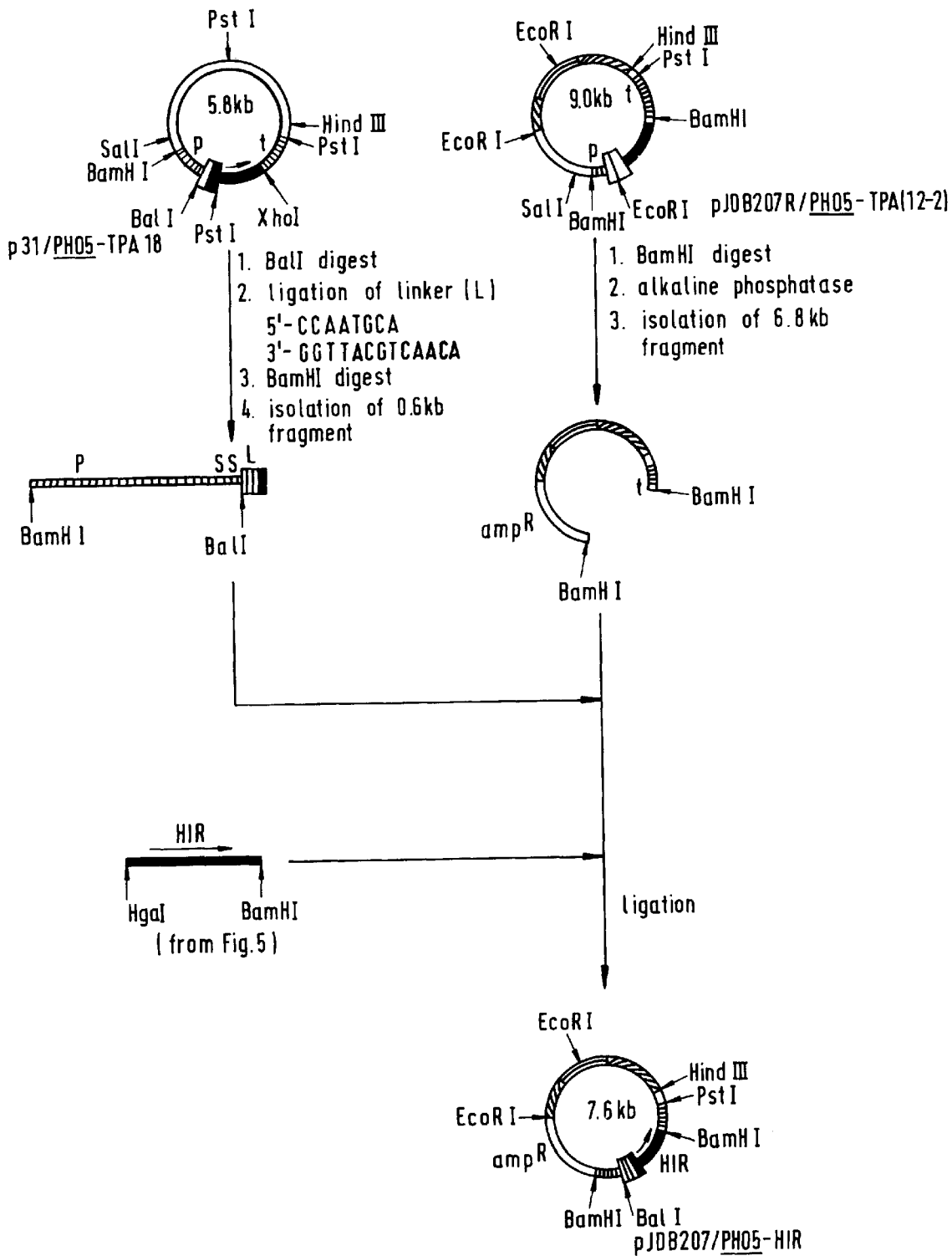

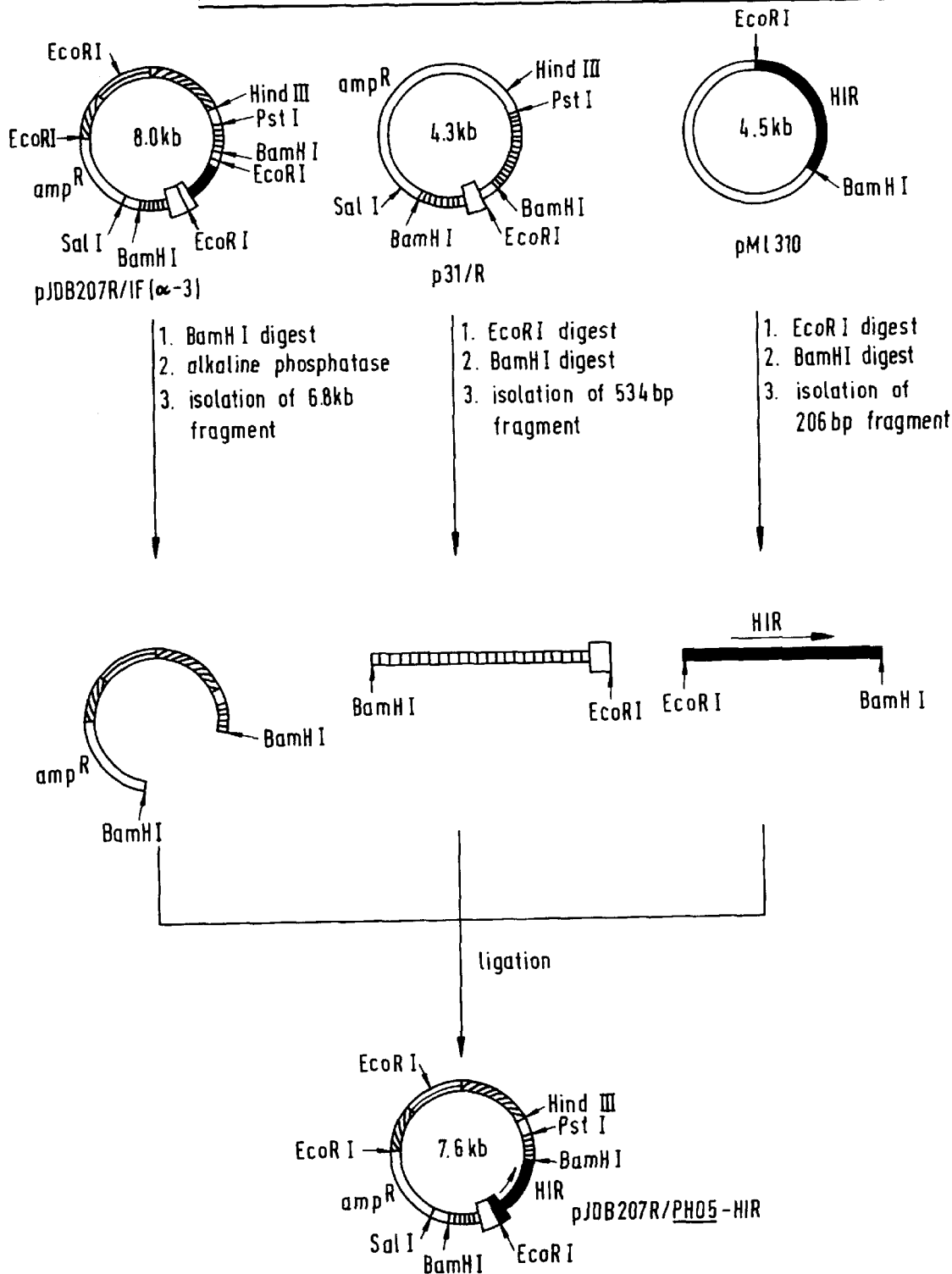

Fig. 8  DNA SEQUENCE OF THE BamHI-SalI RESTRICTION FRAGMENT OF PHO5 INCLUDING THE PHO5 PROMOTER REGION

```
                                                              BamHI
                                                                ↓
                                                               GG
    -540        -530       -520       -510       -500
    ATCCGAAAGT TGTATTCAAC AAGAATGCGC AAATATGTCA ACGTATTTGG
    -490        -480       -470       -460       -450
    AAGTCATCTT ATGTGCGCTG CTTTAATGTT TTCTCATGTA AGCGGACGTC
    -440        -430       -420       -410       -400
    GTCTATAAAC TTCAAACGAA GGTAAAAGGT TCATAGCGCT TTTTCTTTGT
    -390        -380       -370       -360       -350
    CTGCACAAAG AAATATATAT TAAATTAGCA CGTTTTCGCA TAGAACGCAA
    -340        -330       -320       -310       -300
    CTGCACAATG CCAAAAAAAG TAAAAGTGAT TAAAAGAGTT AATTGAATAG
    -290        -280  ClaI -270       -260       -250
                              ↓
    GCAATCTCTA AATGAATCGA TACAACCTTG CACTCACAC GTGGGACTAG
    -240        -230       -220       -210       -200
    CACAGACTAA ATTTATGATT CTGGTCCCTG TTTTCGAAGA GATCGCACAT
    -190        -180 BstEII-170       -160       -150
                             ↓
    GCCAAATTAT CAAATTGGTC ACCTTACTTG GCAAGGCATA TACCCATTTG
    -140        -130       -120       -110       -100
    GGATAAGGGT AAACATCTTT GAATTGTCGA AATGAAACGT ATATAAGCGC
    -90         -80        -70        -60        -50
    TGATGTTTTG CTAAGTCGAG GTTAGTATGG CTTCATCTCT CATGAGAATA
    -40         -30        -20        -10        -1          10
    AGAACAACAA CAAATAGAGC AAGCAAATTC GAGATTACCA ATGTTTAAAT
                 20         30         40         50         60
    CTGTTGTTTA TTCAATTTTA GCCGCTTCTT TGGCCAATGC AGGTACCATT
                 70         80   SalI
                                   ↓
    CCCTTAGGCA AACTAGCCGA TGTCGAC
```

Fig. 9 THE PROMOTER REGION OF THE GAPDH GENE

```
TaqI    -670       -660        -650        -640
 ↓
 TCGAGT TTATCATTAT CAATACTCGC CATTTCAAAG AATACGTAAA
-630       -620        -610        -600        -590
 TAATTAATAG TAGTGATTTT CCTAACTTTA TTAGTCAAA AAATTAGCCT
-580       -570        -560        -550        -540
 TTTAATTCTG CTGTAACCCG TACATGCCAA AATAGGGGGC GGGTTACACA
-530       -520        -510        -500        -490
 GAATATATAA CACTGATGGT GCTTGGGTGA ACAGGTTTAT TCCTGGCATC
-480       -470        -460        -450        -440
 CACTAAATAT AATGGAGCCC GCTTTTTAAG CTGGCATCCA GAAAAAAAAA
-430       -420        -410        -400        -390
 GAATCCCAGC ACCAAAATAT TGTTTTCTTC ACCAACCATC AGTTCATAGG
-380       -370        -360        -350        -340
 TCCATTCTCT TAGCGCAACT ACAGAGAACA GGGCACAAAC AGGCAAAAAA
-330       -320        -310        -300        -290
 CGGGCACAAC CTCAATGGAG TGATGCAACC TGCCTGGAGT AAATGATGAC
-280       -270        -260        -250        -240
 ACAAGGCAAT TGACCCACGC ATGTATCTAT CTCATTTTCT TACACCTTCT
-230       -220        -210        -200        -190
 ATTACCTTCT GCTCTCTCTG ATTTGGAAAA AGCTGAAAAA AAAGGTTGAA
-180       -170        -160        -150        -140
 ACCAGTTCCC TGAAATTATT CCCCTACTTG ACTAATAAGT ATATAAAGAC
-130       -120        -110        -100         -90
 GGTAGGTATT GATTGTAATT CTGTAAATCT ATTTCTTAAA CTTCTTAAAT
 -80        -70         -60         -50 DraI    -40
                                        ↓
 TCTACTTTTA TAGTTAGTCT TTTTTTAGT TTTAAAACAC CAAGAACTTA
 -30 TaqI   -20         -10          -1
     ↓
 GTTTCGAATA AACACACATA AATAAACAAA ATG
```

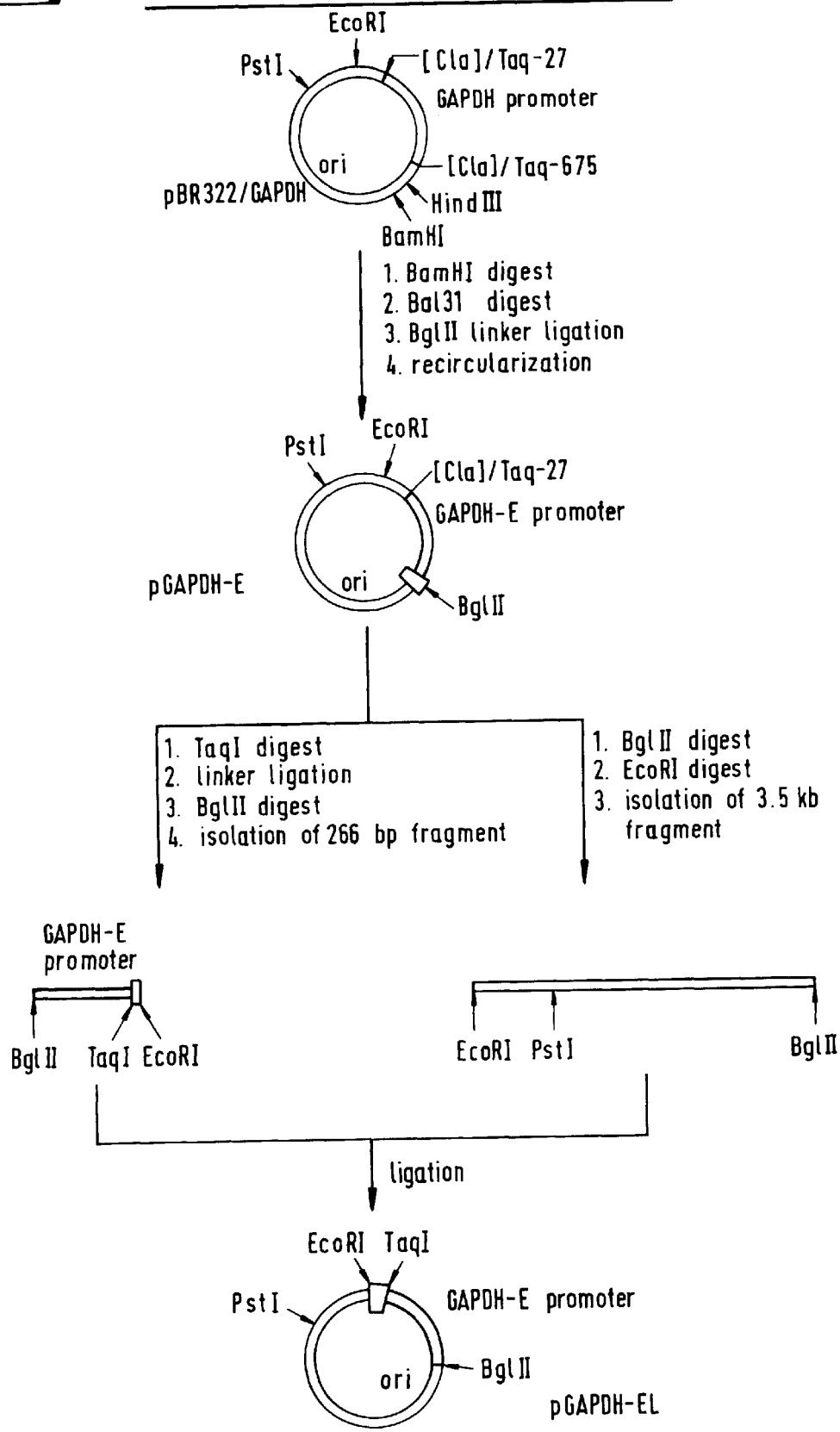
Fig. 10 CONSTRUCTION OF PLASMID pGAPDH-EL

Fig. 11 SEQUENCE OF BgIII-EcoRI FRAGMENTS FROM PLASMIDS pGAPDH-FL AND pGAPDH-EL, RESPECTIVELY, COMPRISING PART OF THE GAPDH PROMOTER a. pGAPDH-FL

```
                            5'-GATC TGCTGAAAAA AAAGGTTGAA
ACCAGTTCCC TGAAATTATT CCCCTACTTG ACTAATAAGT ATATAAAGAC
GGTAGGTATT GATTGTAATT CTGTAAATCT ATTTCTTAAA CTTCTTAAAT
TCTACTTTTA TAGTTAGTCT TTTTTTTAGT TTTAAAACAC CAAGAACTTA
GTTCGAATA AACACACATA AATAAAG-3'
``` b. pGAPDH-EL

```
            5'-GATCTGCGC ATGTATCTAT CTCATTTTCT TACACCTTCT
ATTACCTTCT GCTCTCTCTG ATTTGGAAAA AGCTGAAAAA AAAGGTTGAA
ACCAGTTCCC TGAAATTATT CCCCTACTTG ACTAATAAGT ATATAAAGAC
GGTAGGTATT GATTGTAATT CTGTAAATCT ATTTCTTAAA CTTCTTAAAT
TCTACTTTTA TAGTTAGTCT TTTTTTTAGT TTTAAAACAC CAAGAACTTA
GTTCGAATA AACACACATA AATAAAG-3'
```

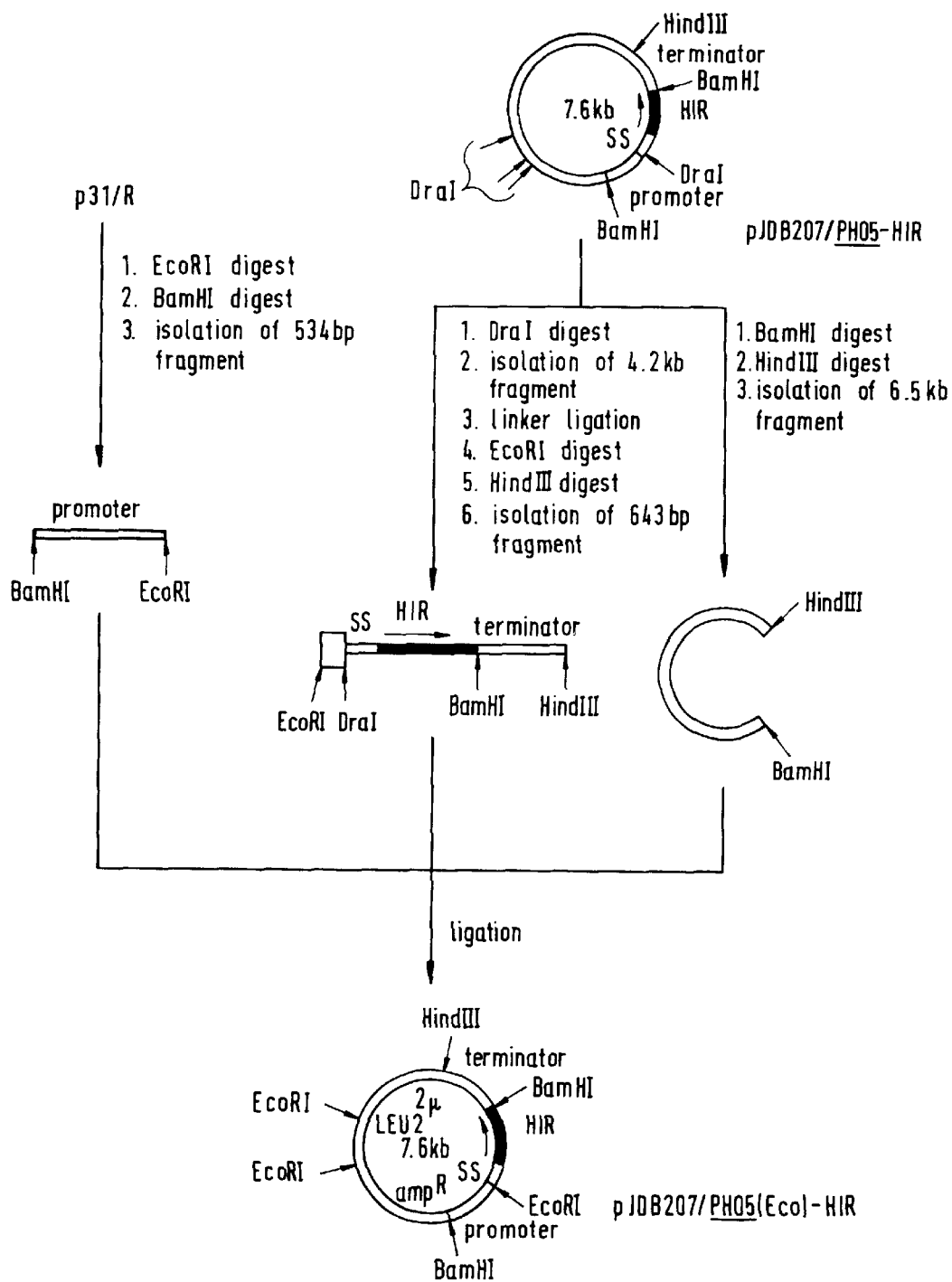
Fig. 12 CONSTRUCTION OF PLASMID pJDB207/PHO5(Eco)-HIR

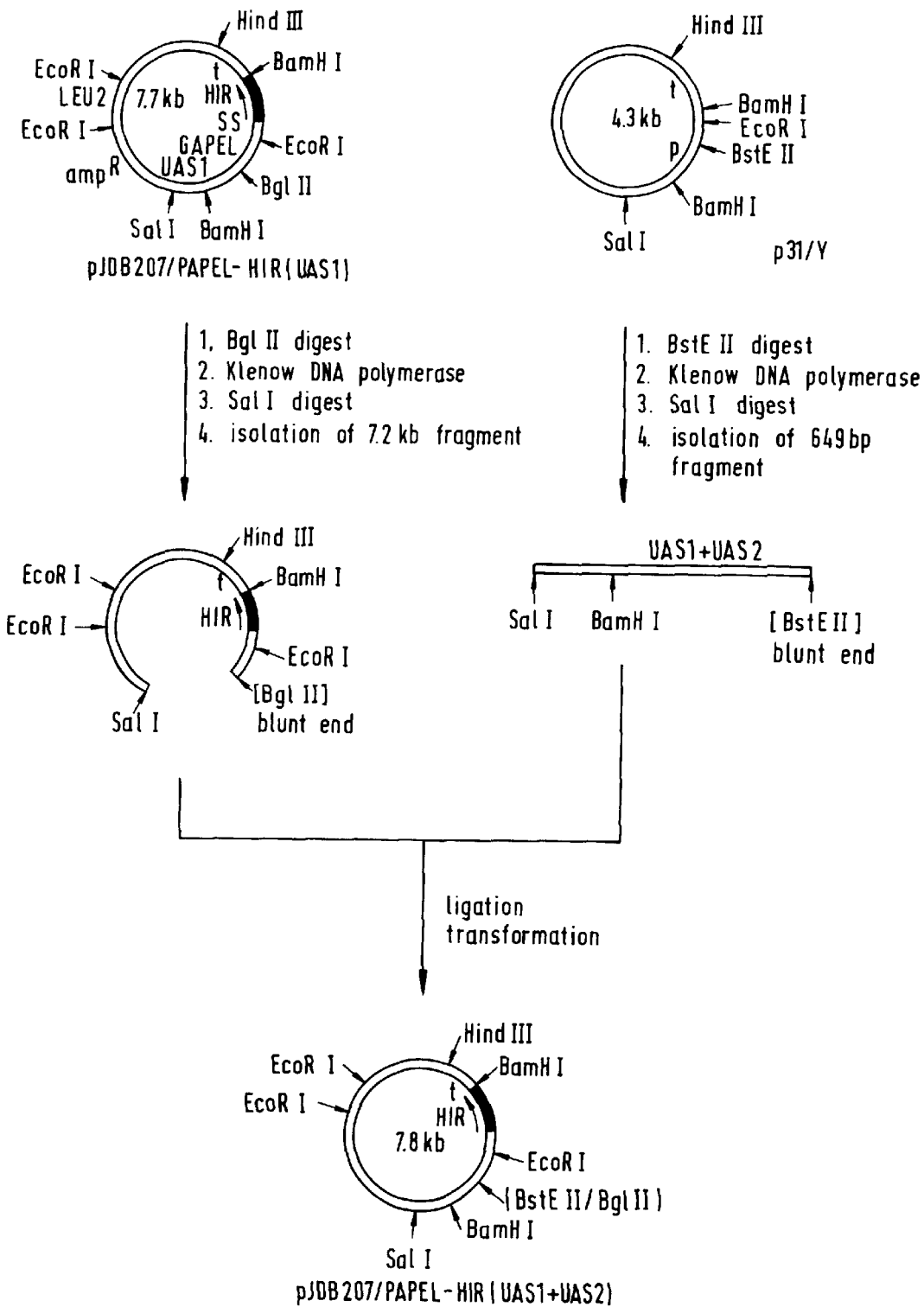
Fig. 13 CONSTRUCTION OF PLASMID pJDB207/PAPEL-HIR (UAS1+UAS2)

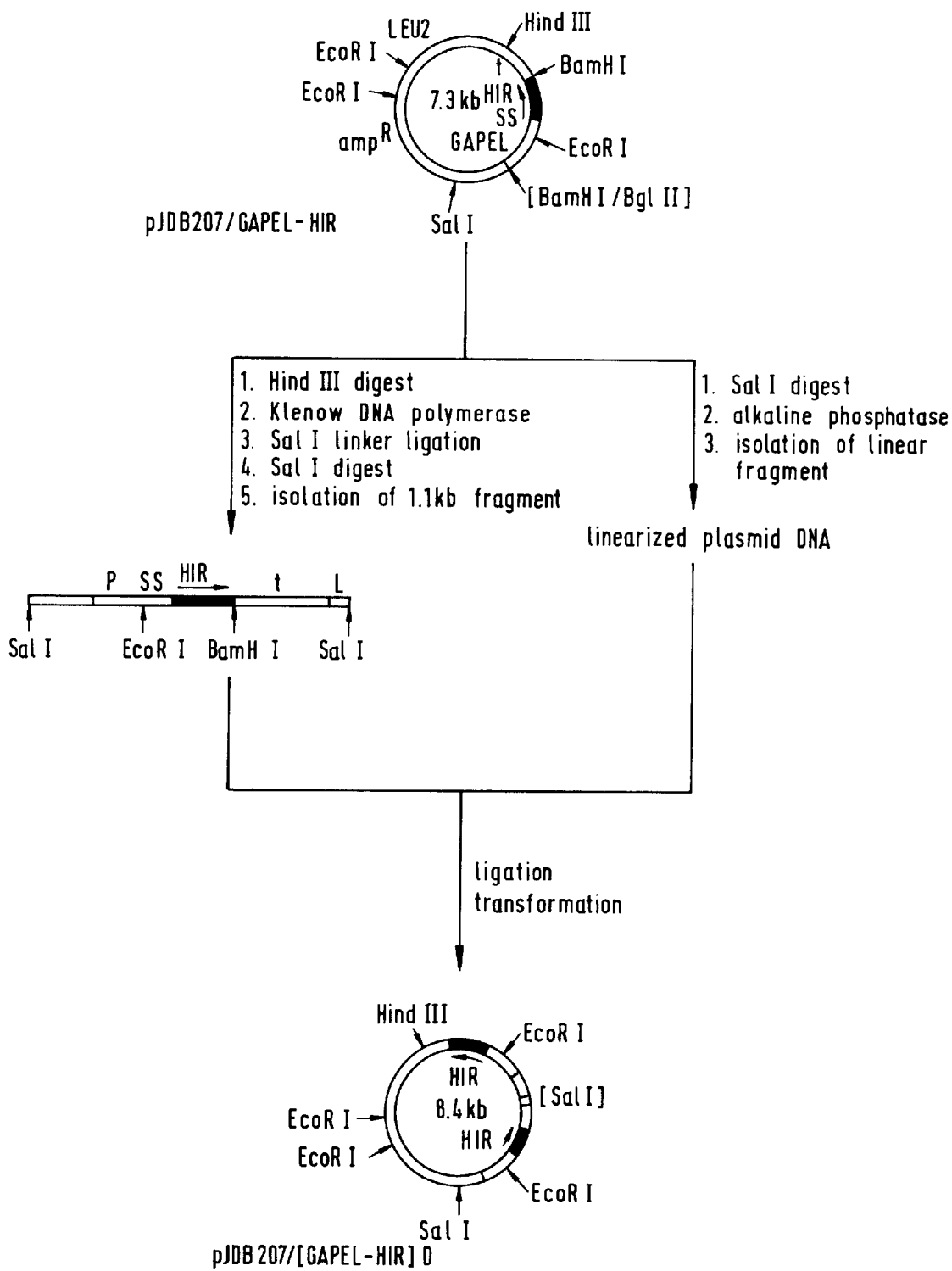
Fig. 14 CONSTRUCTION OF PLASMID pJDB207/[GAPEL-HIR]D

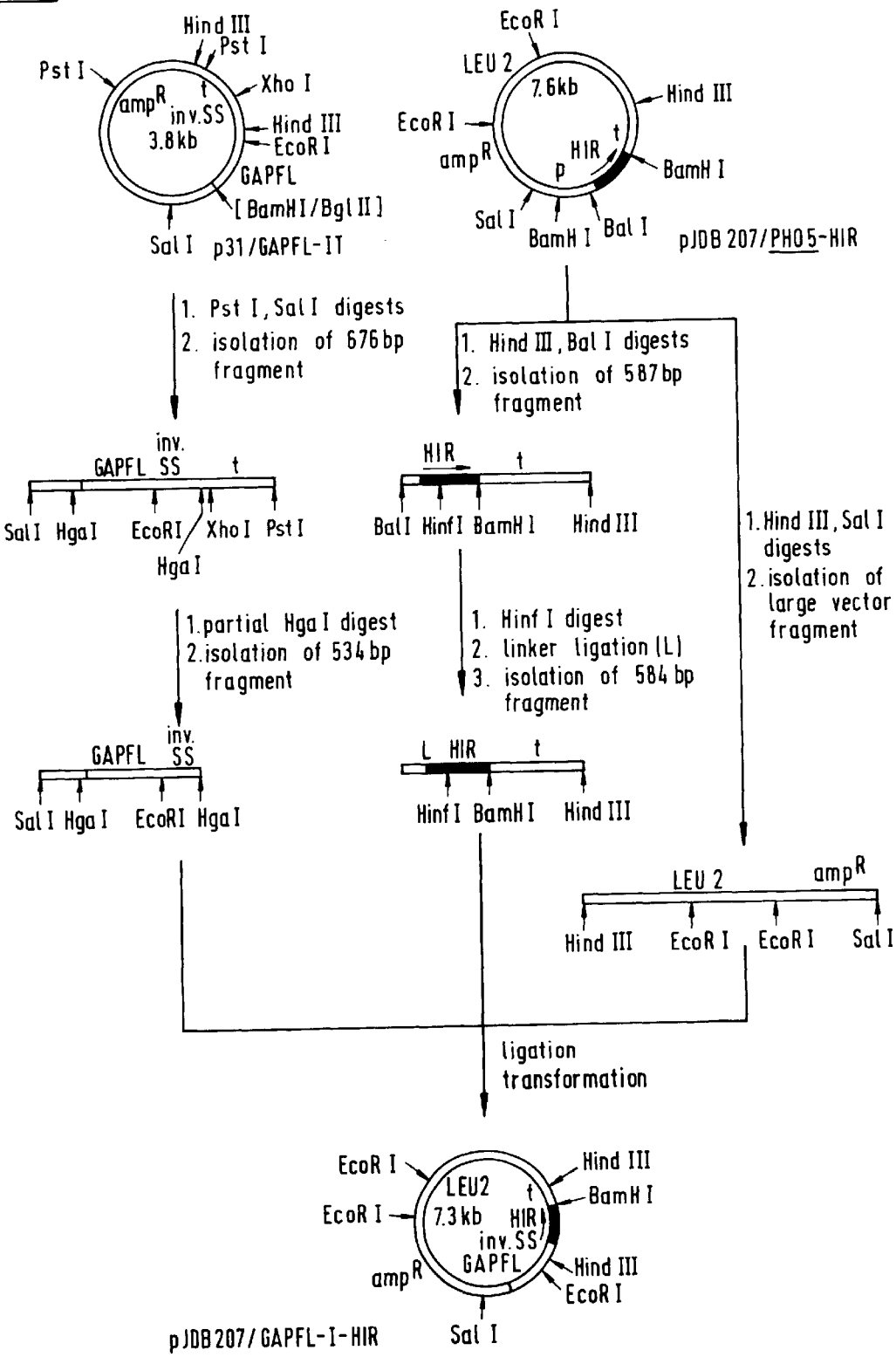

PRODUCTION OF THROMBIN INHIBITORS

This application is a continuation of application Ser. No. 938,102, filed Dec. 4, 1986, now abandoned.

The invention pertains to the field of recombinant DNA technology and concerns a method for the preparation of the thrombin inhibitor desulphatohirudin with the aid of genetically engineered eukaryotic cells, said genetically engineered eukaryotic cells, hybrid vectors carrying a gene for desulphatohirudin and methods for the preparation of said eukaryotic cells and said hybrid vectors.

Hirudin is an anticoagulant agent that occurs naturally in leeches (*Hirudo medicinalis*). Hirudin is not a single protein species but consists of at least three components designated hirudin variant 1 (HV1), hirudin variant 2 (HV2) (cf. European Patent Application No. 158,564) and "des-(Val)$_2$-hirudin" (cf. European Patent Application No. 158,986). The variants differ in structure from each other by a number of amino acids (especially, the N-terminal sequence of HV1 is Val-Val-Tyr, that of HV2 is Ile-Thr-Tyr and that of "des-(Val)$_2$-hirudin" is Thr-Tyr) but have an accumulation of hydrophobic amino acids at the N-terminus and of polar amino acids at the C-terminus, a tyrosine residue (Tyr$^{63}$) present as sulphate monoester, three disulphide bridges and the anticoagulant activity in common.

Hirudin, with a K$_i$-value (complex dissociation constant) of 6×10$^{-11}$M, is the strongest thrombin inhibitor known and is characterised by a specific affinity to thrombin. Other enzymes of the blood coagulation cascade are not inhibited by hirudin. In contrast to heparin which is the preferred anticoagulant in conventional anticoagulation therapy, hirudin exerts its inhibiting action directly on thrombin and, unlike the former, does not act through antithrombin III. The only pharmacologically detectable effect of purified hirudin is the inhibition of blood coagulation and the prophylaxis of thrombosis. No effect on heart rate, respiration, blood pressure, thrombocyte count, fibrinogen and haemoglobin could be observed when administered intravenously to dogs, even in high doses. In tests on rats, pigs and dogs, hirudin has proved effective in experimental thrombosis (induced either by stasis or by the injection of thrombin), in endotoxin shock, and also in DIC (disseminated intravascular coagulation). Whenever direct comparison tests have been carried out, hirudin has proved to be superior to heparin. Furthermore, hirudin has an extremely low toxicity, is non antigenic and shows an almost complete clearance via the kidneys in a biologically active form.

Although long known, hirudin has not as yet achieved the broad therapeutic use that might be expected on the basis of its excellent biological properties. Its extremely limited availability is a serious drawback which stands in the way of its widespread use in medicine. Up to now, hirudin preparations have been obtainable essentially from natural material(leech extracts), which is expensive and difficult to obtain, and employing time-consuming and costly isolation and purification processes [cf. P. Walsmann et al., Pharmazie 36, 653 (1981); European Patent Application No. 158,986]. In view of the relatively long sequence of 65 amino acids also the conventional peptide synthesis offers little hope of success for economic reasons. New methods must therefore be applied for the manufacture of adequate amounts of hirudin that render possible detailed clinical tests of its therapeutic potential and its broad therapeutic use in anticoagulation therapy.

Such methods are offered especially by recombinant DNA technology. By means of this technology it is possible to manufacture the most varied physiologically active polypeptides by culturing correspondingly genetically modified host organisms. In this context, it has to be mentioned that hirudin is presumably produced by leeches via a desulphatohirudin precursor which is post-translationally sulphated. It is expected that hosts other than leech lack the specific sulphate-transferring enzyme system and will therefore produce desulphatohirudins rather than hirudins. However, the biological activity is not injured by the absence of the sulphate group as is evidenced by the desulphatohirudin protein obtained by enzymatic removal of the sulphate group from the phenolic hydroxy group of the Tyr 63 residue of the corresponding hirudin protein (cf. European Patent Application No. 142,860).

In the recently published European Patent Application No. 158,564 the production of desulphatohirudin variants 1 and 2 and of analogues thereof by means of *E. coli* cells transformed with plasmids containing the structural genes for the respective desulphatohirudirsis disclosed. The anticoagulant activity measured in cell extracts of cultured *E. coli* cells and given in terms of anti-thrombin units ("ATU") amounts to 3,000–4,000 ATU/D$_{600}$/l culture which corresponds to a concentration of 0.2 mg hirudin/OD/l (based upon an estimated specific activity of 15,000–20,000 ATU/mg of pure hirudin).

Presumably the poor yield in hirudin activity obtained from transformed *E. coli* cells is attributable to an accumulation of most of the hirudin protein in an inactive form in the cytoplasm due to incorrect folding of the molecule. The correct folding depends on the formation of three disulphide bridges within the hirudin molecule which are essential for enzyme activity(cf. P. Walsmann et al., supra). Other naturally secreted mammalian proteins, such as bovine growth hormone, human tissue plasminogen activator and human γ-interferon are likewise essentially inactive when produced and accumulated in the cytoplasm of microorganisms [cf. R. A. Smith et al., Science 229, 1219 (1985)]. It is apparent that the secretion pathway may favor disulphide bond formation since most proteins containing disulphide bridges are extracellular. There are other features that make secretion most desirable:

Secreted proteins are generally easier to detect and to purify than intracellularly accumulated products;

secretion of desired products into the medium avoids the necessity of breaking up the host organisms in order to recover the product;

some heterologous proteins may have a toxic effect on the host organism. When secreted they are less likely to interfere with normal cellular functions;

secreted proteins are less likely to be digested by proteolytic enzymes than intracellularly accumulated proteins which are attacked by these enzymes upon disintegration of the cells.

Most secreted proteins are encoded on the DNA as preproteins with a signal peptide as an appended amino terminal extension of the mature amino acid sequence. The signal peptide plays an essential role during cotranslational insertion of the protein into the membranes of the endoplasmatic reticulum (ER). A signal peptidase cleaves the signal peptide in an early event on the luminal side of the ER. Further transport to the outer cell membrane involves Golgi and secretory vesicles. The protein is either secreted into the periplasmic space (e.g. acid phosphatase, invertase) or into the culture medium (e.g. α factor, killer toxin).

Since all eukaryotes seem to share the mechanisms for the expression of genetic information and for sorting the expressed proteins, the expression of eukaryotic genes proceeds with greater efficiency in an eukaryotic host than in *E.* coli. Among the eukaryotic organisms yeast is the easiest to handle and to cultivate. A number of heterologous proteins have been expressed successfully in yeast. However, it has not been possible so far to define essential features of a protein—except for an appended signal peptide—that would allow efficient secretion into the medium. Therefore, it is not possible to make reliable predictions whether or not a protein will be secreted. Thus, while 90% of total glucoamylase produced by transformed yeast (containing the genetic information for pre-glucoamylase) is secreted into the medium (PCT-Patent Application No. 84/2921) and high titers of epidermal growth factor (EGF) are found in the medium of cultured yeast containing the EGF gene with the appended α factor signal peptide (European Patent Application No. 116,201),only minor amounts or traces of β-endorphin (α-factor signal peptide, PCT-Patent Application No. 84/4330), leukocyte interferon A (invertase signal peptide, European Patent Application No. 127,304), human γ-interferon, human serum albumin, bovine interferons α1 and α2, tissue plasminogen activator, rennin and human insulin-like growth factor (α-factor signal peptide, European Patent Application No. 123,544), leukocyte interferons D and A, γ-interferon and human growth hormone (MGH) (interferon and MGH signal peptides, respectively, European Patent Application No. 88,632) are detectable in the medium, and no secretion of Pseudomonas carboxypeptidase $G_2(CPG_2)$ [$G_2(CPG_2)$ signal peptide, European Patent Application No. 121,352] and tissue plasminogen activator (PHO5 signal peptide, European Patent Application No. 143,081) by transformed yeast into the medium is observed.

Accordingly, whether or not a given protein having an appended signal peptide is secreted by yeast is unpredictable and depends above all on the selected protein.

Hence, it was uncertain, whether a selected protein, such as hirudin, having an appended signal peptide would be secreted, at least to a certain degree, by transformed host organisms, such as yeast.

Surprisingly, it has now been found that proteins with hirudin activity are secreted into the medium by eukaryotic host organisms which contain a DNA comprising a DNA sequence encoding a signal peptide upstream of and in reading frame with the structural gene for desulphatohirudin.

It is an object of the present invention to provide a method for the production and secretion of proteins with hirudin activity in an eukaryotic host organism. It is a further object of the invention to provide hybrid vectors comprising a DNA sequence encoding a signal peptide upstream of and in reading frame with the structural gene for desulphatohirudin, and eukaryotic host organisms transformed with said hybrid vectors.

DETAILED DESCRIPTION OF THE INVENTION

1. Process for the production of desulphatohirudin

The invention concerns a method for the production of proteins with hirudin activity comprising culturing under appropriate nutrient conditions an eukaryotic host organism transformed with a hybrid vector having one or multiple DNA inserts each comprising an eukaryotic expression control sequence, a DNA segment consisting of a first DNA sequence encoding a signal peptide upstream of and in reading frame with a second DNA sequence coding for mature desulphatohirudin which DNA segment is under transcriptional control of said expression control sequence, and a DNA sequence containing eukaryotic transcription termination signals, and isolating the proteins with hirudin activity from the culture medium and, if desired, isolating optionally additional protein with hirudin activity which is cell associated from the cell interior, and, if desired, converting a resulting protein with hirudin activity into a different protein with hirudin activity.

The term "DNA sequence coding for mature desulphatohirudin" is intended to embrace all structural genes coding for mature proteins having hirudin activity which are known to exist in and/or can be isolated from the leech genome, such as the structural genes for mature desulphatohirudin variants HV1, HV2, PA and for des-(Val)$_2$-desulphatohirudin (unless the latter is a mere artifact of expression of the HV1 gene). The term "mature desulphatohirudin" refers to desulphatohirudins which are devoid of any pre- and pro-sequences.

There are to be understood as "proteins with hirudin activity" those proteins obtained from the secreting host cells that have a thrombin-inhibiting action and a positive reaction with anti-hirudin antibodies and that have the primary structure of a desulphatohirudin, as well as modified, such as sulphated, derivatives thereof, e.g. the corresponding hirudins, and shortened derivatives thereof, such as desulphatohirudins lacking one to seven amino acids at the C-terminus.

Such proteins are especially those having the formulae

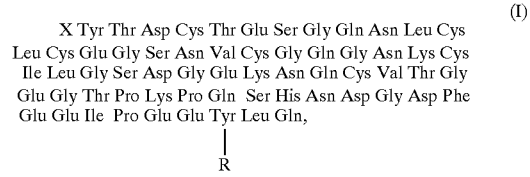

in which X represents the dipeptide residue Val-Val-(HV1) or Thr (Des-(Val)$_2$-hirudin) and R represents the phenolic hydroxy group of Tyr or a group of the formula —O—SO$_3$H, and the derivatives lacking the C-terminal amino acid Gln, the C-terminal dipeptide -Leu-Gln, the C-terminal tripeptide -Tyr(R)-Leu-Gln or the C-terminal tetrapeptide
  -Glu-Tyr(R)-Leu-Gln, or

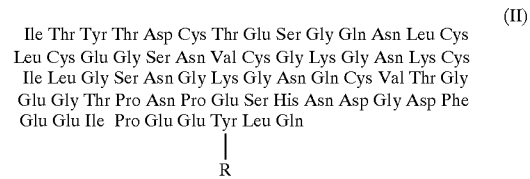

(HV2) in which R has the meanings given aboveor another hirudin variant named hirudin PA which is produced by leech (J. Dodt, Thesis, University of Munich, FRG, 1984) and has the formula

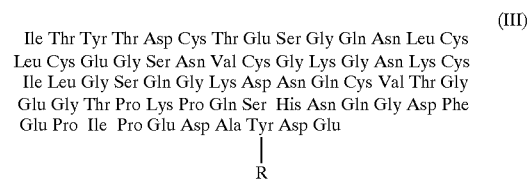

(PA) in which R has the meanings given above.

The preferred protein with hirudin activity is that of formula I in which X represents the residue Val-Val- and R represents the phenolic hydroxy group of Tyr, and the derivatives thereof that are shortened at the C-terminus by one to seven, especially one to four amino acids.

Suitable eukaryotic host organisms are cells of higher organisms, especially mammalians, in particular established human or animal cell lines, such as VERO or HeLa cells, or the Chinese hamster ovary (CHO) cell line, and yeast, such as *Saccharomyces cerevisiae*. The preferred host organism according to the present invention is yeast, especially strains of *Saccharomyces cerevisiae*.

The eukaryotic host organism, especially yeast, containing the above DNA sequences is cultured using methods known in the art.

Thus, transformed yeast strains according to the invention are cultured in a liquid medium containing assimilable sources of carbon, nitrogen and inorganic salts.

Various carbon sources are usable. Examples of preferred carbon sources are assimilable carbohydrates, such as glucose, maltose, mannitol or lactose, or an acetate such as sodium acetate, which can be used either alone or in suitable mixtures. Suitable nitrogen sources include, for example, amino acids, such as casamino acids, peptides and proteins and their degradation products, such as tryptone, peptone or meat extracts, furthermore yeast extract, malt extract, corn steep liquor, as well as ammonium salts, such as ammonium chloride, sulphate or nitrate which can be used either alone or in suitable mixtures. Inorganic salts which may be used include, for example, sulphates, chlorides, phosphates and carbonates of sodium, potassium, magnesium and calcium. Additionally, the nutrient medium may also contain growth promoting substances. Substances which promote growth include, for example, trace elements, such as iron, zinc, manganese and the like, or individual amino acids.

To a varying extent, yeast cells transformed with autonomously replicating plasmids, for example, plasmids containing yeast $2\mu$ plasmid DNA (infra) tend to lose the introduced hybrid plasmid. For this reason, such yeast cells have to be grown under selective conditions, i.e. conditions which require the expression of a plasmid-encoded gene for growth. Most selective markers currently in use and present in the hybrid vectors according to the invention (infra) are genes coding for enzymes of amino acid or purine biosynthesis. This makes it necessary to use synthetic minimal media deficient in the corresponding amino acid or purine base. However, genes conferring resistance to an appropriate biocide may be used as well [e.g. genes conferring resistance to cycloheximide, to the amino-glycoside G 418, to a heavy metal, or the like]. Yeast cells transformed with vectors containing antibiotic resistance genes are grown in complex media containing the corresponding antibiotic whereby faster growth rates and higher cell densities are reached.

Yeast cells transformed with DNA integrating into a chromosome do not require selective growth conditions. These transformed cells are sufficiently stable to allow growth without selective pressure. These cells are advantageously grown in complex media.

Yeast cells containing hybrid plasmids with a constitutive promoter (e.g. ADHI, GAPDH) express the desulphatohirudin gene controlled by said promoter without induction. However, if the desulphatohirudin gene is under the control of a regulated promoter (e.g. PGK or PHO5) the composition of the growth medium has to be adapted in order to obtain maximum levels of mRNA transcripts, i.e. when using the PHO5 promoter the growth medium must contain a low concentration of inorganic phosphate for derepression of this promoter.

The cultivation is carried out by employing conventional techniques. The culturing conditions, such as temperature, pH of the medium and fermentation time are selected in such a way that maximal levels of desulphatohirudin are produced. A chosen yeast strain is preferably grown under aerobic conditions in submerged culture with shaking or stirring at a temperature of about 25° to 35° C., preferably at about 30° C., at a pH value of from 4 to 8, for example at approximately pH 7, and for about 4 to 20 hours, preferably until maximum yields of proteins are reached.

It is surprisingly found that, irrespective of the host organism and the signal peptide used, most of the produced hirudin compounds are secreted into the culture medium whereas only a minor part remains cell associated. The precise ratio (secreted compounds/cell associated compounds) depends on the fermentation conditions and the recovery process applied. In general it amounts to about or more than 9:1. Accordingly, secreted hirudin is always strongly dominating.

The hirudin compounds can be isolated from the culture medium by conventional means. For example, the first step consists usually in separating the cells from the culture fluid by means of centrifugation. The resulting supernatant can be enriched for hirudin compounds by treatment with polyethyleneimine so as to remove most of the non-proteinaceous material, and precipitation of the proteins by saturating the solution with ammonium sulphate or by trichloroacetic acid. Host proteins, if present, can also be precipitated by means of acidification with acetic acid (for example 0.1%, pH 4–5). A further enrichment of hirudin compounds can be achieved by extracting the acetic acid supernatant with n-butanol. Other purification steps include, for example, desalination, chromatographic processs, such as ion exchange chromatography, gel filtration chromatography, partition chromatography, HPLC, reversed phase HPLC and the like. The separation of the constituents of the mixture is also effected by dialysis, according to charge by means of gel electrophoresis or carrier-free electrophoresis, according to molecular size by means of a suitable Sephadex column, by affinity chromatography, for example with antibodies, especially monoclonal antibodies, or with thrombin coupled to a suitable carrier for affinity chromatography, or by other processes, especially those known from the literature.

If it is desired to isolate any additional hirudin compounds which are cell associated, i.e. which have accumulated intracellularly or in the periplasmic space, some supplementary purification steps are required. Thus, in case the hirudin proteins have accumulated within the cells, the first step for the recovery of the desired proteins consists in liberating the proteins from the cell interior. In most procedures the cell wall is first removed by enzymatic digestion with glucosidases (infra). Subsequently, the resulting speroplasts are treated with detergents, such as Triton. Alternatively, mechanical forces, such as shearing forces (for example X-press, French-press) or shaking with glass beads, are suitable for breaking cells. In the case where the hirudin compounds are secreted by the host, especially yeast, cells into the periplasmic space, a simplified protocol can be used: The protein is recovered without cell lysis by enzymatic removal of the cell wall or by treatment with chemical agents, e.g. thiol reagents or EDTA, which give rise to cell wall damages permitting the produced protein to be released.

It is surprisingly found that apart from the desulphatohirudin compounds corresponding to the "DNA sequence coding for mature desulphatohirudin" some other desulphatohirudin compounds can be isolated from the culture broth which differ from the expected compounds by the absence of one to four amino acids at the C-terminus. Thus, culturing of yeast cells carrying the gene coding for desulphatohirudin variant HV 1 yields this variant as well as, in lower yields, desulphatohirudin compounds lacking the C-terminal amino acid Gln [Des-(Gln$^{65}$)-desulphatohirudin], the C-terminal dipeptide residue -Leu-Gln [Des-(Leu$^{64}$, Gln$^{65}$)-desulphatohirudin], the C-terminal tripeptide residue -Tyr-Leu-Gln [Des-(Tyr$^{63}$, Leu$^{64}$, Gln$^{65}$)-desulphatohirudin] and the C-terminal tetrapeptide residue -Glu-Tyr-Leu-Gln [Des-(Glu$^{62}$, Tyr$^{63}$, Leu$^{64}$, Gln$^{65}$-desulphatohirudin], respectively. These compounds may have been formed by (partial) proteolytical degradation of the primary expression product desulphatohirudin and have been identified in all culture broths, irrespective of the yeast host used and the fermentation conditions applied.

Des-(Gln$^{65}$)-desulphatohirudin, Des-(Tyr$^{63}$, Leu$^{64}$, Gln$^{65}$)-desulphatohirudin and Des-(Glu$^{62}$, Tyr$^{63}$, Leu$^{64}$, Gln$^{65}$)-desulphatohirudin are novel and are also objects of the present invention.

The test with anti-hirudin or anti-desulphatohirudin antibodies (for example, monoclonal antibodies obtainable from hydridoma cells), the thrombin test [M. U. Bergmeyer (ed.), Methods in Enzymatic Analysis, Vol. II, p. 314–316, Verlag Chemie,Weinheim (FRG) 1983] or the blood coagulation test [F. Markwardt et al., Thromb. Haemost. 47, 226 (1982)] can be used to detect the hirudin activity.

Hirudin compounds obtainable in accordance with the process can be converted in a manner known per se into different hirudin compounds.

Thus, for example, compounds of the formula I to III in which R represents the phenolic hydroxy group of Tyr can be converted by reaction with a sulphate, such as disodium sulphate, and a tyrosine sulphotfansferase, obtainables for example, from leech cells, into compounds of the formula I to III in which R represents a group of the formula —OSO$_3$H.

It is also possible to convert a desulphatohirudin compound obtained, for example desulphatohirudin variant HV 1, into a derivative thereof that lacks one to seven amino acids at the C-terminus, for example by the action of a suitable carboxypeptidase, such as carboxypeptidase Y.

The transformed eukaryotic host organisms according to the invention can be prepared by recombinant DNA techniques comprising the steps of preparing a DNA construct containing an eukaryotic expression control sequence, a DNA segment consisting of a first DNA sequence encoding a signal peptide upstream of and in reading frame with a second DNA sequence coding for mature desulphatohirudin which DNA segment is under transcriptional control of said expression control sequence, and a DNA sequence containing eukaryotic transcription termination signals, preparing a hybrid vector comprising said DNA construct, transforming a suitable eukaryotic host organism with the created hybrid vector, and selecting transformed host cells from untransformed host cells.

2. DNA constructs comprising the coding regions of a signal peptide and of desulphatohirudin The invention concerns a DNA construct containing an eukaryotic expression control sequence, a DNA segment consisting of a first DNA sequence encoding a signal peptide upstream of and in reading frame with a second DNA sequence coding for mature desulphatohirudin which DNA segment is under transcriptional control of said expression control sequence, and a DNA sequence containing eukaryotic transcription termination signals.

Several expression control sequences can be used for regulator of expression of the DNA sequences coding for the signal peptide and desulfatohirudin. In particular, expression control sequences of highly expressed genes of the host to be transformed are used.

For use in mammalian cells, the expression control sequences are preferably derived from vira. For example, suitable expression control sequences for use in mammalian cells are the early and late promoters of Simian Virus 40 (SV40), the vaccinia promoter, HTLV promoter or promoters derived from polyoma or Adenovirus 2.

Expression control sequences for yeast which are the most preferred host organisms according to the present invention are derived from the genomic DNA of yeast, especially of *Saccharomyces cerevisiae*. Preferably, the expression control sequence of a highly expressed yeast gene is used for the expression of desulphatohirudin. Thus the promoter of the TRP1 gene, the ADHI or ADHII gene, acid phosphatase (PHO5) gene, isocytochrome c gene, or a promoter of the enolase, glyceraldehyde-3-phosphate dehydrogenase (GAPDH), 3-phosphoglycerate kinase (PGK), hexokinase, pyruvate decarboxylase, phosphofructokinase, glucose-6-phosphate isomerase, 3-phosphoglycerate mutase, pyruvate kinase, triosephosphate isomerase, phosphoglucose isomerase and glucokinase genes, or a promoter of the yeast mating pheromone genes coding for the a- or α-factor, can be used. It is also possible to use hybrid promoters comprising upstream activation sequences (UAS) of one yeast gene and downstream promoter elements including a functional TATA box of another yeast gene, for example a hybrid promoter including the UAS(s) of the yeast PHO5 gene and downstream promoter elements including a functional TATA box of the yeast GAPDH gene. Preferred vectors of the present invention contain promoters with transcriptional control. Promoters of this type, e.g. the promoter of the PHO5 gene and PHO5-GAPDH hybrid promoters, can be turned on or off by variation of the growth conditions. For example, the PHO5 promoter can be repressed or derepressed at will, solely by increasing or decreasing the concentration of inorganic phosphate in the medium. A further preferred promoter according to the invention is the promoter of the GAPDH gene, especially a functional fragment thereof starting at nucleotide –300 to –180, in particular at nucleotide –263 or –199, and ending at nucleotide –5 of the GAPDH gene.

The DNA sequence encoding a signal peptide ("signal sequence") is preferably derived from eukaryotic, for example yeast, genes coding for polypeptides which are ordinarily secreted. Suitable signal sequences are, for example, the hirudin signal sequence obtainable from genomic leech DNA, yeast signal sequences, such as the signalandprepro sequences of the yeast invertase, a-factor, α-factor, pheromone peptidase, "killer toxin" and repressible acid phospatase (PHO5)genes and the glucomylase signal sequence from *Aspergillus awamori*. Alternatively, fused signal sequences may be constructed by ligating part of the signal sequence (if present) of the gene naturally linked to the promoter used, with part of the hirudin signal sequence. Those combinations are favoured which allow a precise cleavage between the signal sequence and the mature desulphatohirudin amino acid sequence. Additional sequences, such as pro- or spacer-sequences which may or may not carry specific processing signals can also be included in the constructions to facilitate accurate processing of precursor molecules. Alternatively fused proteins can be generated containing internal processing signals which allow proper maturation in vivo or in vitro. For example, the processing signals contain a Lys-Arg residue, which is recognized by a yeast endopeptidase located in the Golgi membranes. The preferred signal sequences according to the present invention are those of the yeast PHO5 gene coding for a signal peptide having the formula Met Phe Lys Ser Val Val Tyr Ser Ile Leu Ala Ala Ser Leu Ala Asn Ala, and of the yeast invertase gene coding for a signal peptide having the formula Met Leu Leu Gln Ala Phe Leu Phe Leu Leu Ala Gly Phe Ala Ala Lys Ile Ser Ala The DNA sequence coding for mature desulphatohirudin is especially selected from the structural genes for desulphatohirudins specified above. The preferred DNA sequence codes for desulphatohirudin variant 1 (HV1) and has the formula GTTGTTTACACCGACTGCACCGAATCTG-GTCAGAACCTGTGCCTGTGCGAAGGT CAA-CAAATGTGGCTGACGTGGCTTAGAC-CAGTCTTGGACACGGACACGCTTCCA TCTAACGTTTGCGGTCAGGGTAACAAAT-GCATCCTGGGTTCTGACGGTGAAAAAAACCAG AGATTGCAAACGCCAGTCCCATTGTT-TACGTAGGACCCAAGACTGC-CACTTTTTTGGTC TGCGTTACCGGTGAAGGTACCCCGAAAC-CGCAGTCTCACAACGACGGTGACTTCGAA ACGCAATGGCCACTTCCATGGGCTTTG-GCGTCAGAGTGTTGCTGCCACTGAAGCTT

GAAATCCCGGAAGAATACCTGCAG CTTTAGGGC-CTTCTTATGGACGTC.

A DNA sequence containing eukaryotic transcription termination signals is preferably the 3'flanking sequence of an eukaryotic gene which contains proper signals for transcription termination and polyadenylation. Suitable 3' flanking sequences are for example those of the gene naturally linked to the expression control sequence used. In case yeast is used as the host organism the preferred flanking sequences are those of the yeast PHO5 gene. Preferably, the DNA construct according to the present invention is provided at both ends with synthetic deoxynucleotide linkers which allow insertion and cloning of the construct in a cloning vector.

The eukaryotic expression control sequence, the DNA sequence coding for the signal peptide, the DNA sequence coding for mature desulphatohirudin and the eukaryotic transcription termination signals are operably linked to each other, i.e. they are juxtaposed in such a manner that their normal functions are maintained. Thus, the array is such that the expression control sequence effects proper expression of the signal peptide-desulphatohirudin gene complex, the transcription termination signals effect proper termination of transcription and polyadenylation and the signal sequence is linked to the desulphatohirudin gene in such a manner that secretion of desulphatohirudin occurs. Accordingly, if the expression control sequence and the signal sequence are derived from different genes, the expression control sequence is preferably joined to the signal sequence between the major mRNA start and the ATG of the gene naturally linked to the expression control sequence. The signal sequence should have its own ATG for translation initiation. The junction of these sequences is preferable effected by means of synthetic oligodeoxynucleotide linkers which may carry the recognition sequence of an endonuclease. On the other hand, the last codon of the signal sequence is directly linked to the first codon of the gene for desulphatohirudin.

The DNA constructs according to the invention may be prepared by methods known in the art, for example, by linking an eukaryotic expression control sequence, a DNA segment consisting of a first DNA sequence encoding a signal peptide upstream of and in reading frame with a second DNA sequence coding for desulphatohirudin, and a DNA sequence containing eukaryotic transcription termination signals in such a way that proper expression of the DNA segment and secretion of the produced desulphatohirudin is effected in an eukaryotic host organism.

Linkage of the various DNA sequences to yield the DNA constructs according to the invention may be effected by blunt end ligation or via suitable common restriction sites or synthetic linker molecules taking special care to a correct junction so that the normal functions of these DNA sequences are maintained. Thus, the signal sequence and the desulphatohirudin gene can be fused by blunt end ligation. Another approach for creating the correct junction of the signal sequence and the desulphatohirudin gene consists in restricting, if possible, the signal sequence near its 3' terminus and the desulphatohirudin near its 5' terminus so that each sequence lacks a predetermined number of base pairs. A synthetic oligodeoxynucleotide linker can then be constructed in such a way that, when joining the restricted signal sequence and the restricted desulphatohirudin gene via the connecting oligodeoxynucleotide, the missing base pairs are restored and the desulphatohirudin gene is in the proper reading frame relative to the signal sequence.

The DNA sequence coding for desulphatohirudin can be isolated from genomic leech DNA or a complementary double-stranded desulphatohirudin DNA (desulphatohirudin ds cDNA) is produced from desulphatohirudin mRNA, or a gene coding for the amino acid sequence of desulphatohirudin is produced by means of chemical and enzymatic processes. Genomic desulphatohirudin DNA and desulphatohirudin ds cDNA are obtained, for example, according to methods that are known per se. For example, genomic desulphatohirudin DNA is obtained from a leech gene bank that contains the desulphatohirudin gene by cloning the leech DNA fragments in a microorganism and identifying clones that contain desulphatohirudin DNA, for example by colony hybridisation using a radioactively labelled desulphatohirudin DNA-specific oligodeoxynucleotide that contains at least 15, and preferably from 15 to 30, deoxynucleotides. The resulting DNA fragments as a rule contain in addition to the desulphatohirudin gene other undesired DNA constituents that can be removed by treatment with suitable exo- or endo-nucleases.

Double-stranded desuiphatohirudin cDNA can be produced, for example, by isolating mRNA from suitable leech cells, which are preferably induced to form hirudin, enriching the desulphatohirudin mRNA in the resulting mRNA mixture in a manner known per se, using this mRNA as a template for the preparation of single-stranded cDNA, synthesising from this, with the aid of an RNA-dependent DNA polymerase, ds cDNA, and cloning the latter into a suitable vector. Clones that contain desulphatohirudin cDNA are identified, for example in the manner described above, by colony hybridisation using a radioactively labelled, desulphatohirudin DNA-specific oligodeoxynucleotide.

The desulphatohirudin gene can also be produced by chemical synthesis. The process is characterised in that segments of the coding and of the complementary strand of said gene are chemically synthesised and resulting segments are converted enzymatically into a structural gene for desulphatohirudin.

The chemical synthesis of DNA is well-known in the art and makes use of conventional techniques. Appropriate techniques have been compiled by S. A. Narang [Tetrahedron 39, 3 (1983)]. In particular, the methods described in European Patent Application No. 146,785 may be used and are herein incorporated by reference.

In an analogous manner, the signal sequence can be prepared by chemical synthesis or is isolated from chromosomal DNA of a suitable eukaryotic organism.

3. Hybrid Vectors Containing DNA Constructs with the Coding Regions of a Signal Peptide and of Desulphatohirudin According to the present invention there is further provided a hybrid vector having one or multiple DNA inserts each comprising an eukaryotic expression control sequence, a DNA segment consisting of a first DNA sequence encoding a signal peptide upstream of and in reading frame with a second DNA sequence coding for mature desulphatohirudin which DNA segment is under transcriptional control of said expression control sequence, and a DNA sequence containing eukaryotic transcription termination signals.

The hybrid vectors according to the invention are selected from the group consisting of a hybrid plasmid and a linear DNA vector and are further selected depending on the host organism envisaged for transformation.

The invention relates especially to a linear DNA vector having one or multiple DNA inserts each comprising an eukaryotic expression control sequence, a DNA segment consisting of a first DNA sequence encoding a signal peptide upstream of and in reading frame with a second DNA sequence coding for mature desulphatohirudin which DNA segment is under transcriptional control of said expression control sequence, and a DNA sequence containing eukaryotic transcription termination signals, said expression control sequence and said sequence containing transcription termination signals being derived from the same eukaryotic gene. Especially, the invention relates to a linear DNA vector comprising the yeast PHO5 promoter, the above DNA segment and the 3' flanking region of PHO5.

By virtue of the homologous 3' and 5' flanking sequences the whole linear DNA vector including the coding regions for the signal peptide and desulphatohirudin is stably integrated into the respective host chromosome, i.e. in the case of the yeast PHO5 promoter and 3' flanking sequences of the yeast PHO5 gene at the PHO5 locus in yeast chromosome II.

The invention relates also especially to hybrid plasmids which apart from the expression control sequence, the above DNA segment and the sequence containing transcription termination signals contain additional DNA sequences which are inessential or less important for the function of the promoter, i.e. for the expression of the desulphatohirudin gene, but which perform important functions, for example, in the propagation of the cells transformed with said hybrid plasmids. The additional DNA sequences may be derived from prokaryotic and/or eukaryotic cells and may include chromosomal and/or extra-chromosomal DNA sequences. For example, the additional DNA sequences may stem from (or consist of) plasmid DNA, such as bacterial or eukaryotic plasmid DNA, viral DNA and/or chromosomal DNA, such as bacterial, yeast or higher eukaryotic chromosomal DNA. Preferred hybrid plasmids contain additional DNA sequences derived from bacterial plasmids, especially $Escherichia$ $coli$ plasmid pBR322 or related plasmids, bacteriophage λ, yeast 2μ plasmid, and/or yeast chromosomal DNA.

In the preferred hybrid plasmids according to the invention, the additional DNA sequences carry a yeast replication origin and a selective genetic marker for yeast. Hybrid plasmids containing a yeast replication origin, e.g. an autonomously replicating segment(ars), are extrachromosomally maintained within the yeast cells after transformation and are autonomously replicated upon mitosis. Hybrid plasmids containing sequences homogous to yeast 2μ plasmid DNA can be used as well. These hybrid plasmids will get integrated by recombination into 2μ plasmids already present within the cell or will replicate autonomously.

As to the selective gene marker for yeast, any marker gene can be used which facilitates the selection for transformants due to the phenotypic expression of the marker. Suitable markers for yeast are particularly those expressing antibiotic resistance or, in the case of auxotrophic yeast mutants, genes which complement host lesions. Corresponding genes confer, for example, resistance to the antibiotic cycloheximide or provide for prototrophy in an auxotrophic yeast mutant, for example the URA1, URA3, ARG4, LEU2, HIS4, HIS3, TRP5 or TRP1 gene.

Advantageously, the additional DNA sequences which are present in the hybrid plasmids according to the invention also include a replication origin and a selective genetic marker for a bacterial host, especially $Escherichia$ $coli$. There are useful features which are associated with the presence of an $E.$ $coli$ replication origin and an $E.$ $coli$ marker in a yeast hybrid plasmid. Firstly, large amounts of hybrid plasmid DNA can be obtained by growth and amplification in $E.$ $coli$ and, secondly, the construction of hybrid plasmids is conveniently done in $E.$ $coli$ making use of the whole repertoire of cloning technology based on $E.$ $coli$. $E.$ $coli$ plasmids, such as pBR322 and the like, contain both $E.$ $coli$ replication origin and $E.$ $coli$ genetic markers conferring resistance to antibiotics, for example tetracycline and ampicillin, and are advantageously employed as part of the yeast hybrid vectors.

The additional DNA sequences which contain, for example, replication origin and genetic markers for yeast and a bacterial host (see above) are hereinafter referred to as "vector DNA" which together with the above DNA construct, containing inter alia the expression control sequence and the desulphatohirudin gene, is forming a hybrid plasmid according to the invention.

The hybrid vectors according to the invention may contain one or multiple DNA inserts each comprising, inter alia, the expression control sequence, the DNA sequence encoding the signal peptide and the DNA sequence coding for mature desulphatohirudin. If the hybrid vectors contain multiple DNA inserts, preferably 2 to 4 DNA inserts, these can be present in a tandem array or at different locations of the hybrid vector. Preferred hybrid vectors contain one DNA insert or DNA inserts in a tandem array. The DNA inserts are especially head to tail arranged.

The hybrid plasmids according to the invention are prepared by methods known in the art. The process for the preparation of the hybrid vectors comprises introducing one or multiple DNA constructs containing an eukaryotic expression control sequence, a DNA segment consisting of a first DNA sequence encoding a signal peptide upstream of and in reading frame with a second DNA sequence coding for mature desulphatohirudin which DNA segment is under transcriptional control of said expression control sequence, and a DNA sequence containing eukaryotic transcription termination signals, as such or introducing the components of said DNA constructs successively in the predetermined order into a vector DNA.

The construction of the hybrid plasmids according to the invention is performed applying conventional ligation techniques. The components of the plasmids are linked through common restriction sites and/or by means of synthetic linker molecules and/or by blunt end ligation.

The linear DNA vectors according to the invention correspond essentially to the DNA constructs specified in paragraph 2 and are prepared in an analogous manner.

4. Transformed eukaryotic host organisms

Another aspect of the invention involves eukaryotic host organisms transformed with a hybrid vector having one or multiple DNA inserts each comprising an eukaryotic expression control sequence, a DNA segment consisting of a first DNA sequence encoding a signal peptide upstream of and in reading frame with a second DNA sequence coding for mature desulphatohirudin which DNA segment is under transcriptional control of said expression control sequence, and a DNA sequence containing eukaryotic transcription termination signals, and mutants thereof.

Suitable eukaryotic host organisms are especially those specified above, in particular yeast including species of the genera Kluyveromyces, Candida, Pichia, Yarrowia, Saccharomyces, Schizosaccharomyces, Torulopsis, and related genera (cf. J. Lodder, The Yeasts, Amsterdam 1971), especially strains of Saccharomyces cerevisiae.

The transformed eukaryotic host organisms are selected from an eukaryotic host organism transformed with a hybrid plasmid having one or multiple DNA inserts each comprising an eukaryotic expression control sequence, a DNA segment consisting of a first DNA sequence encoding a signal peptide upstream of and in reading frame with a second DNA sequence coding for mature desulphatohirudin which DNA segment is under transcriptional control of said expression control sequence, and a DNA sequence containing eukaryotic transcription termination signals, and an eukaryotic host organism with said DNA insert(s) stably integrated in a host chromosome.

The process for the production of said transformed eukaryotic host cells comprises transforming eukaryotic host cells with a hybrid vector having one or multiple DNA inserts each comprising an eukaryotic expression control sequence, a DNA segment consisting of a first DNA sequence encoding a signal peptide upstream of and in reading frame with a second DNA sequence coding for mature desulphatohirudin which DNA segment is under transcriptional control of said expression control sequence, and a DNA sequence containing eukaryotic transcription termination signals.

The transformation of the eukaryotic host cells is accomplished by methods known in the art. For example, the transformation of yeast with the hybrid vectors may be accomplished according to the method described by Hinnen et al [Proc. Natl. Acad. Sci. USA 75, 1929 (1978)]. This method can be divided into three steps:

(1) Removal of the yeast cell wall or parts thereof using various preparations of glucosidases, such as snail gut juices (e.g. Glusulase® or Helicase®) or enzyme mixtures obtained from microorganisms (e.g. Zymolyase®) in osmotically stabilized solutions (e.g. 1M sorbitol).

(2) Treatment of the "naked" yeast cells (spheroplasts) with the DNA vector in the presence of PEG (polyethyleneglycol) and $Ca^{2+}$ ions.

(3) Regeneration of the cell wall and selection of the transformed cells in a solid layer of agar.

This regeneration is conveniently done by embedding the spheroplasts into agar. For example, molten agar (about 50° C.) is mixed with the spheroplasts. Upon cooling the solution to yeast growth temperatures (about 30° C.), a solid layer is obtained. This agar layer is to prevent rapid diffusion and loss of essential macromolecules from the spheroplasts and thereby facilitates regeneration of the cell wall. However, cell wall regeneration may also be obtained (although at lower efficiency) by plating the spheroplasts onto the surface of preformed agar layers.

Preferably, the regeneration agar is prepared in a way to allow regeneration and selection of transformed cells at the same time. Since yeast genes coding for enzymes of amino acid biosynthetic pathways are generally used as selective markers (supra), the generation is preferably performed in yeast minimal medium agar. If very high efficiencies of regeneration are required the following two step procedure is advantageous: (1) regeneration of the cell wall in a rich complex medium, and (2) selection of the transformed cells by replica plating the cell layer onto selective agar plates.

When the above linear DNA vector is used for transforming the eukaryotic host cells, transformation is preferably done in the presence of a second vector containing a selective marker for yeast. This cotransformation allows enrichment for those host cells which have taken up DNA that cannot be directly selected for. Since competent cells take up any type of DNA a high percentage of cells transformed with a selective vector will also harbor any additional DNA (such as the above linear DNA vector).

The transformed eukaryotic host organisms, especially the transformed yeast strains, containing the hybrid plasmids according to the invention or having the linear DNA vector comprising the desulphatohirudin gene stably integrated in a host chromosome can be improved in production of desulphatohirudin by mutation and selection using methods known in the art. The mutation can be effected, for example, by U.V. irradiation or suitable chemical reagents. Especially preferred is the production of protease deficient mutants, especially yeast mutants, so as to avoid proteolytic degradation of the produced desulphatohirudin within the cells. Suitable mutants can be selected and isolated by conventional means.

The invention relates especially to the DNA constructs comprising the desulphatohirudin gene, the hybrid vectors, the transformed eukaryotic host organisms and to the processes for the preparation thereof as well as to the process for the production of proteins with hirudin activity as described in the Examples.

BRIEF DESCRIPTION OF THE DRAWINGS

In the following experimental part various embodiments of the present invention are described with reference to the accompanying drawings in which:

FIGS. 1 and 2 are schematic diagrams showing the construction of plasmids pML300 and pML305, respectively.

FIG. 3 depicts the construction of plasmid pHRi148 containing the trp promoter.

FIG. 4 shows the construction of expression plasmid pML310.

FIG. 5 is a schematic diagram showing the isolation of a DNA fragment coding for mature desulphatohirudin.

FIG. 6 shows schematically the construction of an expression plasmid for secretion of desulphatohirudin.

FIG. 7 shows schematically the construction of an expression plasmid for intracellular expression of desulphatohirudin.

FIG. 8 depicts the DNA sequence of the BamHI-SalI restriction fragment of PHO5 including the PHO5 promoter region.

FIG. 9 shows the DNA sequence of the promoter region of the GAPDH gene.

FIG. 10 is a schematic diagram showing the construction of plasmid pGAPDH-EL.

FIG. 11 depicts the sequences of the GAPDH promoter fragments present in plasmids pGAPDH-FL and pGAPDH-EL.

FIG. 12 shows the construction of plasmid pJDB207/PHO5 (Eco)-HIR.

FIG. 13 shows the construction of plasmid pJDB207/PAPEL-HIR(UAS1+UAS2).

FIG. 14 depicts the construction of plasmid pJDB207/[GAPEL-HIR]D.

FIG. 15 is a schematic diagram showing the construction of plasmid pJDB207/GAPFL-I-HIR.

The following abbreviations are used in the figures: p promoter, SS signal sequence, t terminator, L linker.

The following Examples serve to illustrate the present invention but should not be construed as a limitation thereof.

Experimental Part

The meanings of the abbreviations used in the Examples are as follows:
TNE solution that contains 100 mM NaCl, 50 mM tris.HCl pH 7.5 and 5 mM EDTA,
SDS sodium dodecyl sulphate
EDTA ethylenediaminetetraacetic acid
DTT 1,4-dithiothreitol (1,4-dimercapto-2,3-butanediol)
BSA bovine serum albumin
EtBr ethidium bromide
tris tris-(hydroxymethyl)-aminomethane
tris.HCl tris monohydrochloride

EXAMPLE 1

Manufacture of Protected Nucleoside-polystyrene Resin

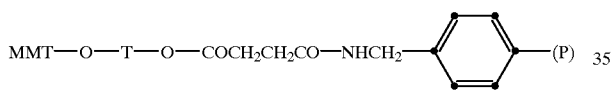

750 mg of succinic acid anhydride and 910 mg of 4-dimethylaminopyridine are added to 2.57 g (5 mmol) of 5'-(4-methoxytrityl)-thymidine (MMT-O-T-OH) in 20 ml of absolute pyridine and the whole is left at room temperature for 16 hours. After concentrating the pyridine solution, this is taken up in 200 ml of ethyl acetate, extracted by shaking twice, with 200 ml of 0.1M phosphate buffer each time with the addition of 10 ml of saturated sodium chloride solution, washed again with saturated sodium chloride solution, dried, concentrated and hexane is added dropwise. The precipitated product is separated off and triturated twice with ether, then dissolved in 300 ml of ethyl acetate and extracted by shaking at 0° C. with 180 ml of 0.1M potassium bisulphate of pH 2.5. After washing twice with water, the ethyl acetate solution is dried with sodium sulphate, filtered, 0.5 ml of pyridine is added and the whole is concentrated and diluted by the dropwise addition of hexane. The precipitated succinic acid derivative is removed by filtration.

1.0 g of this compound are dissolved together with 190 mg of N-hydroxysuccinimide in 4 ml of ethyl acetate and 2 ml of dimethylformamide, and 370 mg of N,N'-dicyclohexylcarbodiimide are added at 0° C. After standing overnight in a refrigerator, the precipitated N,N'-dicyclohexyl urea is filtered off, the filtrate is diluted with ethyl acetate, extracted with cold 0.1M sodium bicarbonate and water, dried and concentrated to dryness by evaporation in vacuo. The residue is chromatographed with ethyl acetate on silica gel. TLC: $R_f$ 0.45 in dichloromethane/methanol (9:1).

100 mg of this N-succinimidoylsuccinic acid ester are stirred for 20 hours with 1 g of aminomethylpolystyrene (amine content 110 $\mu$mol/g) in 2 ml of dichloromethane and 4 ml of dimethylformamide. The polymer resin is filtered off and extracted by washing with dimethylformamide, methanol, dichloromethane and methanol. After drying, the amino groups that have not reacted are acetylated by stirring the resin in 6 ml of pyridine with 1 ml of acetic anhydride and 100 mg of 4-dimethylaminopyridine for 30 minutes. The polymer resin is extracted by washing with dichloromethane, dimethylformamide, methanol and dichloromethane, and dried until a constant weight is reached. The spectroscopic methoxytrityl (MMT)-determination gives a charge of 57 $\mu$mol/g.

EXAMPLE 2

The following protected nucleoside/polystyrene resin is manufactured analogously to Example 1:

from 5'-(4-methoxytrityl)-N-isobutyryl-deoxyguanosine, charge 32 $\mu$mol/g.

EXAMPLE 3

Synthesis of the trinucleotide

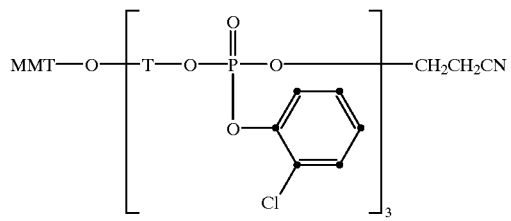

a) Synthesis of the Dinucleotide:

7.73 g (15 mmol) of 5'-(4-methoxytrityl)-thymidine (MMT-O-T-OH) are twice concentrated by evaporation with absolute pyridine. The residue is dissolved in 20 ml of absolute tetrahydrofuran and added dropwise to 80 ml of a 0.2M solution of 2-chlorophenyl-di-(1-benzotriazolyl)-phosphate in tetrahydrofuran while stirring and with the exclusion of moisture and the reaction mixture is stirred for 1 hour at room temperature. The resulting solution of 2-chlorophenyl-1-benzotriazolyl-5'-(4-methoxytrityl)-thymidine-3'-phosphate is divided into 3 portions.

α) Hydrolysis to triethylammonium-2-chlorophenyl-5'-(4-methoxytrityl)-thymidine-3'-phosphate:

100 ml of 0.5M triethylammonium bicarbonate are added to a third of the above solution of 2-chlorophenyl-1-benzotriazolyl-5'-(4-methoxytrityl)-thymidine-3'-phosphate while cooling. After 15 minutes extraction is carried out with dichloromethane. The dichloromethane solution is washed with water, concentrated, and petroleum ether is added dropwise thereto. The resulting precipitate is filtered off with suction, extracted by washing with ether/petroleum ether 1:1 and dried in vacuo. TLC: $R_f$ 0.35 in dichloromethane/methanol/water (75:22:3).

β) Esterification to 2-cyanoethyl-2-chlorophenyl-5'-(4-methoxytrityl)-thymidine-3¹-phosphate ans removal of the 4-methoxytrityl protecting group:

1.3 ml of 2-cyanoethanol and 2 ml of pyridine are added to a third of the solution of 2-chlorophenyl-1-benzotriazolyl-5'-(4-methoxytrityl)-thymidine-3'-phosphate. The mixture is left to stand overnight at room temperature. The solvents are distilled of in vacuo and the residue is dissolved in ethyl acetate and repeatedly extracted by shaking with 0.1M phosphate buffer of pH 7 and water. The organic phase is dried, concentrated and added dropwise to hexane. The precipitate is filtered off, dissolved in 50 ml of dichloromethane/methanol 7:3 and, at 0° C., a solution of 3.8 g of p-toluene-sulphonic acid monohydrate in 75 ml of dichloromethane/methanol 7:3 is added. After 2 hours, the reaction solution is diluted with dichloromethane and extracted by shaking with a cold sodium bicarbonate solution. The organic phase is concentrated and hexane is added. The precipitated 2-cyanoethyl-2-chlorophenyl-thymidine-3'-phosphate is chromatographed on silica gel with dichloromethane/methanol 96:4. TLC: $R_f$ of 0.45 in dichloromethane/methanol (9:1).

γ) Condensation to the 5'-(4-methoxytrityl)-3'-cyanoethyl-bis-thymidine dinucleotide:

2.2 g of 2-cyanoethyl-2-chlorophenyl-thymidine-3'-phosphate are dehydrated by twice concentrating by evaporation with absolute pyridine, and the product is dissolved in 20 ml of absolute tetrahydrofuran and added to the remaining third of the solution of 2-chlorophenyl-1-benzotriazolyl-5'-(4-methoxytrityl)-thymidine-3'-phosphate. After 18 hours at room temperature 10 ml of water and 200 ml of ethyl acetate are added to the reaction solution while cooling with ice. The organic phase is washed repeatedly with sodium bicarbonate and water, dried over sodium sulphate and concentrated to a small volume. The dinucleotide, protected in the phosphate moiety and at the 5'- and 3'-end, is precipitated by adding dropwise to ether/hexane 1:1. TLC: $R_f$ 0.48 in dichloromethane/methanol (9:1).

b) Synthesis of the Trinucleotide:

1.17 g (1 mmol) of the above-described fully protected dinucleotide are dissolved in 30 ml of dichloromethane/methanol 7:3 and, while cooling with ice, a solution of 1.9 g of p-toluenesulphonic acid monohydrate in 20 ml of dichloromethane/methanol 7:3 is added. After 2 hours, ice-cold sodium bicarbonate solution is added and extraction is carried out with dichloromethane. The organic phase is dried, concentrated and added dropwise to hexane. The precipitated crude dinucleotide with a free 5'-hydroxy group is chromatographed on silica gel with a gradient of 2–8% methanol in dichloromethane. TLC: $R_f$ 0.33 in dichloromethane/methanol (9:1).

850 mg of this 5'-hydroxy-dinucleotide and 1.06 g of triethylammonium-2-chlorophenyl-5'-(4-methoxytrityl)-thymidine-3'-phosphate [cf. paragraph a)α)] are twice concentrated by evaporation with pyridine, then dissolved in 10 ml of absolute pyridine and 560 mg of 1-mesitylenesulphonyl-3-nitro-1,2,4-triazole (MSNT) are added. After 2 hours, 2 ml of ice-cold water are added and, after a further hour, extraction is carried out with dichloromethane. The organic phase is washed with saturated sodium bicarbonate solution and water, dried, concentrated and ether is added. The precipitated trinucleotide is purified by chromatography on silica gel. $R_f$ 0.45 in dichloromethane/methanol (9:1).

EXAMPLE 4

Analogously to Example 3, the Following Protected Trinucleotides of the General Formula

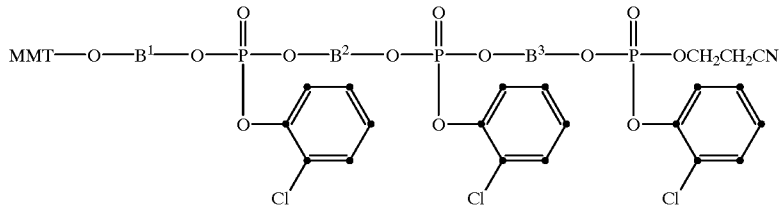

abbreviated to $B^1B^2B^3$, are manufactured. The following abbreviations are used for the nucleosides $B^1$, $B^2$, $B^3$:

A=N-benzoyl-deoxyadenosine
C=N-benzoyl-deoxycytidine
G=N-isobutyryl-deoxyguanosine
T=thymidine

| Compound | $R_f{}^{a)}$ | Compound | $R_f{}^{a)}$ |
|---|---|---|---|
| TTT | 0.45 | ATG | 0.48 |
| TTC | 0.55 | ACT | 0.53 |
| TCT | 0.46 | ACC | 0.48 |
| TAC | 0.56 | ATT | 0.55 |
| TGC | 0.44 | ACA | 0.53 |
| TAG | 0.60 | AAC | 0.46 |
| TGT | 0.42 | AAA | 0.51 |
| TGA | 0.44 | AGT | 0.45 |
| CTT | 0.53 | AGG | 0.38 |
| CTG | 0.46 | GTT | 0.45 |
| CCT | 0.45 | GTC | 0.44 |
| CCC | 0.59 | GTG | 0.35 |
| CCG | 0.47 | GCA | 0.49 |
| CCA | 0.51 | GCG | 0.48 |
| CAT | 0.55 | GAT | 0.44 |
| CAC | 0.51 | GAC | 0.48 |
| CGC | 0.46 | GAG | 0.48 |
| CGA | 0.38 | GAA | 0.50 |
| CAG | 0.44 | GGC | 0.42 |
| CGG | 0.38 | GGT | 0.46 |
| CGT | 0.49 | GGG | 0.35 |
|  |  | GGA | 0.44 | a)Thin layer chromatogram on silica gel in dichloromethane/methanol 9:1

EXAMPLE 5

Synthesis of the DNA Fragment of a Length of 67 Bases from Base No. 96 to Base No. 162 of the DNA Strand 96/97)

a) Removal of the 2-cyanoethyl Protecting Group from the Trinucleotides:

10 μmol of the trinucleotides from Example 3 or 4 are dissolved, with the exclusion of moisture, in 60 μl of pyridine/acetonitrile/triethylamine 1:1:1. After 1 hour at room temperature, 0.7 ml of peroxide-free ether is added dropwise and the precipitate is removed by centrifuging. The crude triethylammonium salt is dissolved in 50 µl of pyridine and again precipitated with 0.5 ml of ether, centrifuged off, and dried in a high vacuum for 15 hours.

b) Coupling the Partially Protected Trinucleotides with the Oligonucleotide Chain Bonded to Polystyrene Resin:

All operations are carried out with the exclusion of moisture in a reaction vessel of 220 µl capacity with microprocessor-controlled addition of solvent and reagent. 13 mg (0.74 µmol) of the thymidine/polystyrene resin (Example 1) are placed in the reaction vessel and subjected to the following operations:

1. Methylene chloride, 2 ml/min., 4 min.
2. Methylene chloride/isopropanol (85:15), 2 ml/min., 2 min.
3. Zinc bromide 1M and 1,2,4-triazole 0.02M in methylene chloride/isopropanol (85:15), 2 ml/min., 2–3.5 min.
4. Methylene chloride/isopropanol (85:15), 2 ml/min., 4 min.
5. Triethylammonium acetate 0.5M in DMF, 2 ml/min., 5 min.
6. Molecular sieve-dried pyridine, 2 ml/min., 3 min.
7. Tetrahydrofuran (peroxide-free, molecular sieve-dried), 2 ml/min., 3 min.
8. Nitrogen stream, 10 min.
9. Injection of 10 µmol of trinucleotide GTC (trimethylammonium salt from paragraph a) and 8.9 mg (30 µmol) of $^1$-mesitylenesulphonyl-3-nitro-1,2,4-triazole (MSNT) dissolved in 150 µl of pyridine.
10. 45° C., 20 min.
11. Pyridine, 2 ml/min., 4 min.
12. Acetic anhydride 5% and 4-dimethylaminopyridine 2.5% in pyridine, 2 ml/min., 4 min.
13. Pyridine, 2 ml/min., 4 min.
14. Pyridine/isopropanol (1:1), 2 ml/min., 3 min.

All 14 operations are repeated 21 times, but in the 9th operation, instead of CTC the following trinucleotides, respectively, are used in the form of their triethylammonium salts (paragraph a)) in the sequence indicated: GCA, ACC, GAA, CCC, TAC, AGG, TGA, CGC, TAC, CGT, CTG, CCA, AAA, AAA, TGA, CGG, TGA, TTC, GGG, CCT, CAT. The mean coupling yield is 97%. The end product has the following structure:

M M T-
CATCCTGGGTTCTCACGTGAAAAAAAC-
CAGTGCGTTACCGCTCAACGTAC-
CCCCAAACCGCAG TCT-polystyrene c) Removal of the DNA Fragment from the Carrier and Removal of the Protecting Groups:

40.0 mg (approximately 0.60 µmol) of DNA synthesis resin 96/67 are maintained at 50° C. for 3 hours and at room temperature for 12 hours with 66 mg (0.40 mmol) of o-nitrobenzaldoxime and 50 µl (0.40 mmol) of 1,1,3,3-tetramethylguanidine in 400 µl of 95% pyridine. After blowing off the pyridine with nitrogen, 1.6 ml of aqueous ammonia (33%) are added to the residue and the whole is maintained for 24 hours at 50° C. in a closed vessel.

The liquid phase separated off is freed of ammonia in vacuo and washed 3 times with 3 ml of peroxide-free diethyl ether each time. After removing the lower molecular constituents on a Biogel P6 column (100–200 mesh, 3×66 cm, 0.01 molar trimethylammonium bicarbonate pH 7.5, 1.5 ml/min.), 285 ODs (260 nm) of DNA are isolated.

A total of 60 ODs are separated on an HPLC column (PPP-1/Hamilton, 250×4.6 mm). Gradient (solution A: 0.05M triethylammonium acetate pH 7.0; solution B: solution A:acetonitrile 1:1): 30% B in A 60% B in A in 20 min. at 50° C. and 2 ml/min. The lipophilic main peak (retention time approximately 14 min.) is collected, concentrated over a DE52 cellulose (Whatman) column, eluted and precipitatd with ethanol. To remove the 4-methoxytrityl protecting group, the precipitate is dissolved in 50 µl of acetic acid/H$_2$O (4:1) and maintained at room temperature for 45 minutes. The reaction product is lyophilised, precipitated with ethanol and, for purification, electrophoretically separated on an 8% polyacrylamide gel (7M urea). The band corresponding to the desired DNA size is cut out and the product is electroeluted, concentrated over DE52 cellulose and the DNA 96/97 of the following structure

5'-CATCCTGGGTTCTGACGGTGAAAAACCAGTG
CGTTACCGGTGAGGTACCCCGAAACCG
CAGTCT-3' is precipitated with ethanol.

EXAMPLE 6

The following DNA fragments (5'-3') are produced analogously to Example 5:

1/58
CTGGAATTCATGGTTGTTTACACCGACT-
GCACCGAATCTGGTCAGAACCTGTGCCTGT

46/64 complementary
CAGAACCCAGGATGCATTTGTTAcCCT-
CACCGCAAACGTTAGAACCTTCGCACAG-
GCACAGGTT 154/64 complementary
CAGGATCCTACTGCAGGTATTCTTCCGG-
GATTTCTTCGAAGTCACCGTCGTTGT-
GAGACTGCGG

EXAMPLE 7

Phosphorylation of the Fragments 1/58, 46/64 Complementary, 96/67 and 154/65 Complementary The phosphorylation and the radioactive labelling at the 5'-ends is effected with [γ-$^{32}$P]ATP and T$_4$ polynucleotide kinase (Boehringer) as described in Molecular Cloning, A laboratory Manual (ed. T. Maniatis et al.), Cold Spring Harbor Lab., 1982, p. 125

EXAMPLE 8

Polymerisation to Duplex II (fragment F$_2$ of the Desulphatohirudin HV1 Gene)

50 pmol in each case of kinased fragment 96/67 and kinased fragment 154/64 are dissolved in 24 µl of water, the solution is heated at 90° C. for 3 minutes and cooled to 12° within a period of 5 minutes. After the addition of 4 µl of endo-R buffer (0.1 molar tris.HCl pH 7.5, 66 mM MgCl$_2$, 66 mM β-mercaptoethanol, 0.6M NaCl), 10 µl of deoxynucleoside triphosphate mixture (dATP, dCTP, dGTP, TTP, each 2×10$^{-3}$ molar, adjusted with NH$_3$ to pH 7.0) and 2 µl (10 units) of DNA polymerase I, Xlenow fragment (Boehringer) incubation is carried out for 30 minutes at 12° C. The reaction is stopped by heating at 90° C. for 3 minutes and the mixture is stored at −80° C. until required for further processing.

In an analogous manner the kinased fragments 1/58 and 46/64 are reacted to form duplex I (fragment F$_1$ of the desulphatohirudin gene).

Duplexes I and II have the following structures:

Duplex I

CTCGGAATTCATGCTTGTTTACAC-
CGACTGCACCGAATCTGGTCAGAAC-
CTCTGCCTGTGCCGAACGTTC CACCTTAAG-
TACCAAAAAATGTGGCTGACGTGGCTTAGAC
CAGTCTTGGACACGGACACGCTTCCAAG

TAACGTTTCCGGTCAGCCTAACAATG-
CATCCTCGGTTCTG ATTGCAAACGCCAGTC-
CCATTGTTTACGTAGGACCCAAGAC

Duplex II

CATCCTGGGTTCTGACGGTGAAAAAAAC-
CAGTGCGTTACCGGTCAAGGTAC-
CCCGAAACCGCAGTCTC GTAGGACCCAA-
GACTGCCACTTTTTTTGGTCACGCAATGGCC
ACTTCCATGGGGCTTTGGCGTCAGAG

ACAACGACGGTGACTTCGAAGAAATC-
CCGGAAGAATACCTGCACTAGGATCCTG TGT-
TGCTGCCACTGAAGCTTCTTTACGCCCT-
TCTTATGGACGTCATCCTAGGAC

The manufacture of the fragments $F_1$ and $F_2$ of the desulphatohirudin gene is illustrated in the following scheme 1:

solution is heated for 3 minutes at 90° C. and cooled within 5 minutes to 12° C. After the addition of 8 $\mu$l of Endo-R buffer (cf. Example 8), 20 $\mu$l of deoxynucleoside triphosphate mixture (dATP, dCTP, dGTF, TTP, in each case 0.002 molar, adjusted to pH 7.0 with $NH_3$) and 2 $\mu$l (10 units) of DNA polymerase I, Klenow fragment (Boehringer) incubation is carried out for 30 minutes at 12° C. The reaction is stopped by heating from 3 minutes at 90° C. and the DNA is isolated, after extraction with phenol/chloroform, by precipitation with ethanol. The resulting DNA mixture is dissolved in 100 $\mu$l of ligase/buffer (66 mM tris.HCl pH 7.5, 6.6 mM $MgCl_2$, 10 mM dithiothreitol, 5 mM ATP), 50 units (2 $\mu$l) of $T_4$ DNA ligase (Biolabs) are added and the whole is incubated for 20 hours at 20° C. The reaction is stopped by heating for 5 minutes at 70° C. and the DNA, after extraction with phenol/chloroform, is isolated by precipitation with ethanol. After separating the mixture on an 8% polyacrylamide gel (denaturating) by electrophoresis, the ligation product with 217 base pairs is electroeluted, concentrated on a DE52 cellulose column and, after elution, isolated by precipitation with ethanol.

The desulphatohirudin gene has the following structure

CTGGAATTCATGGTTGTTTACACCGACT-
GCACCGAMTCTGGTCAGAMCCTGIGCCT-

Scheme 1
Manufacture of the fragments $F_1$ and $F_2$ of
the desulphatohirudin gene HV1 and of $F_1$–$F_2$ DNA

```
    1/58                           96/67
         46/64                         154/64
    ┌─────────────┐              ┌─────────────┐
    │T4-polynucleotide-│         │T4-polynucleotide-│
    │   kinase        │          │    kinase       │
    │  annealing      │          │  annealing      │
    └──────┬──────────┘          └──────┬──────────┘
           ▼                            ▼
       [======]                     [======]
    ┌─────────────┐              ┌─────────────┐
    │DNA polymerase I│           │DNA polymerase I│
    │ (Klenow), dNTPs│           │ (Klenow), dNTPs│
    └──────┬──────────┘          └──────┬──────────┘
           ▼                            ▼
       [==========]                 [==========]
       ↑          ↑                 ↑          ↑
     EcoRI      EcoRII           EcoRII       BamHI Fragment F1                  Fragment F2
       (subcloning)                 (subcloning)
         EcoRII                       EcoRII
           ▼                            ▼
       [==========]                 [==========]
       ↑          ↑                 ↑          ↑
     EcoRI      EcoRII           EcoRII       BamHI annealing
                   T4 DNA ligase
                       ▼
           [===========================]
           ↑             ↑            ↑
         EcoRI         EcoRII       BamHI F1–F2-DNA (desulphatohirudin gene)
```

EXAMPLE 9

Polymerisation and Ligation of the Fragments 1/58, Kinased 46/64, Kinased 96/67, and 154/64; Manufacture of the Desulphatohirudin HV1 Gene In each case 50 pmol of fragment 1/58, kinased 46/64, kinased 96/67 and 154/64 are dissolved in 48 $\mu$l of water, the

GTCCGAAGGT GACCTTAAGTACCAACAAAT-
GTGGCTGACGTGGCTTAGACCAGTCTTGGAC
ACCGACACCCTTCCA

TCTAACGTTTGCCGGTCAGGGTAA-
CAAATGCATCCTGGGTTCTGACGGT-
GAAAAAAACCAGTGCGTT AGATTGCAAACGC-

CAGTCCCATTGTTTACGTAGGACCCAAGACT
GCCACTTTTTTTGGTCACGCAA
ACCGGTGAAGGTACCCCGAAACCG-
CAGTCTCACAACGACGGTGACTTCGAA-
GAAATCCCGGAAGAA TGGCCACTTC-
CATGGGGGCTTTGGCGTCAGAGTGTTGCTGC
CACTGAAGCTTCTTTAGGGCCTTCTT
TACCTGCACTACCATCCTG ATGGACGTCATC-
CTAGGAC

The manufacture of.the desulphatohirudin gene from the four fragments is illustrated in the following scheme 2:

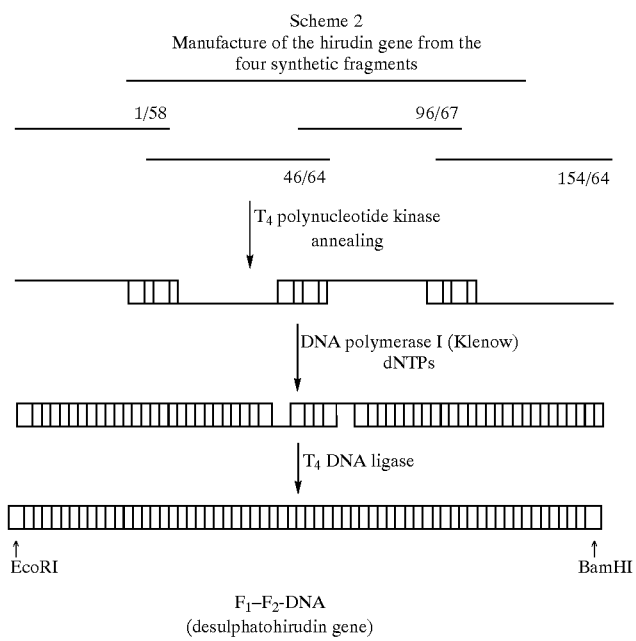

Scheme 2
Manufacture of the hirudin gene from the four synthetic fragments $F_1$–$F_2$-DNA
(desulphatohirudin gene)

EXAMPLE 10

Construction of the Plasmid pML 300 containing the $F_1$-DNA of the Desulphatohirudin HV1 gene
(FIG. 1)

a) Manufacture of the Linearised Vector pBR322/EcoRI/PvuII.

5 pg of pBR322 plasmid DNA are digested with 5 units of PvuII restriction endonuclease (Biolabs) in 200 ml of a solution of 100 µg/ml of gelatin for 1 hour at 37° C. Subsequently this solution is adjusted to 100 mM tris.HCl (pH 7.5), 50 mM NaCl and the DNA is digested with 30 units of EcoRI restriction endo-nuclease (Biolabs) for 2 hours at 37° C. The solution is then adjusted to 50 mM tris-HCl pH 8 and, at a DNA concentration of 10 µg/µl, incubated with 2 units of intestinal alkaline calf phosphatase (Boehringer) for 30 mins at 37° C. The enzyme is inactivated by heating the solution for 60 minutes at 65° C. The solution is then standardised with TNE, extracted with 1 volume of phenol and chloroform, and the digested DNA is precipitated with 2 volumes of alcohol at −20° C. overnight.

The vector (pBR322/EcoRI/PvuII, 2297 base pairs) excised from the pBR322 DNA is separated from the small DNA fragment (2067 base pairs) by gel electrophoresis on 1% low-melting agarose (Biorad) in tris-acetate-EDTA buffer pH 8. After staining the DNA in the agarose gel with EtBr, the area of the gel that contains the DNA band of the pBR322/EcoRI/PvuII vector (=2297 base pairs) is cut out of the gel and liquefied for 10 minutes at 65° C. 20 volumes of TNE are added to this DNA solution, the DNA is purified in accordance with Mueller et al. [J. Mol. Biol. 124, 343, (1978)] by DE-52 chromatography, extracted with phenol/chloroform and the DNA is precipitated with alcohol at −20° C. overnight. The DNA precipitate is dissolved in 50 µl of 0.01M tris.HCl (pH 8), 0.1 mM EDTA, and stored at −20° C. until required for use. 1.4 µg (=3.2 pmol of ends) of DNA are obtained.

b) Manufacture of $F_1$-DNA/EcoRI 24 ng (=1.3 µmol of ends) of the chemically synthesised $F_1$-DNA (see Example 8) are digested with 5 units of EcoRI restriction endonuclease (Biolabs) in 50 µl of 100 mM tris.HCl (pH 7.5), 50 mM NaCl and 100 µg/ml gelatin for 30 minutes at 37° C. Subsequently, 0.06 µg (=0.14 pmol of ends) of the linearised vector pBR322/EcoRI/PvuII (Example 10a) are added to the solution. The enzyme is then, by heating at 65° C., inactivated after 10 minutes, and the solution is standardised with TNE and extracted with phenol/chloroform. The DNA is precipitated with alcohol. The precipitated DNA is stored under alcohol at −20° C. until further processing.

c) Ligation of pBR322/EcoRI/PvuII Vector DNA with $F_1$-DNA/EcoRI and Construction of Plasmid pML300

The DNA precipitate obtained in Example 10b), which contains the two mentioned DNA fragments, is dissolved in 20 µl of a solution of 50 mM tris.HCl (pH 7.8), 10 mM MgCl$_2$, 10 mM DTT, 0.5 mM ATP, and 100 µg/l gelatin and treated with 25 units/µl $T_4$ DNA ligase (Biolabs) at 15° C. for 3 hours. In this manner the recombinant plasmid pML300, which contains the $F_1$-DNA, is obtained in the solution.

d) Transformation of E. coli HN101 with Plasmid pML300

The E. coli HB101 cells pretreated with calcium that are required for the transformation are produced as described by Mandel et al. [J. Mol. Biol. 53, 159 (1970)].

The solution obtained in c), which contains the recombinant plasmid pML300, is heated at 65° C. for 10 minutes in order to inactivate the $T_4$ DNA ligase and is then cooled to 37° C. 10 µl of this reaction mixture are added to 150 µl of calcium-treated E. coli HB101 cells in 10 mM MgCl$_2$ and 10 mM tris.HCl (pH 7.5) in a total volume of 200 µl.

Subsequently, this mixture is cooled in ice for 30 minutes, heated for 2 minutes at 42° C. and then left to stand for 50 minutes in 1 ml of L-medium (cf. Example 18) at 37° C. The mixture is then spread out in aliquots of 0.2 ml on 5 agar plates (McConkey Agar, Difco), which contain 60 µg/ml of ampicillin (Serva). The agar plates are then maintained at 37° C. for 16–18 hours. 484 ampicillin-resistant colonies of the transformed E. coli HB101 are obtained.

e) Screening the colonies that contain $F_1$-DNA 470 transformed colonies (Example 10d) are pressed off onto nitrocellulose filter B85 (Schleicher and Schull). In accordance with M. Grunstein and D. S. Hogness [Proc. Natl. Acad. Sci. USA 72, 3961 (1979)] the colonies are lysed and their denatured DNA is fixed on the filter. Subsequently prehybridisation of the filters is carried out in 20 ml (per filter) of 4×SET [=solution of 30 mM tris.HCl (pH 8), 150 mM NaCl, 1 mM EDTA], 0.1% (w/v) Ficoll 400 (Pharmacia), 0.5% SDS, 50 µg/ml denatured calf thymus DNA for 4 hours at 64° C. Subsequently the nitrocellulose filters are treated in 20 ml (per filter) of 5×SET (w/v) Ficoll 400, 0.2% SDS and 50 µg/ml denatured calf thymus DNA for 16 hours at 64° C. with the $^{32}P$ radioactively labelled probe (approximately $10^3$–$10^4$ Cerencov cpm per filter). The oligonucleotide 46/64 complementary (cf. Example 6) is used as probe.

Subsequently, the filters are washed twice in 2×SET, 0.2% SDS at room temperature, then twice in 2×SET, 0.5% SDS at 60° C. (first for 30 minutes, then for 60 minutes). The filters are then dried between 3 MM paper (Whatman) and placed at −80° C. on an X-ray film (Fuji) with an intensifying screen (Ilford) for 1–2 days.

The resulting autoradiogram shows 71 positive colonies (clones) which can be used for further processing, one of which received the designation pML300.

EXAMPLE 11

Construction of Plasmid pML305, Which Contains the $F_2$-DNA of the Desulphatohirudin HV1 Gene (FIG. 2)

a) Manufacture of Linearised Vector pBR322/BamHI/NruI

5 µg of pBR322 plasmid DNA are digested with 30 units of BamHI restriction endonuclease for 30 minutes at 37° C. in a solution of 100 mM NaCl, 6 mM tris.HCl (pH 7.9), 6 mM $MgCl_2$ and 100 µg/ml gelatin. 15 units of PvuII restriction endonuclease are then added to the solution and the solution is digested for 2 hours at 37° C.

The reaction mixture is heated at 70° C. for 10 minutes in order to inactivate the enzyme. Subsequently the two DNA fragments are separated from each other by gel electrophoresis on 1% low-melting agarose in tris-acetate-EDTA buffer, pH 8. (see Example 10a).

The DNA band of the pBR322 BamHI/PvuII vector (=2672 base pairs) is cut out, liquefied, and purified in accordance with Mueller et al.(supra) by DE-52 chromatography. 0.75 µg (=1.5 pmol of ends) of DNA are obtained.

b) Manufacture of $F_2$-DNA/BamHI

25 µg (=1.3 pmol of ends) of chemically synthesised $F_2$-DNA (Example 8) are digested with 16 units of BamHI restriction endonuclease (Biolabs) in 20 µl of 150 mM NaCl, 6 mM tris.HCl (pH 7.9), 6 mM $MgCl_2$ and 100 µg/ml gelatin for 30 minutes at 37° C. 60 ng (=96 nmol of ends) of the linearised vector pBR322/BamHI/PvuII (Example 11a) are then added to the solution, the whole solution is standardised with TNE and extracted with phenol/chloroform, and the DNA is precipitated with 2 volumes of alcohol. The precipitated DNA is stored under alcohol at −20° C. until required for further processing.

c) Ligation of pBR322/BamHI/PvuII Vector DNA with $F_2$-DNA/BamHI and Construction of Plasmid pML305

The DNA precipitate obtained in Example 11b), which contains the two mentioned DNA fragments, is dissolved in 20 µl of a solution of 50 mM tris.HCl (pH 7.8), 10 mM $MgCl_2$, 10 mM DTT, 0.5 mM ATP, and 100 µg/ml gelatine and treated with 15 units/µl $T_4$ DNA ligase (Biolabs) at 15° C. for 3 hours. In this manner the recombinant plasmid pML305, which contains $F_2$-DNA, is obtained in the solution.

d) Transformation of E. coli HB101 with plasmid pML305

The transformation of the calcium-treated E. coli HB101 cells is carried out as described in Example 10d). 10 µl of the reaction mixture obtained in Example 11c) are used. 313 ampicillin-resistant colonies are obtained.

e) Screening the colonies that contain $F_2$-DNA 65 transformed colonies (Example 11d) are examined for $F_2$-DNA in the manner described in Example 10e). The oligonucleotide 154/64 complementary (cf. Example 6) is used as radioactive probe. 2 positive colonies are obtained in the autoradiogram, one of which is designated pML305.

EXAMPLE 12

Characterisation of Clones pML300 and pML305

The DNAs of recombinant plasmids pML300 and pML305 are isolated in accordance with Ish-Horowitz [Molecular Cloning, A laboratory Manual (ed. T. Maniatis et al.), Cold Spring Harbor Lab., 1982, p. 368]. The nucleotide sequences of the $F_1$-DNA and $F_2$-DNA inserts are ascertained in accordance with Maxam and Gilbert [Proc. Natl. Acad. Sci. USA 74, 560 (1977); see also Leth. Enzym. 65,.499(1980)].

For this purpose, in each case 10 µg of plasmid DNA of pML300 are cleaved with EcoRI restriction endonuclease and 10 µg of plasmid DNA of pML305 are cleaved with BamHI restriction endonuclease and the linearised DNAs are isolated by gel elution from agarose gel [cf. Example 10a)]. Subsequently the isolated DNAs are digested with alkaline phosphatase and chromatographed over DE-52 (cf. Example 11a). The DNAs are then radioactively labelled at the 5'-end with $[\gamma\text{-}^{32}P]ATP$ (specific activity 5000 Ci/mmol, Amersham) and $T_4$ polynucleotide kinase (P-L-Biochemicals).

The radioactively labelled DNAs are then cleaved with a second restriction endonuclease (EcoRII). The resulting DNA fragments are isolated by gel elution from agarose. In the case of pML300 the nucleotide sequence of $F_1$-DNA is then determined from the EcoRI/EcoRl* fragment (approximately 109 base pairs) and in the case of pML300 that of $F_2$-DNA is determined in the EcoRII-BamHI* fragment (approximately 122 base pairs). (* indicates the DNA end that is radioactively labelled).

The nucleotide sequences that are determined for $F_1$-DNA and $F_2$-DNA are identical to those illustrated in Example 8.

EXAMPLE 13

Construction of Expression Plasmid pML310 a) Construction of Linearised Vector pHRi148/EcoRI/BamHI, Which Contains the trp Promotor-operator (FIG. 3 and FIG. 4)

A. Construction of Plasmid p159

10 µg of plasmid $pBRH_{trp}$ [DE-OS 3 111 405] are cleaved with 50 units of EcoRI (Biolabs) for 60 minutes at 37° C. and the digestion mixture, after phenol extraction, is fractionated on a saccharose density gradient (5–23%) in 50 mM tris.HCl (pH 8.0), 1 mM EDTA in a TST41 (Kontron AG) rotor. The centrifugation lasts for 14 hours at 40,000 revs/min and 15° C. 0.3 ml fractions are collected with an ISCO gradient collector at 1 ml/min. The fractions that contain the smaller fragment are combined, the solution is standardised with TNE and precipitation is effected with 2 volumes of ethanol at −20° C. After centrifugation in an Eppendorf centrifuge, the DNA is dissolved in 100 $\mu$l of 10 mM tris.HCl pH 7.5, 0.5 mM EDTA. 5 $\mu$g of this DNA fragment are cleaved with 5 units of BglII (Biolabs) for 60 minutes at 37° C. The reaction mixture is extracted with phenol and chloroform and the DNA is incubated with 2 volumes of ethanol at −80° C. for 10 minutes; the DNA is collected by centrifugation and dissolved again in 50 $\mu$l of 50 mM tris.HCl (pH 8.0). 2 $\mu$l of this solution are removed (0.2 $\mu$g of DNA) and incubated at a DNA concentration of 10 ng/$\mu$l in 50 mM tris.HCl (pH 8.0) with 1 unit of intestinal alkaline calf phosphatase (Boehringer) for 30 minutes at 37° C. The enzyme is inactivated by heating the solution for 60 minutes at 65° C. 0.04 $\mu$g of DNA is removed and incubated 5'-terminally with 10 $\mu$Ci [$\gamma$-$^{32}$P]-ATP (5000 Ci/mmol, Amersham) and 5 units of $T_4$ polynucleotide kinase (P-L Biochemicals) in 20 $\mu$l of reaction volume in 50 mM tris.HCl (pH 9.5), 10 mM $MgCl_2$, and 5 mM DTT, for 30 minutes at 37° C. The radioactive sample is mixed with the non-labelled sample (see above) and the DNA fragments are fractionated by a 5–23% saccharose density gradient in 50 mM tris.HCl (pH 8.0), 1 mM EDTA in a TST60 rotor. The centrifugation is carried out for 5 hours at 60,000 revs/min and 15° C. 0.2 ml fractions are collected. The radioactivity of each fraction is determined by measuring the Cerencov radiation and the fragments are thereby identified. The desired fractions, which contain the small DNA fragment, are combined, the DNA is precipitated with 2 volumes of ethanol and, after centrifugation, is dissolved again in 20 $\mu$l of 10 mM tris.HCl pH 7.5, 0.5 mM EDTA.

The $^{32}$P-labelled EcoRI-BglII DNA fragment is partially cleaved with 0.2 units of TaqI (Biolabs) in 50 $\mu$l volume for 10 minutes at 37° C. The reaction mixture is adjusted to 0.2% SDS, 10% glycerin, 10 mM EDTA, 0.05% bromophenol-blue, and the DNA fragments are separated on a 6% polyacrylamide gel in tris-borate-EDTA [A. C. Peacock et al., Biochemistry 6, 1818 (1967)]. The Band containing the desired EcoRI-TaqI (the largest partial fragment) is identified on the auto-radiogram. This fragment (L. see FIG. 3) is extracted from the gel and purified [W. Müller et al., supra] and dissolved in 10 $\mu$l of 10 mM tris.HCl pH 7.5, 1 mM EDTA. in 10 $\mu$l of 10 mM tris.HCl pH 7.5, 1 mM EDTA.

There is used as acceptor plasmid pBR322, which is cleaved with ClaI and EcoRI: 2 $\mu$g of pBR322 are digested with 4 units of ClaI (Biolabs) in 20 $\mu$l of reaction volume for 60 minutes at 37° C. The protein is extracted with phenol and the DNA is then precipitated with 2 volumes of ethanol at −80° C. for 10 minutes. The DNA is collected by centrifugation and then digested with 10 units of EcoRI (Biolabs) for 30 minutes at 37° C. in 20 $\mu$l of reaction volume. Subsequently, 2 volumes of 0.1M tris.HCl (pH 8.7) are added to the solution and the whole is incubated with 1 unit of alkaline calf phosphatase (Boehringer) at 37° C. for 30 minutes. The phosphatase is then inactivated by incubation at 65° C. for 60 minutes. 100 ng of the acceptor plasmid are incubated with 5 $\mu$l of fragment L-DNA in 15 $\mu$l of reaction volume in 10 mM $MgCl_2$, 20 mM tris.HCl (pH 7.8), 10 mM DTT, 0.5 mM ATP with 30 units per $\mu$l of reaction volume of $T_4$ DNA ligase (Biolabs) for 2 hours.

5 $\mu$l of this solution are added to a mixture that contains 150 ml of *E. coli* HB101 cells treated with calcium chloride (supra) in 10 mM $MgCl_2$, 10 mM $CaCl_2$ and 10 mM tris.HCl (pH 7.5) in a total volume of 200 $\mu$l. The mixture is cooled for 20 minutes in ice, heated for 1 minute at 42° C. and incubated for 10 minutes at 20° C. 1 ml of tryptone medium [tryptone medium contains 10 g of bacto-tryptone (Difco); 1 g of yeast extract (Difco); 1 g of glucose; 8 g of NaCl and 294 mg of $CaCl_2.2H_2O$ in 1 liter of distilled water] is added and the mixture is incubated for 30 minutes at 37° C. while agitating at 300 revs/min. The mixture is plated on two agar plates (McConkey Agar, Difco; 0.6 ml/plate), supplemented with 50 $\mu$g/ml of ampicillin (Sigma). The plates are incubated for from 12 to 17 hours at 37° C.

The plasmid DNA of 10 different colonies is isolated as follows:

The colonies are, as above, used for inoculation of 10 ml of tryptone medium supplemented by 50 $\mu$g/ml of ampicillin, in a 25 ml Erlenmeyer flask. The cultures are agitated for from 15 to 18 hours at 37° C. and 300 revs/min. The cells are harvested by centrifuging (Sorval, HS-4 rotor, 10 minutes at 4000 revs/min., 4° C.). Approximately 0.1 g of cells are obtained, and these are resuspended in 1 ml of 50 mM tris.HCl (pH 8.0). 0.25 ml of lysozyme solution [10 mg/ml in 50 mM tris.HCl (pH 8.0); lysozyme is marketed by Sigma] are added and, after incubation for 10 minutes at 0° C., 0.15 ml of 0.5 mM EDTA (pH 7.5) are added. After a further 10 minutes at 0° C., 60 $\mu$l of 2% Triton X-100 (Merck) are added. After 30 minutes at 0° C. the sample is centrifuged for 30 minutes at 15,000 revs/min and 4° C. in a Sorval SA-600 rotor. The supernatant is deproteinated with 1 vol. of phenol (saturated with TNE). The phases are separated by centrifuging (Sorval HB-4 rotor) for 10 minutes at 5000 revs/min and 4° C. The upper phase is extracted twice with 1 vol. of chloroform. Pancreatic RNAse A (Sigma; 10 mg/ml in TNE preheated for 10 minutes at 85° C.) is added until a final concentration of 25 $\mu$g/ml is reached and the mixture is incubated for 40 minutes at 37° C. The solution is then adjusted with 1M NaCl and 10% polyethylene glycol 6000 (Fluka, treated for 20 minutes at 120° C. in an autoclave) and incubated for 2 hours at −10° C. The precipitate is collected in a Sorval HB-4 rotor (20 minutes at 10,000 revs/min., 0° C.) and dissolved again in 100 $\mu$l of TNE. The DNA solution is extracted with 1 volume of phenol and the DNA is precipitated with 2 volumes of ethanol for 10 minutes at −80° C. The precipitate is collected by centrifuging in an Eppendorf centrifuge and the DNA is dissolved again in 20 $\mu$l of 10 mM tris.HCl (pH 7.5) and 0.5 mM EDTA. 8 to 10 $\mu$g of plasmid DNA are obtained from a 10 ml culture.

The plasmid DNAs are analysed after digestion with the following restriction enzymes:

In each case 0.5 $\mu$g of plasmid DNA is cleaved with HpaI (Biolabs) and with HpaI (Biolabs) and EcoRI (Biolabs) with ClaI (Biolabs) according to standard directions, in accordance with the instructions of the enzyme manufacturer. The DNAs are fractionated on a 1% agarose gel in 40 mM tris.acetate (pH 7.8), 1 mM EDTA and 0.5 $\mu$g/ml ethidium bromide. The desired plasmids contain an HpaI site and, after digesting 3 times, yield in addition to the large DNA fragment 2 smaller fragments which are larger than the small EcoRI-ClaI fragment of pBR322. One of these plasmids is designated p159 (see FIG. 3).

B. Construction of plasmid pHRi145

2 $\mu$g of p159 DNA are digested with 10 units of EcoRI (Biolabs) for 30 minutes at 37° C. The DNA is extracted with phenol, precipitated with ethanol and, after centrifugation, dissolved in 10 $\mu$l of 10 mM tris.HCl (pH 7.5), 0.5 mM EDTA. The DNA digested with EcoRI is furthermore treated with 5 units of DNA polymerase (Klenow fragment) (Boehringer) in 10 mM $MgCl_2$, 10 mM β-mercaptoethanol, 50 mM NaCl, 0.1 mM dATP (P&L Biochemicals), 0.1 mM dTTP (P&L Biochemicals) for 15 minutes at 12° C. The polymerase is then inactivated by incubation at 85° C. for 5 minutes. The reaction mixture is diluted in 20 mM tris.HCl (pH 7.8), 10 mM $MgCl_2$, 10 mM DTT, 0.5 mM ATP (Sigma) by a factor of 10 and incubated with 30 units of $T_4$ DNA ligase per μl of reaction mixture for 1 hour at 15° C.

50 ng of the DNA are transformed in E. coli (in the manner described above) and plated out on McConkey agar plates supplemented with 50 μg/ml ampicillin.

The plasmid DNAs of 10 different colonies are isolated in the manner described above. The plasmid DNAs are analysed by digesting with EcoRI. The desired plasmids are EcoRI-resistant. The analysis is carried out in the manner described above. One of the desired plasmids is designated HRi145 (FIG. 3).

C. Construction of Plasmid pHRi148

2 μg of pHRi145-DNA are treated with 5 units of ClaI (Boehringer) for 60 minutes at 37° C., then deproteinated by means of phenol extraction. The DNA is precipitated with ethanol and then dissolved in 20 μl of 10 mM tris.HCl (pH 7.5), 0.5 mM EDTA. The projecting ends are, as described above, made up with DNA polymerase I (Klenow fragment), except that dATP and dTTP are replaced by dCTP (P&L Biochemicals) and dGTP (P&L Biochemicals). The polymerase is inactivated by incubation at 85° C. for 5 minutes. 2 volumes of 0.1M tris.HCl (pH 8.7) are added to the reaction mixture which is incubated with 0.5 units of calf phosphatase (Boehringer) for 30 minutes at 37° C. The reaction mixture is deproteinated by extraction with phenol. The DNA is precipitated with ethanol and dissolved in 8 μl of 10 mM tris.HCl (pH 7.5), 0.5 mM EDTA.

A chemically synthesised DNA linker of the formula

5'-GAATTCCATGGTACCATGGAATTC-3' is phosphorylated at the 5' end by incubating 8 pmol of the linker with 5 μCi [γ-$^{32}$P]-ATP (5500 Ci.mmol$^{-1}$ Amersham) in 8 μl of reaction volume that contains 0.1 mM rATP (Sigma), 50 mM tris.HCl (pH 9.5), 10 mM $MgCl_2$, 5 mM DTT and 2 units of $T_4$ polynucleotide kinase (P&L Biochemicals) for 30 minutes at 37° C. The reaction is stopped by freezing at −80° C.

The radioactively labelled linker is then treated with 1 μg of ClaI and phosphatase and ligated with pHRi145-DNA (see above) in a 20 μl reaction volume that contains 0.5 mM rATP (Sigma), 10 mM DTT (Calbiochem), 20 mM tris.HCl (pH 7.8), 1 mM $MgCl_2$ and 800 units of $T_4$ DNA ligase (Biolabs). The incubation is carried out for 2 hours at 15° C. The ligase is inactivated by incubation at 85° C. for 10 minutes. Subsequently, 2 volumes of water are added, the sodium chloride concentration is adjusted to 10 mM and 20 units of KpnI (Biolabs) are added over 30 minutes at 37° C. After extraction with phenol and chloroform, the mixture is fractionated through 0.9% low-melting agarose gel (Biorad) in 40 mM trisacetate (pH 7.8), 1 mM EDTA and 0.5 μg/ml ethidium bromide. The band, visible by UV radiation, that demonstrates the same mobility as a marker DNA of the same size is cut out with a scalpel. The portion of gel is melted for 5 minutes at 65° C. and then cooled to 37° C. A volume of approximately 20 μl is obtained. 5 μl of this solution are removed and incubated for 12 hours at 15° C. with 400 units of $T_4$ ligase (Biolabs) in 10 μl of reaction volume, which has been adjusted to 0.5 mM ATP, 10 mM DTT, 10 mM $MgCl_2$, 20 mM tris.HCl (pH 7.8). 1/10 volume of a solution with 100 mM tris.HCl (pH 7.5), 100 mM $CaCl_2$ and 100 mM $MgCl_2$ are added to the ligase mixture (solidified at 15° C.) and the whole is incubated at 65° C. for 5 minutes. The solution is then used to transform calcium-treated E. coli HB101 cells in the manner described above. Plating out on McConkey Agar plates supplemented with 50 μg/ml ampicillin is carried out.

The plasmid DNAs of 10 different colonies are isolated in the manner described above, and the DNA is subjected to the following restriction enzyme analysis: In each case 0.5 μg of plasmid DNA is cleaved in succession with KpnI (Biolabs), NcoI (Biolabs) and EcoRI (Biolabs) in accordance with the instructions of the enzyme manufacturer. The cleavage products are fractionated on 1% agarose gels in 40 mM tris.acetate (pH 7.8), 1 mM EDTA, 0.5 μg/ml ethidium bromide. All plasmids exhibit one of these enzyme cleavage sites each, as desired. One is designated HRi148.

The plasmid HRi148 contains a tryptophan promoter-operator and a ribosomal binding site up to and including ATG. Hirudin and also other heterologous genes can be coupled directly by way of the EcoRI, NcoI, KpnI sites occurring once in the plasmid. Furthermore, this construction renders possible direct coupling and expressing of heterologous genes without the ATG necessary for the initiation of translation having to be present on the corresponding gene. This can easily be achieved by cleaving with NcoI and making up the projecting ends with DNA polymerase I, in the manner described, or by cleaving with KpnI and removing the projecting ends by nuclease $S_1$. The plasmid HRi148 is thus an expression plasmid with broad application.

D. Manufacture of the Linearised Vector pHRi148/EcoRI/BamHI

5 μg of plasmid DNA of pHRi148 are digested with the restriction endonucleases EcoRI and BamHI. The excised vector pHRi148/EcoRI/BamHI is isolated by means of density gradient centrifugation.

b) Manufacture of $F_1$-DNA/EcoRI/EcoRII and $F_2$-DNA/BamHI/EcoRII

I. Manufacture of $F_1$-DNA/EcoRI/EcoRII

5 μg of plasmid DNA of pML 300 are first digested with 10 units of EcoRI restriction endonuclease in 50 μl of a solution of 100 mM tris.HCl (pH 7.5), 50 mM NaCl and 100 μg/ml gelatine for 1 hour at 37° C. An aliquot (0.5 μg) of this linearised plasmid DNA/EcoRI is isolated by gel elution from an agarose gel (cf. Example 10a)) and radioactively labelled with [γ-$^{32}$P]ATP (cf. Example 12). The main amount of the plasmid DNA/EcoRI is then mixed with this radioactively labelled DNA, digested with EcoRII restriction endonuclease and the EcoRII-EcoRI* DNA fragment (109 base pairs) is separated by gel electrophoresis on 8% polyacrylamide. 200 μg of $F_1$-DNA/EcoRI*/EcoRII are isolated by gel elution.

II) Manufacture of $F_2$-DNA/BamHI/EcoRII

5 μg of plasmid DNA of pML 305 are cleaved with 10 units of BamHI restriction endonuclease. An aliquot (0.5 μg) of this linearised plasmid DNA/BamHI is isolated by gel elution from an agarose gel (cf. Example 10a)) and radioactively labelled with [γ$^{32}$P] (cf. Example 12). The main amount of the plasmid DNA/BamHI is then mixed with this radioactively labelled DNA, digested with EcoRI restriction endo-nuclease and the EcoRII-BamHI* DNA fragment (122 base pairs) is separated by gel electrophoresis on 8% poly-acrylamide. 250 μg of the $F_2$D DNA/BamHI*/EcoRII are isolated.

c) Ligation of $F_1$-DNA with $F_2$-DNA and Construction of the Expression Plasmid pML310

10 ng (=473 nmol of ends) of $F_1$-DNA/EcoRI/EcoRII and 9 ng (=495 nmol of ends) of $F_2$-DNA/BamHI/EcoRII are treated in a volume of 20 μl with T₄ DNA ligase in the manner already described in Example 10c). Subsequently, the mixture is extracted with phenol/chloroform and the DNA is precipitated with alcohol. The DNA precipitate is then dissolved as described in Example 10c) and digested with EcoRI and BamHI restriction endonuclease. The solution is then standardised with TNE and 30 ng (=50 nmol of ends) of the vector DNA pHPi148/EcoRl/BamHI (cf. Example 13aD) are added. Subsequently, the solution is again extracted with phenol/chloroform and the DNA is precipitated with alcohol. The precipitated DNA mixture is treated in the manner indicated in Example 10c) with T₄ DNA ligase (Biolabs). In this manner, there is produced in the solution a recombinant plasmid that contains as insert $F_1$-$F_2$-DNA (desulphatohirudin gene).

d) Transformation of *E. coli* HB101 with Plasmid pML310

The transformation of *E. coli* HB101 cells treated with calcium is carried out in the manner described in Example 10d). 10 μl of the reaction mixture obtained in Example 13c) are used. 420 ampicillin-resistant colonies are obtained.

e) Screening the colonies that contain $F_1$-$F_2$-DNA 18 transformed colonies (Example 13d) are examined for their $F_1$-$F_2$-DNA content in the manner described in Example sne). A mixture of the oligodeoxynucleotides described in Examples 5 and 6 is used as radioactive probe. In the autoradiogram 12 positive colonies are obtained, five of which are designated pmL310, pML311, pML312, pML313, pML314.

EXAMPLE 14

Characterisation of the Clone pML310

The characterisation of the $F_1$-$F_2$-DNA sequence in the recombinant plasmid pML310 is effected by sequencing the $F_1$-$F_2$-DNA according to Maxam and Gilbert (supra) in the manner described in Example 12. 10 μg of plasmid DNA are examined. The nucleotide sequence of the $F_1$-$F_2$-DNA is identical to that described for the synthetic desuophatohirudin gene.

EXAMPLE 15

Expression of Desulphatohirudin HV in Yeast

The chemically synthesized gene for hirudin is amplified as a 206 bp EcoRl-BamHI insert in plasmid pML310 (see example 14). The gene is excised from the plasmid and expressed in yeast under the control of the repressible PHO5 promoter. The construction includes the 541 bp PHO5 promoter sequence and the complete PHO5 signal sequence (51 nucleotides coding for 17 amino acids) as described in European Patent Application No. 143,081. This sequence is fused in frame to the mature coding sequence of hirudin which starts with the codon for valine as the $NH_2$-terminal amino acid of natural mature hirudin. The hirudin gene is flanked at its 3' end by a DNA fragment providing the PHO5 transcription termination signals. The vector part of the expression plasmid contains yeast 2μ sequences, the yeast LEU2 gene for selection in yeast and the ampicillin resistance gene and the *E. coli* origin of replication for selection and amplification in *E. coli*. The procedure is illustrated in FIGS. 5, 6 and 7.

Adjustment of the Nucleotide Sequence at the 5' End of the Desulphatohirudin Gene The nucleotide sequence coding for desulphatohirudin starts with GTT which stands for the $NH_2$-terminal valine in the final gene product. For convenient subcloning and expression in *E. coli* the coding sequence has been extended at the 5' end by eight nucleotides including an EcoRI restriction site and an ATG initiation codon. For the exact in frame fusion of the hirudin coding sequence to the sequence coding for the PHO5 signal peptide these additional nucleotides have to be removed. This is achieved by converting the EcoRI restriction site to a flush end site, adding a synthetic oligonucleotide containing a HgaI recognition site in such a position that subsequent cleavage with HgaI occurs immediately upstream of the GTT codon.

Introduction of a HgaI Restriction Site in Front of the Desulphatohirudin Gene (cf. FIG. 5)

8 μg of plasmid pML310 (see Example 13c) are digested to completion with restriction endonuclease EcoRI. The DNA (pML310/EcoRI) is extracted with phenol/chloroform and precipitated with ethanol. 5' overhanging ends are removed by nuclease $S_1$. 4 μg of pML310/EcoRI DNA are digested in 100 μl of 250 mM NaCl, 1 mM $ZnSO_4$, 30 mM sodium acetate pH 4.6 and 20 U/ml of nuclease $S_1$ (Sigma) for 45 min at 37° C.

The DNA is extracted with phenol/chloroform and precipitated by ethanol. The DNA (pNL310/EcoRI/$S_1$) is resuspended in 100 μl of 50 mM Tris.HCl pH 8.0 and incubated with 2 units of calf intestine alkaline phosphatase (CIAP, Boehringer) for one hour at 37° C. The enzyme is inactivated at 65° C. for 1.5 hours.

The NaCl concentration in the incubation mixture is adjusted to 150 mM. The dephosphorylated DNA (pML310/EcoRI/$S_1$/CIAP) is purified by adsorption to a DE52 (Whatman) ion exchange column in a low salt buffer (150 mM NaCl, 10 mM Tris.HCl pH 8.0, 1 mM EDTA) and then eluted with a high salt buffer solution (1.5M NaCl, 10 mM Tris.HCl pH 8.0, 1 mM EDTA). The DNA is precipitated with ethanol and resuspended in $H_2O$ at a concentration of 0.8 mg/ml.

An oligonucleotide of the formula

5'-AGCGTCGACGCT -3' is synthesized by the phosphotriester method [Itakura et al., J. Am. Chem. Soc. 103, 706 (1981)]. The sequence of the oligonucleotide is self-complementary containing the recognition site -GACGC- for restriction endonuclease HgaI. Annealing of two single strands leads to a double-stranded DNA linker of 12 base pairs. 1.2 μg of the synthetic single-stranded oligodeoxynucleotide are phosphorylated in 10 μl of 60 mM Tris.HCl pH 7.5, 10 mM $MgCl_2$, 5 mM DTT, 30 μCi of [γ-³²P] ATP (3000 Ci.mmol⁻¹ Amersham) and 6 units of $T_4$ polynucleotide kinase (Boehringer) for 30 min at 37° C., followed by a 15 min chase at 37° C. in the presence of 0.5 mM ATP. The mixture is further incubated for 10 min at 75° C. to inactivate the enzyme and is then allowed to cool to room temperature for annealing.

0.6 μg (170 pmoles)of the ³²P-labelled linker DNA are mixed with 2.4 μg (1.75 pmol ends) of pML310/EcoRI/$S_1$/CIAP and ligated in 20 μl of 60 mM Tris.HCl pH 7.5, 10 mM $MgCl_2$, 5 mM DTT, 3.5 mM ATP, 800 units of $T_4$ DNA ligase (Biolabs) for 20 hours at 15° C. The ligase is inactivated at 85° C. for 10 min and the excess of linker molecules is removed by precipitation of the DNA in the presence of 10 mM EDTA pH 7.5, 300 mM sodium acetate pH 6.0 and 0.54 volumes of isopropanol. After 30 min at room temperature the DNA is pelleted, resuspended in 45 μl of ligation mixture (specified above) and ligated for 6 hours at 15° C. to form circular DNA.

Aliquots of 1 μl and 3 μl of the ligation mixture are added to 100 μl of calcium-treated, transformation competent *E. coli* HB101 cells (prepared according to the method of D. Hanahan [J. Biol. Chem. 166,557(1983)]. The cells are left on ice for 30 min, then incubated for 3 min at 42° C., cooled on ice for 2 min and then incubated for one hour at 37° C. in 400 μl of SOC Medium. The cells are concentrated in 100 μl each and plated on LB agar plates containing 50 μg/ml of ampicillin. 12 transformed, amp$^R$ colonies are grown individually in LB medium containing 100 μg/ml of ampicillin. Plasmid DNA is prenarPd according to the method of D. S. Holmes et al. [Anal. Biochem. 114, 193 (1981)]. The presence of the synthetic oligonucleotide linker is confirmed by DNA sequencing using a single stranded DNA fragment as primer which hybridizes to the coding strand of hirudin. One clone which contains the linker DNA at the correct position in front of the hirudin gene is referred to as pML4310L.

EXAMPLE 16

Fusion of the PHO5 Signal Sequence and the Desulphatohirudin Structural Gene a) Isolation of the 0.2 kb Desuldhatohirudin Fragment (FIG. 5)

12 μg of plasmid pML310L are digested to completion with restriction endonucleases BamHI and PvuI. After extraction of the DNA by phenol/chloroform and ethanol precipitation the two restriction fragments are separated on a 1.2% agarose gel in tris-borate-EDTA buffer pH 8.3. The ethidium-bromide stained 0.84 kb PvuI-BamHI fragment is isolated in a gel slice. The DNA is electroeluted in a dialysis bad filled with 3 ml of 0.2×TBE buffer. The closed bag is submersed in TBE buffer pH 8.3 (90 mM Tris-base, 90 mM boric acid, 2.5 mM EDTA). After 30 min at 100 mA the polarity of the current is reversed for 45 sec. to repellthe DNA from the dialysis membrane. The buffer surrounding the gel slice in the dialysis bag is recovered, adjusted to 150 mM NaCl and passed through a DE52 (Whatman) ion exchange column. The DNA is eluted with a high salt buffer (1.5 M NaCl, 10 mM Tris.HCl pH 8.0, 1 mM EDTA), precipitated with ethanol and redissolved in H$_2$O at a concentration of 0.1 mg/ml.

The 0,84 kb PvuI-BamHI fragment of pML310L is further digested with restriction endonuclease HgaI This digest generates a 198 bp HgaI-BamHI fragment which contains the complete coding sequence for mature desulphatohirudin. Additional AluI digestion does not touch the 198 bp HgaI-BamHI fragment butelirinates another HgaI fragment of similar size.

The 0.2 kb HgaI-BamHI fragment is separated from other fragments on a 1.5% agarose gel in TBE buffer and is isolated by electroelution (as described above). The DNA is purified by DE52 ion exchange chromatography and ethanol precipitation. The DNA is resuspended in H$_2$O at a concentration of 30 μg/ml (0.2 pmoles/μl).

b) Isolation of the PHO5 Promoter Region with Part of the PHO5 Signal Sequence (FIG. 6)

Plasmid p31/PHO5-TPA18 (cf. European Patent Application No. 143,081) has the PHO5 promoter and the PHO5 signal sequence fused in frame to a foreign structural gene (t-PA). A 584 bp BamHI-BalI fragment contains the PHO5 promoter and all of the PHO5 signal sequence but eight nucleotides at the 3' end.

8 μg of p31/PHO5-TPA18 DNA are digested with restriction endonuclease BalI (16 hours at 37° C.). The DNA is purified by phenol/chloroform extraction and ethanol precipitation.

The DNA is resuspended in H$_2$O at a concentration of 0.7 mg/ml.

The correct junction between the PHO5 signal sequence and the coding region for desulphatohirudin is provided by a synthetic linker of the formula (1) 5'-CCAATGCA-3'

(2) 3'-GGTTACGTCAACA-5'

Eight nucleotides at the 5' end of the linker (5'-CCAATGCA) represent part of the PHO5 signal sequence from the BalI site to the processing site. The 5' overhanging five nucleotides of oligonucleotide (2) fit into the HgaI cleavage site at the 5' end of the desulphatohirudin coding sequence.

The individual single stranded oligonucleotides (1) and (2) are synthesized by the phosphotriester method (Itakura et al., supra). 1.1 μg and 1.8 μg of oligonucleotides (1) and (2), respectively, are individually phosphorylated at their 5' ends, mixed in equinolar amo unt s and annealed as described in example 15.

1.3 μg (200 pmoles) of the phosphorylated, double stranded linker DNA is ligated to 7 μg (1,8 pmoles) of BalI cleaved p31/PHO5-TPA18 in 40 μl of 60 mM Tris.HCl pH 7.5, 10 mM MgCl$_2$, 3.5 mM ATP, 5 site. DTT and 1400 units of T$_4$ DNA ligase (Biolabs) at 15° C. for 16 hours. The ligase is inactivated for 10 min at 85° C. The excess of linkers is removed by precipitation of the DNA in the presence of 10 mM EDTA, 300 mM sodium acetate pH 6.0 and 0.54 volumes of isopropanol. The DNA is resuspended and further digested with restriction endonuclease BamHI. After extraction of the DNA by phenol/chloroform and ethanol precipitation the two restriction fragments are separated on a 1.2% agarose gel in trisnborate-EDTA buffer pH 8.3. The 0.6 kb fragment is isolated from the gel. The DNA is electroeluted and further purified by DE52 ion exchange chromatography and ethanol precipitation. The 0.6 kb BamHI-HgaI DNA fragment is resuspended in H$_2$O at a concentration of 40 μg/ml.

c) Isolation of a pJDB207 Yeast Vector Fragment (FIG. 6)

9 μg of plasmid pJDB207R/PHO5-TPA (12-2). DNA (cf. European Patent Application No. 143,081) are digested with restriction endonuclease BamHI. Upon complete digestion, th e DNA is extracted by phenol/chloroform and ethanol precipitated. The DNA is resuspended in 50 mM Tris.HCl pH 80 at a concentration of 0.1 mg/ml and digested with 7 units of calf intestine alkaline phosphatase for one hour at 37° C. The phosphatruase is inactivated for 1.5 hours at 65° C. and the DNA is purified by DE52 ion exchange chromatography (see example 15) and ethanol precipitation. The 6.8 kb large BainHI fragment is separated on a 1.2% agarose gel in tris-borate-EDTA buffer pH 8.3. The DNA is electroeluted and purified by DE52 ion exchange chromatography and ethanol precipitation. The DNA is dissolved in H$_2$O at a concentration of 0.4 mg/ml (0.1 pmoles/μl).

d) Ligation of the PHO5 Promoter Fragment and the Desulphatohirudin Structural Gene to the pJDB207 Yeast Vector Fragment (FIG. 6)

The pJDB207 yeast vector, the PHO5 promoter fragment with the PHO5 signal sequence and the desulphatohirudin structural gene are all isolated as DNA fragments (see example 16 a–c) which are ligated to form an expression plasmid. 0.3 pmoles of the 0.6 kb BamHI-HgaI fragment of p31/PHO5-TPA18 and 0.3 pmoles of the 0.2 kb HgaI-BamHI fragment of PML310L are ligated to 0.1 pmoles of a 6.8 kb BamnHI fragment of pJDB207R/PHO5-TPA(12-2) in 10 μl of 60 mM Tris.HCl pH 7.5, 10 mM MgCl$_2$, 5 mM DTT, 1 mM ATP and 400 units of T$_4$ DNA ligase for 20 hours at 15° C.

A one μl aliquot of the ligation mixture is added to 100 μl of transformation competent E. coli HB101 cells prepared according to Hanahan (supra). The transformation protocol is also adopted from this publication. The cells are plated on LB agar plates containing 50 μg/ml of ampicillin.

24 amp$^R$ colonies are grown individually in LB medium with lAsigmle of ampicillin. Plasmid DNA is analysed for size and orientation of the insert by cleavage with restriction endonuclease PstI. A single clone with the correct orientation of the insert is referred to as pJDB207/PHO5-HIR.

EXAMPLE 17

Transformation of *Saccharomyces cerevisiae* Strain GRF18

Plasmid pJDB207/PHO5-HIR is introduced into *Saccharomyces cerevisiae* strain GRF18 (α,his3–11,. his3–15, leu2–3, leu2–112, can$^R$) using the transformation protocol described by Hinnen et al. (supra). 5 µg of plasmid DNA are added to 100 µl of a spheroplast suspension and the mixture is treated with polyethylene glycol. The spheroplasts are mixe d with 10 ml of regeneration agar and plated onto yeast minimal medium plates without leucine.

A single transformed yeast colony is picked and grown in yeast minimal medium without leucine. The colony is referred to as

*Saccharomyces cerevisiae* GRF18/pJDB207/PHO5-HIR.

EXAMPLE 18

Cultivation of *S. cerevisiae* GRF18/pJDB207/PHO5-HIR:

Cells of *S. cerevisiae* GRF18/pJDB207/PHO5-HIR are agitated in 20 ml of yeast minimal medium (Difco Yeast Nitrogen base without amino acids with the addition of 2% glucose and 20 mg/l L-histidine) at 30° C. and cultivated to a cell density of 3×10$^7$ cells/ml. The cells are washed in 0.9% NaCl and then used for inoculating 50 ml cultures in low $P_1$-minimal medium. Low $P_i$-minimal medium is prepared corresponding to the composition of Difco Yeast Nitrogen Base medium (without amino acids), but contains 0.03 g/l $KH_2PO_4$, 1 g/l KCl, and 10 g/l L-asparagine instead of $(NH_4)_2SO_4$, 2% glucose and 1 g/l L-histidine. The cultures are inoculated up to a cell density of 4×10$^6$ cells/ml and agitated at 30° C. for up to 42 hours at 200 revs/min.

EXAMPLE 19

Isolation of the Desulphatohirudin Compounds from *S. cerevisiae* GPF18/pJDB207/PHO5-HIR a) Isolation of Desulphatohirudin Compounds from the Culture Medium A. Enrichment of hirudin compounds on a RP-C18 Column After a fermentation time of 18 h, 26 h and 42 h, respectively, ten samples of 10 ml each are taken from the culture medium and are enriched for proteins by desalting and concentration on a Bond Elut C-18 column (1 ml, Analytichem International). When the samples have been applied to the column and the liquid has been removed in vacuo the column is washed twice with 1.5 ml water-acetonitril (9:1)-0.1% trifluoroacetic acid (9:1). Hirrdin compounds are eluted from the column with water-acetonitril-0.1% trifluoroacetic acid (6:4). 2 ml eluate are concentrated at a Speed Vac concentrator (Savant) to a final volume of 400 µl. The hirudin compounds are identified by HPLC analysis, by comparison with authentic desuephato-hirudin and by means of the thrombin inhibition assay. About 0.2 to 2 µg/ml hirudin compounds are contained in the samples.

B. Ion exchange chromatography on a DEAB cellulose column 1 l of culture medium is harvested after a fermentation time of 42 h and is centrifuged. The supernatant is applied to an anion exchange column with DE53 cellulose (Whatman) at pH 7.5 [conditions: column 2.5×15.5 cm (76 ml); elution buffer A: 20 mM ammonium acetate, 100 mM NaCl, pH 7.5; elution buffer B: 20 mM ammonium acetate, 4M NaCl, pH 5.0; flow : 66 ml/h]. The column is washed with 228 ml buffer A and is then eluted with a linear salt gradient of 228 ml each of buffer A and buffer B, respectively. Fractions of 22 ml are collected. Hirudin compounds are eluted in fractions 71 to 74(88 ml) and are identified by means of the thrombin inhibition assay. The active fractions are dialysed overnight at 4° C. against 20 mM amfonium acetate. Subsequently, aliquots are lyophilised twice. The lyophilisates contain desulphatohirudin compounds as based on reversed phase HPLC.

C. Gel filtration on Sephadex G-50 and final purification by means of HPLC

The main fraction (80 ml of eluate) being active in the thrombin inhibition testais dialysed overnight at 4° C. against 20 mM airinonium acetate pH 7.5 and then concentrated using a rotary evapora tor at 35° C. to a final volume of 5 ml.

The resulting clear aqueous solution is applied to a Sephadex G-50 fine column (Pharmacia) with a bed volume of 160 ml, the column (2.5×64 cm, Biorad) being pre-equilibrated with 5% acetic acid. The main activity contained in 50 ml of eluate (fractions 5–7, flow 50 ml/h, 25 min./fraction) is concentrated using a rotary evaporator and then subjected to a reversed phase HPLC separation. An aliquot (500 µl) of the individual fractions is concentrated 1:10 using a "speed vac" concentrator (Savant) and examined by means of reversed phase HPLC analysis for its content of desulphatohirudin compounds. The solutions contain desulphatohirudin compounds. Fraction 6 (18 ml) contains the smallest percentage proportion of secondary components and is further purified by means of semipreparative reverse phase HPLC.

Experimental conditions: Vydac 218 TP 510 RP-HPLC column, 10×250 mm; aliquot portions of fraction 6 (200 µl concentrated 1:10) per separation; AUFS 0.5 at 220 nm; flow rate: 2 ml/min. Eluant: A: 0.1% trifluoroacetic acid, B: acetonitrile/water 8:2+0.07% trifluoroacetic acid, 1 min. 16% B, then increase in the course of 40 min. to 64% B. The resulting fractions are diluted 1:1 with water and lyophilised. The residue consists of pure desulphatohirudin compounds.

b) Isolation of Desulphatohirudin Compounds from Cell Extract of *S. cerevisiae* GRF18/pJDB207/PHO5-HIR The cells are disintegrated as usual (cf. European Patent Application No. 100,561). The supernatant which has been treated with 2% acetic acid is centrifuged (12,000 rpm, 10° C.). Ammonia is added to a final pH of 7.5 and the slightly opaque solution (50 ml) is further treated as above (cf. example 19a). Hirudin compounds are identified as above, i.e. with the thrombin inhibition assay and by means of reversed phase HPLC.

EXAMPLE 20

Analysis of the Product Mixture from the Fermentation of *S. cerevisiae* GRF18/pJDB207/PHO5-HIR a) A 2 ml aliquot of the supernatant prepared as above (cf. Example 19b) is dried on a "Speed Vac" concentrator under high vacuum. The samples are dissolved individually in 100 µl of water and subjected to HPLC analysis (experimental conditions no.1, see below). The thrombin inhibition of the individual fractions is tested. The fractions with a retention time of 16.5 min and 17.7 min show thrombin inhibition. The ratio (expression yield) of these two fractions is approximately 4:1. According to amino acid composition these fractions are desulphatohirudins.

b) The fractions active in the thrombin inhibition test obtained as described in Example 19a are subjected to HPLC analysis under two different sets of conditions.

Experimental conditions No. 1: Nucleosil (MN) C18, 5 µm RP-HPLC column, 4.6×120 mm: 50 µl hirudin compounds per separation, att. 6 at 214 nm; flow rate 1.2 ml/min.; eluant: A: 0.1% trifluoroacetic acid, B: acetonitrile/water 8:2 with 0.08% trifluoroacetic acid, 2 min. 16% B, then increase in the course of 50 min. to 64% B. Counterpressure: 66 bars.

Experimental conditions No. 2: as above, except: gradient 2 min. 20% B, then increase in the course of 40 min. to 80% B.

Fractions are taken at one minute intervals (a total of 45) and subjected to the thrombin inhibition test. Fractions 17–19 prove active. Furthermore, the amino acid composition, the N-terminus and the N-terminal sequence are determined for the active hirudin compounds of fractions 17 and 18. One fraction (No. 17) is in addition compared with authentic desulphatohirudin, which is obtained by reacting natural hirudin from leeches with the enzyme arylsulphatase. The results are compiled in the following table 1:

TABLE 1

| Fraction | Retention time (min.) Conditions no. 1 | Retention time (min.) Conditions no. 2 | Thrombin inhibition (%) |
| --- | --- | --- | --- |
| Fr. 17 | 16.5 | 13.7 | 96 |
| Fr. 18 | 17.7 | 14.7 | 86 |
| Fr. 19 | 18.7 | — | 78 |
| authentic desulpha-tohirudin | 16.5 | 13.6 | 86 |

The ratio in yield of fractions 17 and 18 is again about 4:1.

c) 200 ml aliquots of the supernatant prepared as above (cf. Example 19a) are subjected to HPLC analysis (conditions Nr. 3 see below) and FPLC separation (conditions Nr. 4). The thrombin inhibition of the individual fractions is tested. The fractions with a retention time of 8.0 min (Peak 1), 11.1 min (Peak 2) and 12.1 (Peak 3) have a strong thrombin inhibition. The ratio (expression yield) of these three compounds is approximately 1:4:1. According to HPLC analysis the compounds corresponding to peaks 2 and 3 are identical with the hirudin compounds described in Example 20b) (fractions 17 and 18). The results are summarized in Table 2:

TABLE 2

| Fraction | Retention time (min) Conditions No 1 | Retention time (min) Conditions No 2 | Retention time (min) Conditions No 3 | [c] NaCl Conditions No 4 |
| --- | --- | --- | --- | --- |
| Peak 1 | 14.0 | 11.6 | 8.0 | 365 mM |
| Peak 2 (Fr. 17) | 16.5 | 13.7 | 11.1 | 340 mM |
| Peak 3 (Fr. 18) | 17.7 | 14.7 | 12.1 | 360 mM |

Experimental conditions No 3: Vydac 218 TP-B5 RP-HPLC column, 4.0×120 mm, 15 µg hirudin compound per separation, att. 7 at 214 nm, flow rate 1.2 ml/min; eluant A: 0.1% trifluoroacetic acid, B: acetonitrile with 0.08% trifluoroacetic acid, 2 min 16% B, then increase in the course of 20 min to 40% B; back pressure 80 bar.

Experimental conditions No 4: Pharmacia Mono Q FPLC anion exchange-column, 5.0×50 mm, 15 µg hirudin compound per separation, AUFS 0.01 at 280 nm, flow rate 1.0 ml/min; gradient elution buffer A: 20 mM Tris-HCl pH 7.5, buffer B: buffer A and 1 M NaCl pH 7.5, 9 min 15% B, then increase in the course of 21 min to 70% B.

EXAMPLE 21

Characterisation of Desulphatohirudin Compounds from the Fermentation of the Strain *S. cerevisiae* GRF 18/pJDB207/PHO5-HIR According to HPLC analysis the hirudin compounds of fractions 17 (or peak 1) and 18 (or peak 2) isolated from the medium (cf. example 20, Tables 1 and 2) are identical to the corresponding compounds isolated from the cell extracts (intracellular hirudin compounds). These compounds as well as the compound of peak 3 (cf. Table 2) are characterised as follows:

a. Determination of the Amino Acid Composition

Approximately 2.5 µg of the pure hirudin compound are hydrolysed for 24 h with 6N HCl at 110° C. and then analysed as described by Chang et al. [DABS-Cl method; Methods in Enzymology 91, 41 (1983)]. The hydrolysate has the following composition:

Peak 1 (cf. Table 2)

| Amino acid | Hydrolysate |
| --- | --- |
| Asp | 9.2 (9) |
| Thr | 4.1 (4) |
| Ser | 4.0 (4) |
| Glu | 12.4 (12) |
| Pro | 3.1 (3) |
| Gly | 9.0 (9) |
| Val | 3.4 (4) |
| Cystin | 2.5 (3) |
| Ile | 2.1 (2) |
| Leu | 3.3 (3) |
| Tyr | 1.9 (2) |
| Phe | 1.2 (1) |
| His | 1.0 (1) |
| Lys | 3.1 (3) |
| Met | 0 (0) |
| Total | (63) |

Peak 2 (fraction 17, cf. Tables 1 and 2)

| Amino acid | Hydrolysate |
| --- | --- |
| Asp | 9.9 (9) |
| Thr | 4.0 (4) |
| Ser | 3.9 (4) |
| Glu | 12.8 (13) |
| Pro | 3.1 (3) |
| Gly | 9.1 (9) |
| Val | 3.7 (4) |
| Cystine | 2.8 (3) |
| Ile | 2.1 (2) |
| Leu | 4.4 (4) |

Peak 2 (fraction 17, cf. Tables 1 and 2)

| Amino acid | Hydrolysate |
|---|---|
| Tyr | 1.2 (2) |
| Phe | 1.2 (1) |
| His | 1.2 (1) |
| Lys | 2.9 (3) |
| Met | 0 (0) |
| Total | (65) |

Peak 3 (fraction 18, cf. Tables 1 and 2)

| Amino acid | Hydrolysate |
|---|---|
| Asp | 10.0 (9) |
| Thr | 3.9 (4) |
| Ser | 4.1 (4) |
| Glu | 12.5 (12) |
| Pro | 3.1 (3) |
| Gly | 8.7 (9) |
| Val | 3.1 (4) |
| Cystin | 2.4 (3) |
| Ile | 1.9 (2) |
| Leu | 3.3 (4) |
| Tyr | 1.8 (2) |
| Phe | 1.1 (1) |
| His | 1.0 (1) |
| Lys | 2.8 (3) |
| Met | 0 (0) |
| Total | (64) | b) Partial Sequence Analysis

18 μg (2.5 nmol) of the pure hirudin compound are subjected to a conventional sequence analysis according to Edman and the N-terminal phenylthiohydantoin (PTH)-amino acids are determined by means of RP-HPLC.

Results
Peak 2 (fraction 17, cf. Tables 1 and 2)

```
Cycle      1                 5                  10
Amino    Val Val Tyr Thr Asp n.d. Thr Glu Ser Gly
acid Cycle     11                15
Amino    Gln Asn Leu n.d. Leu n.d. Glu Gly Ser
acid Circle    20                25
Amino    Asn Val n.d. Gly n.d. Gly Asn Lys n.d.
acid Cycle     29                35
Amino    Ile Leu Gly Ser Asp Gly Glu Lys Asn
acid Cycle     38        40                45
Amino    n.d. n.d. Val Thr Gly Glu Gly Thr Pro Lys
acid Cycle     48        50
Amino    Pro n.d. Ser n.d.
acid
(n.d. = not determined)
```

Peak 1 (cf. Table 2)
  Sequence from cycle 1 to cycle 29 as above.
Peak 3 (fraction 18, cf. Tables 1 and 2)
  Sequence for cycle 1 to cycle 27 as above.

The N-terminal sequences of the biosynthetic hirudin compounds examined are thus identical to that of authentic hirudin.

C. C-terminal Analysis

The hirudin compounds are digested with carboxypeptidase Y and the released amino acids determined in the amino acid analyser (cf. J. Y. Chang, R. Knedel, D. G. Braun, Biochem J. 199, 547).

Results

Peak 1 (cf. Table 2)
  C-terminal amino acids: -Glu-Tyr
Peak 2 (fraction 17, cf. Tables 1 and 2)
  C-terminal amino acids: -Glu-Tyr-Leu-Gln
Peak 3 (fraction 18, cf. Tables 1 and 2)
  C-terminal amino acids: -Glu-Tyr-Leu d) Apparent Molecular Weights The desulphathohrrudin compounds (30 μg) are analysed on a SDS urea gel [SUDS gel; cf. Kyte et al., Anal. Biochem. 133, 515 (1983)]. Prior to Coomassie blue staining fixation is done with 12% trifluoroacetic acid. A single band corresponding to a apparent molecular weight of between 6000 to 7000 Daltons is observed.

e) Molecular Weight Determination by FAB-MS

The desulphatohirudin compounds are subjected to fast atom bombardment Positive ion mass spectrometry (FAB-MS). Instrument: ZAB-HF mass spectrometer from VG-Analytical Ltd., Manchester; matrix: thioglycerol; Xenon bombardment; ion energy 10 Kev; extern calibration: $Cs_{26}J_{25}$ (molecular weight: 6887.9) and $Cs_{28}J_{27}$ (7147.76).

Results

Peak 1 (cf. Table 2)
  empirical formula: $C_{276}H_{421}N_{77}O_{107}S_6$
  molecular weight (calculated): 6722.23
  molecular weight (found): 6719.3

Peak 2 (fraction 17, cf. Tables 1 and 2)
  empirical formula: $C_{287}H_{440}N_{80}O_{110}S_6$
  molecular weight (calculated) 6963,518
  molecular weight (found) 6963,44
  The molecular weight is averaged from two different measurements.

Peak 3 (fraction 18, cf. Tables 1 and 2)
  empirical formula: $C_{282}H_{432}N_{78}O_{108}S_6$
  molecular weight (calculated): 6835.39
  molecular weight (found): 6832.9

Based on the presented data the compound of peak 1 is desulphatohirudin (1–63), the compound of peak 2 is identical with authentic desulphatohirudin (1–65) and the compound of peak 3 is novel desulphatohirudin (1–64).

f) Human Thrombin-hirudin Dissociation Constants

The dissociation constants $K_D$ of the human thrombin-desulphatohirudin complexes are determined according to the method of S. R. Stone and J. Hofsteenge, [Biochemistry 25, 4622–4628 (1986)] and are compiled in the following table. The table contains also the specific activities (expressed in ATU/mg) of the three desulphatohirudin species obtained.

| | $K_D$ [M] | Specific activity [ATU/mg] |
|---|---|---|
| yeast desulphatohirudin (1–65) | $2.9 \times 10^{-13}$ | 11000 |
| yeast desulphatohirudin (1–64) | $3.9 \times 10^{-13}$ | 9600 |
| yeast desulphatohirudin (1–63) | $3.0 \times 10^{-12}$ | 8900 | g) Further Desulphatohirudin Compounds Obtained from Transformed Yeast

The mixture of desulphatohirudin compounds, fermented and purified as described in Example 19 is further separated and in detail characterized.

The semipreparative separation on the Vydac 218 TP 510 RP-HPLC column yields in addition to the desulphatohirudin compounds described above (cf. Example 21e) desulphatohirudin-like compounds eluting from the column with the retention time 8.1 minutes.

This material is characterized by fast atom bombardment mass spectrometry (FAB-MS) and amino acid analysis, partial sequencing, and C-terminal analysis.

FAB-MS reveals that the material is a mixture of two compounds having a molecular weight of 6429.5 and 6556.8, respectively.

The amino acid composition is as follows:

| Amino acid | Hydrolysate |
|---|---|
| Asx | 8.9 (9) |
| Thr | 3.7 (4) |
| Ser | 4.1 (4) |
| Glx | 10.7 (11) |
| Pro | 3.2 (3) |
| Gly | 9.7 (9) |
| Val | 3.3 (4) |
| Cystin | 3.3 (3) |
| Ile | 2.1 (2) |
| Leu | 3.6 (3) |
| Tyr | 0.9 (1) |
| Phe | 1.1 (1) |
| His | 1.2 (1) |
| Lys | 3.2 (3) |
| Met | 0 (0) |
| Total | (61) |

Partial Sequence Analysis (N-terminus)

| Cycle | 1 | 2 | 3 |
|---|---|---|---|
| Amino acid | Val | Val | Tyr |

C-terminal Analysis (cf. Example 21c)

| | 59 60 61 62 |
|---|---|
| C-terminal amino acids | -Ile-Pro-Glu-(Glu) |

Based on these data this mixture consists of desulphatohirudin (1–61) and of desulphatohirudin (1–62).

EXAMPLE 22

Expression of Desulphatohirudin Compounds in Yeast Harboring a Desulphatohirudin Gene without Signal Sequence. (FIG. 7)

a) Isolation of the pJDB207 Vector Fragment:

6 μg of the plasmid pJDB207R/IF (α-3) (EP 100,561) are completely digested with the restriction endo-nuclease BamHI. The resulting DNA fragments (6.85 kb and 1.15 kb) are precipitated with ethanol and taken up in 400 μl of 50 mM tris.HCl pH 8.0. 4.5 units of calf intestinal phosphatase (Boehringer, Mannheim) are added. The mixture is incubated for 1 hour at 37° C., then the phosphatase is inactivated at 65° C. for 1.5 hours. The solution is adjusted to 150 mM NaCl and then applied to a DE52 (Whatman) anion exchange column (100 μl volume) which has been equilibrated beforehand with 10 mM tris.HCl pH 7.5, 150 mM NaCl, 1 mM EDTA. After a washing operation with the same buffer, the DNA is eluted with 400 Vl of 1.5M NaCl, 10 mM tris.HCl pH 7.5, 1 mM EDTA and precipitated with ethanol. The large 6.85 kb BamHI fragment is separated from the small fragment on a 1.2% agarose gel in tris-borate-EDTA buffer pH 8.3.

b) Isolation of the 534 bp PHO5 Promoter Fragment

6 μg of the plasmid p31/R (EP 100,561) are digested with the restriction endonucleases EcoRI and BamHI. The resulting 3 DNA fragments are separated on a 1.2% agarose gel in tris-borate-EDTA buffer pH 8.3. The 534 bp BamHI-EcoRI fragment is isolated. It contains the PHO5 promoter including the transcription start sites.

c) Isolation of a 206 bp DNA Fragment with the Sequence Coding for Desulphatohirudin 9 μg of the plasmid pML310 (cf. Example 13c) are completely digested with the restriction enzymes BamHI and EcoRI. The resulting two DNA fragments are separated on a 1.2% agarose gel in tris-borate-EDTA buffer. pH 8.3. The 206 bp EcoRI-BamHI fragment is isolated.

d) Ligation of the DNA Fragments

The three DNA fragments mentioned in section a–c (see above) are obtained from agarose gel blocks by electroelution, purified over DE52 (Whatman) anion exchangers, precipitated with ethanol and resuspended in $H_2O$.

0.1 pmol (0.45 μg) of the 6.85 kb BamHI vector fragment, 0.3 pmol (0.1 μg) of the 534 bp BamHI-EcoRI PHO5 promoter fragment and 0.25 pmol (34 ng) of the 206 bp EcoRI-BamHI fragment of pML310 are ligated in 15 μl of 60 mM tris.HCl pH 7.5, 10 mM $MgCl_2$, 10 mM DTT. 1 mM ATP with 600 units of $T_4$ DNA ligase (Biolabs) at 15° C. for 16 hours.

24 transformed $amp^R$ colonies are separately cultivated in LB medium with 100 μg/ml ampicillin. Plasmid DNA is isolated in accordance with the method of Holmes et al. (supra) and analysed by a HindIII-EcoRI double digestion. The appearance of an approximately 600 bp large EcoRI-Bindlll fragment indicates that in the clone concerned the PHO5 promoter-hirudin DNA fragment is in the correct orientation to the transcription stop signals on the vector. As expected, approximately 50% of the clones have the correct orientation of the insert. One of these clones is designated pJDB207R/PHO5-HIR.

e) Transformation of *Saccharomyces cerevisiae* GRF18:

*Saccharomyces cerevisiae* strain GRF18 (α, his3–11, his3–15, leu2–3, leu2–112, $can^R$) is transformed with the plasmid pJDB207R/PHO5-HIR in accordance with the protocol of Hinnen et al.(supra). Selection for transformed yeast cells is carried out on agar plates with yeast minimal medium without leucine. A transformed yeast colony is isolated and designated *Saccharomyces cerevisiae* GRF18/pJDB207R/PHO5-HIR.

f) Cultivation of *S. cerevisiae* GRF18/pJDB207R/PHO5-HIR:

Cells of *S. cerevisiae* GRF18/pJDB207R/PHO5-HIR are agitated in 20 ml of yeast minimal medium (Difco Yeast Nitrogen base without amino acids with the addition of 2% glucose and 20 mg/l L-histidine) at 30° C. and cultivated to a cell density of $3 \times 10^7$ cells/ml. The cells are washed in 0.9% NaCl and then used for inoculating 50 ml cultures in low $P_i$-minimal medium. Low $P_i$-minimal medium is prepared corresponding to the composition of Difco Yeast Nitrogen Base medium (without amino acids), but contains 0.03 g/l $KH_2PO_4$, 1 g/l KCl, and 10 g/l L-asparagine instead of $(NH_4)_2SO_4$, 2% glucose and 1 g/l L-histidine. The cultures are inoculated up to a cell density of $4 \times 10^6$ cells/ml and agitated at 30° C. for 42 hours at 200 revs/min.

g) Analysis of the Product Mixture from the Fermentation of S. cerevisiae GRF18/ pJDB207R/PHO5-HIR The cells (cf. Example 22f) are disintegrated as usual (cf., for example, European Patent Application No. 100,561). The supernatant treated with 1.5% acetic acid is centrifuged and each 2 ml of the clear solution is dried on a "Speed Vac" concentrator and in high vacuum. The samples are dissolved individually in 100 μl of water and subjected to HPLC analysis (conditions as in Example 20). The thrombin inhibition of the individual fractions is tested. The fraction with a retention time of 16.5 min as thrombin inhibition activity. According to amino acid composition this fraction is desulphatohirudin. Based on HPLC analysis the titer is about 10 μg/l culture broth. In the medium no hirudin activity is detectable.

The yields in intracellular and extracellular hirudin activity obtained from yeast strains harboring the desulphatohirudin gene without or with an appended signal sequence are summarised in Table 3. The hirudin activity is measured by the thrombin inhibition assay.

TABLE 3

| S. cerevisiae | PHO5 signal | hirudin activity (μg/l) | | |
|---|---|---|---|---|
| GRF18/plasmid | sequence | culture medium | cell extract | total |
| pJDB207/ PHO5-HIR | + | $6 \times 10^3$ | $<1 \times 10^3$ | $7 \cdot 10^3$ |
| pJDB207R/ PHO5-HIR | − | not detectable | 10 | 10 |

EXAMPLE 23

Construction of PHO5 Promoter Deletions a) Bal31 Digestion

Recombinant phage M13mp9/PHO5 Bam-Sal containing the BamHI-SalI fragment of PHO5 depicted in FIG. 8 is used as a source for the PHO5 promoter (see European Patent Application No. 143,081).

20 μg of the phage DNA (RF: replicative form) are digested with restriction endonuclease SalI, resulting in a linear DNA of approximately 9 kb. After extraction with phenol/chloroform, the DNA is precipitated with ethanol. The DNA is resuspended in 10 mM Tris pH 8.0 at a concentration of 0.5 μg/ml. 16 μg of SalI cleaved DNA are digested with 2 U of exonuclease Bal31 (BRL) in 100 μl of 20 mM Tris pH 8.0, 199 mM NaCl, 12 mM $MgCl_2$, 12 mM $CaCl_2$ and 1 mM EDTA. Aliquots of 2 μg DNA each are withdrawn after 1, 2, 3, 4, 5 and 6 min. of incubation at 30° C. and are immediately mixed with 50 μl phenol and 60 μl TNE. After extraction with phenol/chloroform and ethanol precipitation, the DNA is resuspended in 10 mM Tris pH 8.0 at a concentration of 100 μg/ml. To analyse the extent of exonucleolytic cleavage by Bal31 0.5 μg of DNA from each time point are digested with endonuclease BamHI and analysed on a 1.5% agarose gel in Tris-borate buffer pH 8.3 (90 mM Tris.HCl pH 8.3, 90 mM boric acid, 2.5 mM EDTA). On the average 100 bp are removed from each end of the fragment per 1 min of Bal31 digestion.

b) Addition of EcoRI Linkers to the Bal31 Treated DNA

Two $A_{260}$ units of EcoRI linkers (5'-GGAATTCC-3', BRL) are resuspended in 250 μl of 10 mM Tris pH 8, 1 mM EDTA. Two μg of EcoRI linkers are kinased in 75 μl of 60 mM Tris pH 7.5, 10 mM $MgCl_2$, 15 mM DDT, 10 μM ATP and 33 U of T4 polynucleotide kinase (Boehringer). After 1 h at 37° C. the mixture is allowed to cool to room temperature and is then stored at −20° C.

The annealed, double stranded EcoRI linkers are ligated with their blunt ends to the Bal31 treated DNA fragments. Half a microgram of Bal31 treated DNA (see Example 23a) is incubated for 16 hours at room temperature with a 50 fold excess of kinased EcoRI linkers in 20 μl of 60 mM Tris pH 7.5, 10 mM $MgCl_2$, 10 mM DTT, 4 mM ATP and 600 U of T4 DNA ligase (Biolabs). After inactivation of the T4 DNA ligase (10 min at 65° C.) the excess of EcoRI linkers is cleaved by 50 U of EcoRI (Boehringer) in a volume of 50 μl. The DNA is extracted with phenol/chloroform, precipitated by ethanol and resuspended in 10 mM Tris, 1 mM EDTA (=TE). Then, the DNA is cleaved with 5 units of BamHI (Biolabs) and the mixture is applied to a 1.5% low melting agarose gel (Sigma) in Trisborate buffer (see above). The bands are stained with ethidium bromide and visualized under long wave UV light at 366 nm. The broad diffuse banding patterns between about 100 bp to 600 bp is cut out of the gel and the DNA is extracted as follows: The piece ofagarose is liquified at 65° C., adjusted to 500 mM NaCl and incubated at 65° C. for 20 min. One volume of phenol (equilibrated with 10 mM Tris.HCl pH 7.5, 1 mM EDTA, 500 mM NaCl) is added. The aqueous phase is reextracted twice with phenol and once with chloroform. The DNA is precipitated with 2.5 volumes of cold absolute ethanol and collected by centrifugation. The DNA pellet is washed with cold 80% ethanol and then dried in vacuum. The DNA is resuspended in 10 μl TE.

c) Ligation into M13mp9

3 μg of RF of M13mp9 is digested with 15 units EcoRI (Biolabs) and 15 units BamHI (Boehringer) in a volume of 50 μl. After phenol extraction and ethanol precipitation the DNA is resuspended in 50 μl TE. Five μl of cut vector DNA (about 200 ng) are mixed with 10 μl of the above samples (DNA fragments resulting from various Bal31 digests as described in Example 23b) and ligated in a total volume of 20 μl in the presence of 60 mM Tris/HCl pH 7.5, 6 mM $MgCl_2$, 10 mM DTT, 1 mM ATP and 200 U of T4 DNA ligase for 15 hours. Transduction of competent cells of the strain E. coli JM101 is done according to the manual "M13 cloning and sequencing system" published by New England Biolabs. Phages from a number of white plaques are grown and analyzed for the size of their DNA inserts by cleavage with restriction enzymes EcoRI and BamHI.

d) Determination of Bal31 Deletion End Points by Sanger Sequencing (deletions from the SalI site)

Sequencing is done using the dideoxy DNA sequencing system of Sanger et al. [Proc. Natl. Acad. Sci. USA 74, 5463(1977)] as described in the above mentioned manual. The deletion end points are given below:

| clone | position of last nucleotide of the PH05 sequence (see FIG. 8) |
|---|---|
| A | −502 |
| B | −471 |
| C | −422 |
| D | −400 |
| E | −392 |
| F | −369 |
| G | −350 |
| H | −328 |
| I | −300 |
| K | −283 |
| L | −255 |
| M | −226 |
| N | −211 |
| O | −187 |
| P | −111 |
| Q | −88 |
| R | −57 |
| S | −33 | e) Determination of Bal31 Deletion End Points by Sanger Sequencing (deletions from the BamlHI site)

A similar set of Bal31 deletions is done as described under a–c, except that M13mp9 PHO5 Bam-Sal is cut by BamHI. The Bal31 digested molecules are cut by EcoRI and SalI, and the generated fragments are cloned into M13mp9 digested with EcoRI and SalI. The deletion end points are given below:

| clone | position of last nucleotide of the PH05 sequence (see FIG. 8) |
|---|---|
| A' | −24 |
| B' | −35 |
| C' | −41 |
| D' | −48 |
| E' | −74 |
| F' | −89 |
| G' | −93 |
| H' | −97 |
| I' | −124 |
| K' | −162 |
| L' | −174 |
| M' | −262 |
| N' | −277 |
| O' | −306 |
| P' | −332 |
| Q' | −346 |
| R' | −361 |
| S' | −382 |
| T' | −393 | f) Construction of Internal PHO5 Promoter Deletions

The Bal31 deletion set described under d) produces a "left arm" PHO5 promoter fragment ending with an EcoRI site and the Bal31 deletion set described under e) produces a "right arm" PHO5 promoter fragment ending with an EcoRI site. By combining "left arms" and "right arms" of various positions internal deletions are created which contain an EcoRI linker segment at the site of the deleted DNA. The individual internal deletions are constructed by cutting the "left arms" and "right arms" from the M13mp9 derivatives by restriction endonucleases EcoRI and BamHI (left arms) or EcoRI and SalI (right arms) and isolating the corresponding fragments via soft agarose gel electrophoresis as described under b). Equimolar amounts of "left arms", "right arms" and 200 ng BamHI and SalI digested M13mp9 vector DNA are ligated as described under c). After transduction into E. coli JM101 white plaques are picked, RF is produced and analyzed by restriction analysis (BamHI, SalI, EcoRI). The following arms are combined to create specific internal deletions (for numbering of the nucleotides cf. FIG. 8):

| "left arm" | "right arm" | deletion | from - to | number of nucleotides deleted |
|---|---|---|---|---|
| A | T' | Δ7 | −501 to −394 | 108 |
| B | T' | Δ8 | −470 to −394 | 77 |
| C | T' | Δ9 | −421 to −394 | 28 |
| D | S' | Δ10 | −399 to −383 | 17 |
| E | R' | Δ11 | −391 to −362 | 30 |
| F | Q' | Δ12 | −368 to −347 | 22 |
| G | P' | Δ13 | −349 to −333 | 17 |
| H | O' | Δ14 | −327 to −307 | 21 |
| I | N' | Δ15 | −299 to −278 | 22 |
| K | M' | Δ16 | −282 to −263 | 20 |
| L | L' | Δ17 | −254 to −175 | 80 |
| M | L' | Δ18 | −225 to −175 | 51 |
| N | L' | Δ19 | −210 to −175 | 36 |
| O | L' | Δ20 | −186 to −175 | 12 |
| O | K' | Δ21 | −186 to −163 | 24 |
| O | I' | Δ22 | −186 to −125 | 62 |
| O | H' | Δ23 | −186 to −98 | 89 |
| P | H' | Δ24 | −110 to −98 | 13 |
| P | G' | Δ25 | −110 to −94 | 17 |
| P | F' | Δ26 | −110 to −90 | 21 |
| Q | E' | Δ27 | −87 to −75 | 13 |
| R | D' | Δ28 | −56 to −49 | 8 |
| R | C' | Δ29 | −56 to −42 | 15 |
| R | B' | Δ30 | −56 to −36 | 21 |
| S | A' | Δ31 | −32 to −25 | 8 | g) In vivo Analysis of the Internal Deletions of the PHO5 Promoter

The various deletions described in Example 23f) are cloned into plasmid pJDB207/PHO5 [R. Haguenauer-Tsapis and A. Hinnen, Molecular and Cellular Biology, 4, 2668–2675(1984)] by replacing the wild type PHO5 Bam-Sal fragment with the deleted version. After transformation of yeast strain S. cerevisiae AH216 (cf. European Patent Application No. 143,081) the acid phosphatase activity is determined as described by Toh-e et al. [J. Bacteriol. 113, 727(1973)]. Deletions Δ11 and Δ12 show about a 10-fold reduction of PHO5 activity and define an upstream region ("upstream activation site", UAS) which is essential for PHO5 expression. A similar down effect is observed for deletion Δ17 (about 5-fold reduction) and for TATA box deletions Δ23–Δ26 (about 30-fold reduction). All other deletions show activities of approximately wild type level. These results suggest that three areas of essential information for PHO5 expression are located at the following positions:

1. between positions −349 and −383 (UAS1)
2. between positions −225 and −263 (UAS2)
3. between positions −87 and −125 (TATA box)

DNA fragments containing the UAS1 or UAS2 or UAS1 and UAS2 of PHO5 can be produced from recombinant phage M13mp9/PHO5 Bam-Sal (see above) by cleavage with appropriate restriction endonucleases. UAS1 is contained in a 268 bp BamHI-ClaI fragment having the formula GATCCGAAAGTTGTATTCAACAAGAAT-
GCGCAAATATGTCAACGTATTTGGAAGT-
CATCTT ATGTGCGCTGCTTTAATGTTTTCTCAT-
GTAAGCGGACGTCGTCTATAAACTTCAAACG
AAG               GTAAAAGGTTCAT-
AGCGCTTTTTCTTTGTCTGCACAAA-
GAAATATATATTAAATTAGCACGT TTTCGCATA-
GAACGCAACTGCACAATGCCAAAAAAGTAA
AAGTGATTAAAAGAGTTAA
TTGAATAGGCAATCTCTAAATGAAT, UAS2 is contained in a 100 bp ClaI-BstEII fragment having the formula CGATACAACCTTGGCACTCACACGTGG-GACTAGCACAGACTAAATTTATGAT-TCTGGTCCC TGTTTTCGAAGAGATCGCACAT-GCCAAATTATCAAATHG and both UAS1 and UAS2 are present in the 368 bp BamHI-BstEII fragment having the formula GATCCGAAAGTTGTATTCAACAAGAAT-GCGCAAATATGTCAACGTATTTGGAAGT-CATCTT ATGTGCGCTGCTTTAATGTTTTCTCAT-GTAAGCGGACGTCGTCTATAAACTTCAAACG AAGG TAAAAGGTTCAT-AGCGCTTTTTCTTTGTCTGCACAAA-GAAATATATATTAAATTAGCACGT TTTCGCATA-GAACGCAACTGCACAATGCCAAAAAAAGTA AAAGTGATTAAAAGAGTTAATT GAATAG-GCAATCTCTAAATGAATCGATACAACCT-TGGCACTCACACGTGGGACTAGCACAG ACT-AAATTTATGATTCTGGTCCCTGTTTTCGAAGA GATCGCACATGCCAAATTATC AAATTG.

EXAMPLE 24

Expression of Desulphatohirudin Under the Control of a Fused PHO5-GAPDH Hybrid Promoter Example 23 makes a region around position −365 [UAS1 (PHO5)] and another region around position −180 [UAS2 (PHO5)] of the PHO5 gene possible candidates for UAS with regulating functions. UAS1(PHO5) is contained in a 268 bp BamHI-ClaI fragment whereas both UAS1(PHO5) and UAS2(PHO5) are contained in a 368 bp BamHI-BstEII fragment. These two fragments are each fused to two different GAPDH downstream promoter elements which include the TATA box and transcription initiation sites of GAPDH.

a) Construction of a Yeast Gene Library

Thirty μg of total high molecular weight yeast DNA [M. V. Olsen et al., J. Mol. Biol. 132, 387(1979)] from wild type Saccharomyces cerevisiae strain S288C is incubated for 30 min at 37° C. with 2 units of EcoRI methylase (New England Biolabs) in 250 μl of EcoRI methylation buffer as recommended by the supplier. DNA is precipitated by ethanol, resuspended in 500 μl of 25 mM Tris.HCl pH 8.5, 2 mM $MgCl_2$ (EcoRI* buffer) [H. Meyer, FEBS Lett. 90, 341 (1979)] and digested with EcoRI (Boehringer) until the size distribution of the DNA fragments has a maximum in the 30–50 kb range (a XhoI digest of λDNA provides appropriate 33 kb and 17 kb markers). The yeast DNA digested under EcoRI* conditions is size-fractionated on a sucrose gradient (5–20% sucrose in 10 mM Tris.HCl pH 7.5, 1 mM EDTA) for 6 hrs at 38,000 rpm in a SW 40 rotor. Thirty fractions of 0.4 ml each are collected from the top of the gradient. Fraction 16 contains DNA fragments of 30–40 kb in size. The DNA of this fraction (3 μg) is precipitated with ethanol and ligated for 16 hours at 15° C. in a total volume of 15 μl to 1 μg of cosmid vector pYcl [B. Hohn et al. in "Genetic Engineering", Vol. 2, p. 169, New York 1980] linearized by EcoRI. Ligation is carried out with 300 U T4 DNA ligase (New England Biolabs) using the buffer system described by the supplier. The DNA is packaged in vitro into bacteriophage A [B. Hohn in "Methods in Enzymology", Vol. 68, p. 299, New York 1979] and the assembled phages are used to transduce E. coli strain HB101 ($r_k^\ominus$, $m_k^\ominus$, $leu^\ominus$, $pro^\ominus$, recA). The efficiency of transduction is about 5000 ampicillin-resistant colonies per μg of pYcl vector. 3000 $amp^R$ colonies are picked and grown individually in the wells of microtiter dishes in LB medium [10 g Bacto-Tryptone (Difco), 5 g Bacto Yeast Extract (Difco), 10 g NaCl] containing 100 μg/ml ampicillin.

b) Isolation of the Yeast GAPDH Gene

The gene library described above is screened with a synthetic oligonucleotide [prepared using the phosphotriester method: K. Itakura et al., J. Am. Chem. Soc. 97, 7327 (1975); J. F. M. de Rooij et al., Recl. Trav. Chim. Pays-Bas 98, 537 (1979)] of the following structure: 5'-GCTCCATCTTCCACCGCCCC-3'. 10 μg of the oligonucleotide are kinased using 10 μl of γ-$^{32}$P-ATP (3000 Ci/mmol, 10 μCi/μl Amersham) with T4 polynucleotide kinase (Boehringer) in a total volume of 50 μl as described by Maniatis et al. ["Molecular Cloning", Cold Spring Harbor Lab., 1982, page 125]. Colony hybridization is performed as described by the same author (page 312). Positive clones are detected by autoradiography using Kodak X-5 X-ray film. Plasmid DNA isolation produces a hybrid clone which contains a 2100 bp HindIII fragment coding for GAPDH [J. P. Holland et al., J. Biol. Chem. 254, 9839 (1979)]. Final proof for the authenticity of the cloned DNA comes from DNA sequencing experiment using the above mentioned oligonucleotide in combination with the dideoxy sequencing protocol as described by G. F. Hong [Bioscience Reports 1, 243 (1981)] for double stranded DNA. The cloned GAPDH gene (see FIG. 9) has the same sequence as pgap491 published by Holland et al. [J. Biol. Chem. 255, 2596 (1980)].

c) Preparation of GAPDH Downstream Promoter Elements (cf. FIG. 10)

The 649 bp TaqI fragment which includes position −27 to −675 from the ATG of the GAPDH gene (see FIG. 9) is isolated by digesting the above mentioned hybrid plasmid with TaqI (New England Biolaps), separating the DNA fragments on a 1.2% soft agarose gel and extracting the DNA by hot phenol (see example 23). Cloning of the TaqI fragment is done into the ClaI site of pBR322: 1 μg of pBR322 is cleaved with three units of ClaI (New England Biolabs) as described by the supplier. 300 ng of the phenolized and cut vector is ligated to about 300 ng of insert DNA (649 bp Taq fragment) using 200 U of T4 DNA ligase in a total volume of 20 μl (see example 23b). Transformation is done into E. coli HB101 for ampicillin resistance, plasmid DNA is prepared and analyzed by restriction analysis [TaqI, DraI]. The orientation of the TaqI fragment is established using restriction endonuclease DraI in combination with the BamHI site of the plasmids and a plasmid is selected which has the TaqI site of position −675 close to the HindIII site of pBR322. This plasmid designated pBR322/GAPDH is linearized using BamHI (New England Biolabs), and a digestion with Bal31 is performed as described in Example 23 except that BglII linkers (5'-CAGATCTG-3', New England Biolabs) are used, and the digested plasmid is directly circularized at a concentration of 5 μg/ml in a total volume of 20 μl. The size of the Bal31 shortened TaqI fragment is determined by restriction analysis (using BglII and HindIII). Two clones are selected which contain DNA fragments which extend about 200 bp and 265 pb respectively, from the ATG upstream into the GAPDH promoter. Both fragments contain the presumptive TATA box at about −140 bp. These clones still contain the origin of replication in the pBR322 derived part of the DNA and are named pGAPDH-F and pGAPDH-E, respectively.

d) Combining the Downstream GAPDH Promoter Element with UAS1 (PHO5) of PHO5 and the Potein Coding Region of Desulphatohirudin I) The GAPDH Element In order to extend the GAPDH promoter element from the TaqI site at position −27 to a position immediately adjacent to the ATG of the GAPDH gene two synthetic complementary oligonucleotides of the following structure are synthesized:

5' CGAATAAACACACATAAATAAAG 3'
3' TTATTTGTGTGTATTTATTTCTTAA 5'

These oligonucleotides provide the genuine GAPDH promoter sequence from position −26 to position −5 with the generation of a terminal EcoRI site. Two µg of the two Bal31 isolates from example 24c) (plasmids pGAPDH-E and -F) are digested with 6 units of TaqI in 50 µl and the resulting mixture is phenolized, ethanol precipitated and resuspended in 10 µl of water. The synthetic oligonucleotides are annealed by mixing 2 µl of each single strand in 100 µl of a solution containing 10 mM Tris.HCl pH 7.5, 10 MM MgCl$_2$, 50 mM NaCl, heating for 3 min. to 90° C. and slowly cooling the solution to room temperature (within about 3 hours). One µg of each of the TaqI digested plasmids is mixed with about a twenty fold molar excess of the annealed oligonucleotides in a volume of 20 µl for about 18 hours using 800 U of T4 DNA ligase. The whole mixture is digested with 3 units of BglII (New England Biolabs), the DNA fragments are separated on a 1.5% soft agarose gel. The BglII-EcoRI fragments of about 200 bp and 265 bp, respectively, are cut from the gel, extracted and ethanol precipitated.

Plasmid pGAPDH-E is digested with BglII and EcoRI and the large (about 3.5 kb) fragment is isolated. This fragment is used as vector to clone the 265 bp and the 200 bp BglII-EcoRI fragments using ligation, transformation and plasmid isolation conditions as described above. The plasmids produced are designated pGAPDH-EL and pGAPDH-FL. The DNA sequences of the BglII-EcoRI fragments cloned in plasmids pGAPDH-EL and pGAPDH-FL are depicted in FIG. 11. The exact size of the fragments is 266 bp and 201 bp, respectively.

II) The UAS1 (PHO5) Regulatory Element

3 µg of plasmid p31/Y (see European Patent Application No. 100,561) are digested with 6 units of ClaI (New England Biolabs). The 3' recessed ends are filled inusing the Klenow fragment of *E. coli* DNA polymerase I (Bethesda Research Laboratories) according to Maniatis (supra). BglII linkers (5'-CAGATCTG-3') are added as described in example 23. The DNA is digested with SalI and BglII (New England Biolabs) and run on a 1% soft agarose gel. The 548 bp fragment is cut from the gel, phenolized and ethanol precipitated as described above.

III) The DNA Coding for Desulphatohirudin

Construction of plasmid pJDB207/PHO5(Eco)-HIR (cf. FIG. 12). For convenient joining of the UAS (PHO5)-GAPDH hybrid promoter elements to the coding region of desulphatohirudin including the PHO5 signal sequence (as in plasmid pJDB207/PHO5-HIR) an EcoRI restriction site is introduced in the 5' nontranslated region between the mRNA start sites and the ATG of the coding region.

15 µg of plasmid pJDB207/PHO5-HIR (see Example 16d) are, digested with restriction endonuclease DraI (Boehringer). The resulting 4 fragments are separated on a 0.8% agarose gel in Tris-borate-EDTA buffer pH 8.3. The 4.2 kb DNA fragment is recovered from the gel, electro-eluted and precipitated by ethanol. The DNA is resuspended in H$_2$O at a concentration of 0.6 mg/ml.

Two synthetic oligonucleotides of the formula

5'- AATTCGATTACCAATGTTT -3'
3'- GCTAATGGTTACAAA -5'

(2.3 µg and 2.9 µg, respectively) are each kinased in 20 µl of 60 mM Tris pH 7.5, 10 mM MgCl$_2$, 5 mM DTT, 0.5 mM ATP and 20 U of T4 polynucleotide kinase (Boehringer). After 45 min at 37° C. both reaction mixtures are combined, heated for 10 min at 75° C. and allowed to cool to room temperature. The annealed oligonucleotide linker is stored at −20° C.

6.5 µg (2.3 pmoles) of the 4.2 kb DraI DNA fragment are incubated for 16 h at 15° C. with a 70 fold excess of the kinased and annealed oligonucleotide linker in 50 µl of 60 mM Tris pH 7.5, 10 mM MgCl$_2$, 5 mM DTT, 3.5 mM ATP and 800 U of T4 DNA ligase (Biolabs). After inactivation of the T4 DNA ligase for 10 min at 85° C. the excess linkers are removed by precipitaion of the DNA in the presence of 10 mM EDTA, 300 mM sodium-acetate pH 6.0 and 0.54 volumes of isopropanol. The DNA is digested with EcoRI and HindIII. The resulting fragments are separated on a 1% agarose gel in Tris-borate-EDTA buffer pH 8.3. The 643 bp fragment is recovered from the gel by electroelution and ethanol precipitation. The DNA is resuspended at a concentration of 0.1 pmoles/pl. The EcoRI-HindIII fragment contains the PHO5 signal sequence, the coding sequence of desulphatohirudin and the PHOS transcription terminator.

The 534 bp PHO5 promoter fragment is isolated from plasmid p31/R (European Patent Application No. 100,561).

Ten µg of p31/R are digested with restriction endonucleases EcoRI and BamHI. The resulting 3 fragments are separated on a 0.6% low melting agarose gel in Tris-borate-EDTA buffer pH 8.3. A 534 bp BamHI-EcoRI fragment is isolated which contains the PHO5 promoter including the mRNA start sites.

The vector fragment is isolated from plasmid pJDB207/PHO5-HIR (see Example 16d). 6 µg of this plasmid are digested with BamHI and Hind III. The large 6.5 kb BamHI-HindIII fragment is separated from the small fragment on a 0.6% low melting agarose gel in Tris-borate-EDTA buffer pH 8.3.

Three DNA fragments described above with the appropriate sticky ends are ligated in the following reaction: 0.2 pmoles (70 ng) of the 534 bp BamHI-EcORI PHO5 promoter fragment, 0.2 pmoles (85 ng) of the 643 bp EcoRI-HindIII fragment (hirudin coding sequence) and 0.1 pmole (0.4 µg) of the 6.5 kb BamHI-HindIII vector fragment are ligated in 10 µl of 60 mM Tris pH 7.5, 10 mM MgCl$_2$, 5 mM DTT, 1 mM ATP and 400 U of T4 DNA ligase for 6 h at 15° C. A one µl aliquot of the ligation mixture is added to 100 µl of calcium treated, transformation competent *E. coli* HB101 cells. 12 transformed, amp$^R$ colonies are grown individually in LB medium containing 100 µg/ml of ampicillin. Plasmid DNA is prepared according to the method of Holes et al. [Anal. Biochem. 114 (1981) 193] and is analysed by EcoRI and BamHI restriction digests. One clone with the expected restriction fragments is isolated and referred to as pJDB207/PHO5 (Eco)-HIR.

IV) Ligation of the UAS1 (PHO5)-GAPDH hybrid promoters to the Protein Coding Region of Desulphatohirudin 15 µg of plasmid pJDB207/PHO5(Eco)-HIR (see Example24 dIII) are digested with EcoRI and HindIII The DNA fragments are separated on a 1% agarose gel in Tris-borate-EDTA buffer pH 8.3. The 643 bp fragment is isolated from the gel, electro-eluted and precipitated with ethanol. The DNA is resuspended in H$_2$O at a concentration of 0.1 pmoles/µl.

6 µg of plasmid pJDB207/PHO5-HIR are digested to completion with restriction endonucleases HindIII and SalI. The large 6.3 kb fragment (vector part) is isolated by soft agarose gel electrophoresis, phenol extraction and ethanol precipitation. The vector DNA fragment is resuspended in H$_2$O at a concentration of 0.05 pmoles/µl.

10 µg of plasmid pGAPDH-EL (see Example 24dI) are digested with BglII and EcoRI. The 266 bg BglII-EcoRI fragment is separated on a 1.2% agarose gel in Tris-borate-EDTA buffer pH 8.3, electroeluted from the gel and precipitated with ethanol.The DNA is resuspended in $H_2O$ at a concentration of 0.3 pmoles/µl.

0.3 pmoles of the 548 bp SalI-BglII fragment comprising UAS1 (PHO5) (Example 24dII), 0.3 pmoles of the 266 bp BglII-EcoRI fragment of pGAPDH-EL, 0.3 pmoles of the 643 bp EcoRI-HindIII fragment of pJDB207/PHO5(Eco)-HIR and 0.12 pmoles of the 6.3 kb SalI-HindIII vector fragment are ligated in 20 µl of 60 mM Tris pH 7.5, 10 mM $MgC_2$, 5 mM DTT, 1 mM ATP and 400 U of T4 DNA ligase (Biolabs) for 6 h at 15° C. Aliquots of 1 µl and 3 µl of the ligation mixture are added to 100 µl of calcium treated *E. coli* HB101 cells. Plasmid isolation from $amp^R$ colonies and restriction analysis with SalI, BglII, EcoRI and HindIII is performed as described above (see Example 24dIII). One positive clone is selected and referred to as pJDB207/PAPEL-HIR(UAS1).

An analogous construction is done with the 201 bp BglII-EcoRI fragment isolated from pGAPDH-FL. One selected plasmid is called pJDB207/PAPFL-HIR(UAS1).

V) Ligation of the UAS1 (PHO5)-UAS2(PHO5)-GAPDH Hybrid Promoters to the Protein Coding Region of Desulphatohirudin (see FIG. 13)

3 µg each of plasmids pJDB207/PAPEL-HIR (UAS1) and pJDB207/PAPFL-HIR (UAS1) are digested with BglII. After phenol extraction and ethanol precipitation the 3' recessed ends of the DNA are filled in a reaction with *E. coli* DNA polymerase (Klenow fragment; Bethesda Research Laboratories) according to Maniatis et al. (supra). The enzyme is inactivated at 70° C. for 10 min. The DNAs are further digested with SalI and the large 7.2 kb fragments are isolated by soft agarose gel electrophoresis, phenol extraction and ethanol precipitation. Each fragment is resuspended in $H_2O$ at a concentration of 0.05 pmoles/µl. The fragments contain the hirudin coding region, most of the vector sequences and either of two different GAPDH promoter elements isolated from pGAPDH-EL or pGAPDH-FL.

Plasmid p31/Y (European Patent Application No. 100, 561) is digested with BstEII, incubated with *E. coli* DNA polymerase (Klenow fragment) as described above and cleaved with SalI. The 649 bp fragment is separated on a soft agarose gel and recovered by phenol extraction and ethanol precipitation.

0.3 pmoles of the 649 bp fragment of p31/Y comprising the UAS1–UAS2(PHO5) promoter element and 0.15 pmoles of either of the 7.2 kb fragments are ligated and transformed into *E. coli* HB101 as described above. Plasmids are prepared from $amp^R$ colonies and analysed by restriction digests. Single clones are selected and their plasmid DNAs are referred to as pJDB207/PAPEL-HIR(UAS1+UAS2) and pJDB207/PAPFL-HIR(UAS1+UAS2).

EXAMPLE 25

GAPDH Promoter Elements Fused to the Protein Coding Sequence of Desulphatohirudin Two GAPDH promoter elements of different length (as described in Example 24dI) are ligated to the protein coding region of desulphatohirudin including the PHO5 signal sequence.

The two elements (266 bp and 201 bp, respectively) comprise the GAPDH TATA box, the mRNA start sites and an AT rich 5' nontranslated region. The nucleotide sequence of both elements is shown in FIG. 10.

The 3' ends of the elements are both at position –5 from the ATG of the GAPDH gene followed by an EcoRI recognition site (see oligonucleotide linker introduced in Example 24dI), the 5' ends are at position –198 and –263, respectively, from the ATG with BglII linkers added at these positions.

The BglII-EcoRI promoter fragments are ligated to an EcoRI-HindIII fragment with sequences coding for the PHO5 signal sequence and desulfatohirudin and to a HindIII-BamHI vector fragment.

6 µg of plasmid pJDB207/PHO5-HIR are digested to completion with restriction endonucleases HindIII and BamHI. The large 6.5 kb fragment (vector part) is separated on a 0.8% agarose gel in Tris-borate-EDTA buffer pH 8.3, electroeluted from the gel, phenol extracted and precipitated with ethanol. The vector DNA fragment is resuspended in $H_2O$ at a concentration of 0.05 pmoles/µl.

0.3 pmoles of the 266 bp BglII-EcoRI fragment of pGAPDH-EL (Example 24d IV), 0.3 pmoles of the 643 bp EcoRI-HindIII fragment of pJDB207/PHO5(Eco)-HIR (Example 24d III) and 0.1 pmoles of the 6.5 kb HindIII-BamHI vector fragment are ligated in 10 µl of 60 mM Tris pH 7.5, 10 mM $MgCl_2$, 5 mM DTT, 1 mM ATP and 400 U of T4 DNA ligase (Biolabs) for 6 h at 15° C. 1 µl of the ligation mixture is added to 100 µl of calcium treated *E. coli* HB101 cells. Plasmid isolation from amp colonies and restriction analysis with EcoRI is performed as described in Example 24d III. One positive clone is selected. Its plasmid DNA is referred to as pJDB207/GAPEL-HIR.

An analogous construction is done with the 201 bp BglII-EcORI fragment isolated from pGAPDH-FL. The plasmid DNA of one selected clone is called pJDB207/GAPFL-HIR.

EXAMPLE 26

Construction of Expression Plasmids with Tandem Inserts of the Coding Sequence of Secreted Desulphatohirudin (see FIG. 14)

The following constructions contain a DNA fragment duplicated in a tandem head to tail arrangement. The duplicated fragment comprises the GAPDH promoter or a hybrid PHO5-GAPDH promoter (as described in Examples 24 and 25, respectively), the POH5 signal sequence, the coding sequence of desulphatohirudin and the PHO5 transcription terminator.

7 µg of plasmid pJDB207/GAPEL-HIR are digested with restriction endonuclease HindIII. The 3' recessed ends are filled in a reaction with *E. coli* DNA polymerase I (Klenow fragment; Bethesda Research Laboratory) according to Maniatis (supra). 1,85 µg of SalI linker 5'-GGTCGACC-3' (Biolabs) are kinased in 50 µl of 60 mM Tris pH 7.5, 10 MM $MgCl_2$, 5 mM DTT, 0.5 mM ATP and 50 U of T4 polynucleotide kinase (Boehringer). After 45 min at 37° C. the mixture is heated for 10 min at 75° C. and allowed to cool to room temperature. 7 µg (1.5 pmoles) of linearized plasmid PJDB pJDB207/GAPEL-HIR with the HindIII sites converted to blunt ends (see above) are incubated for 16 h at 15° C. with an 80 fold excess of kinased and annealed Sal linkers in 30 µl of 60 mM Tris pH 7.5, 10 mM $MgCl_2$, 5 mM DTT, 3,5 mM ATP and 800 U of T4 DNA ligase (Biolabs). After inactivation of the T4 DNA ligase at 75° C. for 10 min the excess linkersare removed by precipitation of the DNA in the presence of 10 mM EDTA, 300 mM sodium acetate pH 6.0 and 0.54 volumes of isopropanol. The DNA is digested with SalI. The resulting fragments are separated on a 1% agarose gel in Tris-borate-EDTA buffer pH 8.3. The 1.1 kb SalI fragment is recovered from the gel by electroelution, phenol extraction and ethanol precipitation. The DNA is resuspended at a concentration of 0.1 pmoles/μl.

5 μg of plasmid pJDB207/GAPEL-HIR are digested with SalI to completion. After phenol extraction and ethanol precipitation the DNA is resuspended in 100 μl of 50 mM Tris pH 8.0. 4.6 U of calf intestine alkaline phosphatase (Boehringer) are added. After 1 h at 37° C. the phosphatase is inactivated in the presence of 100 mM NaCl, 5 mM EDTA and 0.5% SDS for 15 min at 68° C. The DNA solution is applied to a 100 μl bed of DE 52 (Whatman) anion exchanger equilibrated with 10 mM Tris pH 7.5, 150 mM NaCl and 1 mM EDTA. After washing the column with the same buffer, the DNA is eluted with 400 μl of 1.5M NaCl, 10 mM Tris pH 7.5, 1 mM EDTA and precipitated with ethanol. Linearized plasmid is separated from uncut DNA on a 0.6% agarose gel in Tris-acetate buffer. The linear 7.3 kb DNA fragment is recovered from the gel, electroeluted, phenol extracted, ethanol precipitated and resuspended at a concentration of 0.1 pmoles/μl.

0.2 pmoles of the 1.1 kb SalI fragment and 0.1 pmoles of the linearized vector are ligated in 10 μl of 60 mM Tris pH 7.5, 10 mM MgCl$_2$, 5 mM DTT, 1 mM ATP and 200 U of T4 DNA ligase for 16 h at 15° C. A one μl aliquot of the ligation mixture is added to 100 μl of calcium treated, transformation competent E. coli HB101 cells.

24 transformed, amp$^R$ colonies are grown individually in LB medium containing 100 μg/ml of ampicillin. Plasmid DNA is prepared according to the method of Holmes et al [Anal. Biochem. 114 (1981) 193] and is analysed by EcoRI restriction digest. One clone with the expected restriction fragments is isolated and referred to as pJDB207/[GAPEL-HIR]D.

Analogous constructions are done with plasmids pJDB207/GAPFL-HIR and pJDB207/PAPFL/HIR(UAS1+UAS2). The resulting plasmid DNA of one selected clone each is called pJDB207/[GAPFL-HIR]D and pJDB207/[PAPFL-HIR(UAS1+UAS2)]D.

EXAMPLE 27

Construction of an Expression Plasmid with Four Inserts of the Coding Sequence of Secreted Desulphatohirudin Four copies of a DNA fragment comprising a GAPDH-promoter, the PHO5 signal sequence, the coding sequence of desulphatohirudin and the PHO5 transcription terminator are inserted in the yeast expression vector in a tandem head to tail arrangement. 10 μg of plasmid pJDB207/[GAPFL-HIR]D (see Example 26) are digested with SalI. The sticky ends of the resulting linear fragment are filled in a reaction with E. coli DNA polymerase I (Klenow fragment, BRL) according to Maniatis et al. (supra). 0.94 μg of HindIII linker [5'-CAAGCTTG-3', Biolabs] are kinased, self-annealed and ligated to the linearized plasmid PJDB207/[GAPFL-HIR]D with the SalI sites converted to blunt ends (see above). Linker ligation and isopropanol precipitation is as described in Example 26. The DNA is subsequently cleaved with HindIII and the resulting 2.2 kb fragment is isolated by electroelution, phenol extraction and ethanol precipitation. The DNA is resuspended at a concentration of 0.1 pmoles/μl.

5 μg of plasmid pJDB207/[GAPFL-HIR]D are digested with HindIII to completion. The DNA is dephosphorylated with calf intestine alkaline phosphatase (Boehringer), purified by DE52 ion exchange chromatography and isolated from an 0.6% agarose gel by electroelution as described in Example 26.

0.2 pmoles of the 2.2 kb HindIII fragment and 0.1 pmoles of the linearized vector are ligated (supra). A one μl aliquot of the ligation mixture is added to 100 μl of calcium treated, transformation competent E. coli HB101 cells.

12 transformed, amp$^R$ colonies are grown individually in LB medium containing 100 μg/ml ampicillin. Plasmid DNA is prepared and analysed by SalI, XbaI; AvaI, XbaI double digests and BamHI digests. A 1.1 kb BamHI-junction fragment indicates that the insert is present in a head to tail arrangement with respect to the two copies already on the plasmid. One clone with this orientation of the insert is referred to as pJDB207/[GAPFL-HIR]T.

EXAMPLE 28

Construction of a Yeast Expression Vector Containing the PHO5 Promoter, the Invertase Signal Sequence and the Desulphatohirudin Coding Region A) Synthesis of oligodeoxyribonucleotides for invertase signal sequence Four oligodeoxyribonucleotides: I-1, I-2, I-3, I-4 are synthesized by DNA synthesizer (model 380B Applied Biosystems). After deblocking the synthetic fragments are purified on a 12% polyacrylamide gel containing 8 M urea. Salt-free pure oligodeoxyribonucleotides are obtained using Sep. Pak (Waters Associates). These fragments constitute a duplex which encodes the invertase signal sequence with the frequently used yeast codons.

```
                        HindIII
      EcoRI   MetLeuLeuGlnAlaPheLeuPheLeuLeu
I-1 5'AATTCATGCTTTTGCAAGCTTTCCTTTTCCTTTT 3'
I-2     3'GTACGAAAACGTTCGAAAGGAAAAGGAAAACCGAC 5'

AlaGlyPheAlaAlaLysIleSerAla
I-3 5'GGCTGGTTTTGCAGCCAAAATATCTGCATCTTAGCGTC 3'
I-4     3'CAAAACGTCGGTTTTATAGACGTAGAATCGCAGAGCT 5'
                                      HgaI
                                         XhoI
```

B) Subcloning of the invertase signal sequence
a) Preparation of Vector:

1.5 μg of p31R/SS-TPAΔ2 (European Patent Application No. 143,081) is digested with 10 U of EcoRI (Boehringer) in 50 μl of 10 mM Tris.HCl pH 7.5, 6 mM MgCl$_2$, 100 mM NaCl, 6 mM mercaptoethanol for one hour at 37° C. After adding 1 μl of 2.5 M NaCl, 10 U of XhoI (Boehringer) are added and incubated at 37° C. for one hour. The 4.2 kb vector is isolated on a 0.8% preparative agarose gel. The gel slice is transferred to a Micro Colloidor tube (Sartorius GmbH), covered with 200 μl of TE and electroeluted (electrophoresed at 90 mA for 50 min). The TE solution is collected and precipitated in 2.5 volumes of absolute ethanol after the addition of 0.1 volume 10×TNE. The DNA pellet is washed with cold 80% ethanol and dried in vacuum. The DNA is resuspended in 6 μl TE (40 pmoles/μl).

b) Annealing Oligodeoxyribonucleotides (I-1, I-2, I-3, I-4), Kination and Ligation with Vector A solution containing 10 pmoles of each of the four deoxyribonucleotides in 10 μl of 0.5 M Tris.HCl pH 8 is incubated at 95° C. for 5 minutes on a water bath. The water bath is slowly cooled to 30° C. over a period of 5 hours. To this annealed mixture is added 2 μl each of 0.1 M MgCl 0 .1 M NaCl, 30 mM DTT, 4 mM ATP and 8 U (1 μl) of polynucleotide kinase (Boehringer). Kination is carried out at 37° C. for one hour. The annealed, kinased oligodeoxyribonucleotides and 60 pmoles of the EcoRI-XhoI cut vector (1.5 µl) are ligated with 400 U (1 µl) of T4 DNA ligase (Biolabs) at 14° C. for 17 hours. The reaction is stopped by incubation at 65° C. for 10 min. 10 µl of this ligation mixture is used for transformation of E. coli HB101 Ca++ cells [M. Dagert and S. D. Ehrlich, Gene 56, 23–28 (1979)]. 20 amp$^R$ colonies are picked. DNA is prepared by the quick isolation procedure. [D. S. Holmes and M. Quigley, Anal. Biochem. 114, 193–197 (1981)]. DNA is digested with EcoRI and XhoI, radiolabelled at the EcoRI end and analysed on a 6% polyacrylamide gel containing 8 M urea using radiolabelled pBR322 HaeIII cut DNA as marker. Correct size bands are observed for DNA obtained from all the 20 clones. One clone is grown in 100 ml LB medium containing 100 µg/ml of ampicillin. Plasmid DNA is isolated and is referred to as p31RIT-12.

C) Joining of the GAPFL Promoter Element to the Invertase Signal Sequence

5 µg of plasmid p31RIT-12 are digested to completion with SalI and EcoRI. The large, 3.3 kb SalI-EcoRI fragment is isolated on a 0.6% agarose gel in Tris-acetate buffer pH 8.2. The DNA is electroeluted from the gel, phenol extracted and ethanol precipitated. 10 µg of plasmid pJDB207/GAPFL-HIR (see Example 25) are digested with SalI and EcoRI. The 477 bp SalI-EcoRI fragment is isolated on a 0.8% agarose gel in Tris-borate-EDTA buffer pH 8.3. The DNA is electroeluted, phenol extracted and ethanol precipitated. Both isolated DNA fragments are ligated. An aliquot of the ligation mixture is used to transform competent E. coli HB101 cells. Amp$^R$ colonies are grown and the plasmid DNA is analysed by HindIII, SalI double digestion. A plasmid with the correct insert is called p31/GAPFL-IT.

D) Construction of plasmid pJDB207/GAPFL-I-HIR (see FIG. 15)

25 µg of plasmid p31/GAPFL-IT are digested to completion with PstI and SalI. The resulting 676 bp fragment is isolated on a 10% preparative agarose gel in Tris-borate-EDTA buffer pH 8.3. The DNA is electroeluted, purified by DE52 ion exchange chromatography, ethanol precipitated and resuspended in buffer recommended for HgaI digests at a concentration of 0.1 µg/µl. The SalI-PstI DNA fragment is partially digested with HgaI in the presence of 0.5 units/µg DNA for 60 min at 37° C. The reaction is stopped by the addition of EDTA to a final concentration of 10 mM. The 534 bp SalI-HgaI fragment is isolated on a 1% preparative agarose gel. The DNA is electroeluted from the gel, purified by DE52 chromatography, ethanol precipitated and resuspended in H$_2$O at a concentration of about 0.1 pmole/µl.

10 µg of plasmid pJDB207/PHO5-HIR (see Example 16) are digested with BalI and HindIII. The resulting 587 bp BalI-HindII fragment is isolated on a preparative 1% agarose gel. The DNA is electroeluted, ethanol precipitated and further digested with HinfI.

1.3 µg (160 pmoles) each of the following oligodeoxynucleotides

5'-CTGCAGTTGTTTACACCGACTGCACCG-3'
3'-CAACAAATGTGGCTGACGTGGCTTA-5' are kinased and annealed as described in Example 24dIII. 0.6 µg (1.6 pmoles) of the HinfI digested BalI-HindIII fragment (see above) and: 160 pmoles of the kinased and annealed linker are ligated for 16 hours at 15° C. in 83 µl of 10 mM Tris-HCl pH 7.5, 10 mM MgCl$_2$, 5 mM DTT, 3.5 mM ATP and 400 units of T4 DNA ligase. After 10 min at 85° C. excess linkers are removed by isopropanol precipitation of the DNA (see Example24dIII). The 584 bp HgaI-HindIII fragment is isolated on a 1% preparative agarose gel. The electroeluted, purified and ethanol precipitated DNA is resuspended in H$_2$O at a cencentration of 0.1 pmole/µl.

5 µg of pJDB207/PHO5-HIR are digested with HindIII and SalI and the large, 6.2 kb fragment is isolated.

0.2 pmoles of the 534 bp SalI-HgaI fragment, 0.2 pmoles of the 584 bp HgaI-HindIII fragment and 0.1 pmoles of the 6.2 kb SalI-HindIII vector fragment are ligated for 5 hours at 15° C. in 10 µl of 10 mM Tris.HCl pH 7.5, 10 mM MgCl$_2$, 5 mM DTT, 1 mM ATP and 400 units of T4 DNA ligase. A one µl aliquot of the ligation mixture is used to transform competent E. coli HB101 cells.

24 transformed, ampicillin resistant colonies are grown individually in LB medium containing 100 µg/ml ampicillin. Plasmid DNA is prepared and analysed by HindIII, SalI double digestion. A single clone with the correct restriction pattern is isolated and referred to as pJDB207/GAPFL-I-HIR. The identity of the invertase signal sequence and the correct fusion with the hirudin coding sequence is confirmed by nucleotide sequencing.

EXAMPLE 29 a) Transformation of Saccharomyces cerevisiae GRF 18:

Saccharomyces cerevisiae strain GFR18 (α, his3–11, his3–15, leu2–3, leu2–112, can$^R$) is transformed with the plasmids pJDB207/PAPEL-HIR(UAS1),
pJDB207/PAPFL-HIR(UAS1),
pJDB207/PAPEL-HIR(UAS1+UAS2),
pJDB207/PAPFL-HIR(UAS1+UAS2),
pJDB207/GAPEL-HIR,
pJDB207/GAPFL-HIR,
pJDB207/[GAPEL-HIR]D,
pJDB207/[GAPFL-HIR]D,
pJDB207/[PAPFL-HIR(UAS1+UAS2)]D,
pJDB207/[GAPFL-HIR]T,
pJDB207/GAPFL-I-HIR using the transformation protocol described by Hinnen et al. [Proc. Natl. Acad. Sci. USA 75, 1929 (1978)]. Transformed yeast cells are selected on yeast minimal media plates deficient in leucine. Single transformed yeast colonies are isolated and referred to as Saccharomyces cerevisiae GRF18/pJDB207/PAPEL-HIR (UAS1),
Saccharomyces cerevisiae GRF18/pJDB207/PAPFL-HIR (UAS1),
Saccharomyces cerevisiae GRF18/pJDB207/PAPEL-HIR (UAS1+UAS2),
Saccharomyces cerevisiae GRF18/pJDB207/PAPFL-HIR (UAS1+UAS2),
Saccharomyces cerevisiae GRF18/pJDB207/GAPEL-HIR,
Saccharomyces cerevisiae GRF18/pJDB207/GAPFL-HIR,
Saccharomyces cerevisiae GRF18/piDB207/[GAPEL-HIR]D,
Saccharomyces cerevisiae GRF18/pJDB207/[GAPFL-HIR]D,
Saccharomyces cerevisiae GRF18/pJDB207/[PAPFL-HIR(UAS1+UAS2)]D,
Saccharomyces cerevisiae GRF18/pJDB207/[GAPFL-HIR]T,
Saccharomyces cerevisiae GRF18/pJDB207/GAPFL-I-HIR.

b) Fermentation of the Transformants

Cells of the S. cerevisiae GRF18 transformants are each grown in 10 ml of yeast minimal medium (Difco Yeast Nitrogen Base without aminoacids to which 2% glucose and 20 mg/l L-histidine are added) in a 50 ml Erlenmeyer flask with shaking at 30° C. for 24 hours to a density of $3 \times 10^7$ cells/ml. Yeast transformants containing plasmids with a hybrid PHO5-GAPDH promoter require derepression of the promoter for the expression of desulphatohirudin. The cells are washed in 0.9% NaCl and used to inoculate 50 ml of a low $P_i$ minimal medium prepared according to the recipe of the Difco Yeast Nitrogen Base medium (without amino acids), but containing 0.03 g/l $KH_2PO_4$, 10 g/l L-asparagine instead of $(NH_4)_2SO_4$, 2% glucose and 1 g/l L-histidine. The cultures are inoculated up to a cell density of $4 \times 10^6$ cells/ml and agitated at 30° C. for up to 24 hours at 200 revs/min. Final densities of $1 \times 10^8$ cells/ml are obtained.

Yeast transformants comprising plasmids with the GAPDH promoter express desulphatohirudin constitutively. Cells are grown in a complex medium consisting of (g/l) peptone (5), yeast extract (10), glucose (20), sucrose (40), ammonium sulphate (3), $KH_2PO_4$ (2), $MgSO_4$ (0.5), NaCl (0.1), $CaCl_2$ (0.1), biotin (10 $\mu$g/l). Approximately $1 \cdot 10^9$ cells/ml are obtained after 48 hours of incubation at 30° C. and 200 revs/min.

The amounts of desulphatohirudin (as determined by the thrombin inhibition assay) secreted by some representative transformed yeast strains are compiled in the following table.

| Strain<br>Saccharomyces cerevisiae GRF18/ | secreted hirudin (mg/l) | time of harvest (hours) |
| --- | --- | --- |
| pJDB2077PAPFL-HIR(UAS1) | 7 | 24 |
| pJDB207/PAPFL-HIR(UAS1 + UAS2) | 8 | 24 |
| pJDB207/GAPFL-HIR | 41 | 48 |
| pJDB207/GAPEL-HIR | 35 | 48 |
| pJDB207/[GAPFL-HIR]D | 39 | 48 |
| pJDB207/[GAPEL-HIR]D | 31 | 48 |

Furthermore, it is determined that at least 90% of the desulphatohirudin compounds expressed by the yeast transformants is secreted into the culture medium. In order to determine the distribution of desulphatohirudin in the culture broth and inside the cells as a function of the time of harvest, fermentation is run in a 3 l MBR bioreactor (MBR Bioreactor AG, Wetzikon, Switzerland). Strain *Saccharomyces cerevisiae* GRF18/pJDB207/GAPFL-HIR is inoculated into 3 l of complex medium (see above) and incubated at 30° C. with an agitation rate of 500 revs/min and an aeration rate of 200 l/h. A final density of $5 \cdot 10^9$ cells/ml is reacted. Samples are taken at 18, 24 and 42 hours, respectively, and the content of desulphatohirudin in the culture broth and inside the cells (after disintegration, see Example 22) is determined by the thrombin inhibition assay and by HPLC.

| | time (h) | desulpatohirudin (mg/l)<br>thrombin inhibition | HPLC |
| --- | --- | --- | --- |
| culture broth | 18 | 60 | 78 |
| cell interior | 18 | 7 | <1 |
| culture broth | 24 | 70 | 70 |
| cell interior | 24 | 9 | <1 |
| culture broth | 42 | 110 | 105 |
| cell interior | 42 | 9 | <1 |

EXAMPLE 30

Cultivation of Transformants on a 300 l Scale
a) The Inoculation Cycle

A number of agar slopes are inoculated from a deep frozen ampoule containing cells of strain *Saccharomyces cerevisiae* GRF18/pJDB207/GAPFL-HIR. One or more agar slopes are incubated for 3–5 days at 28–30° C. The contents of a single agar slope is inoculated sterilely into single 500 ml Erlenmeyer flasks without baffles and containing 100 ml of preculture medium. The flasks are shaken on a rotary shaker with a 50 mm throw at 250 r.p.m. with an incubation temperature of 28° C. After 48 hours, 2% (v/v) of the contents of these flasks (1st preculture) is inoculated sterilely into 2 l Erlenmeyer flasks containing 600 ml of preculture medium. These flasks (2nd preculture) are shaken for 48 hours at 28° C. on a rotary shaker at 120 r.p.m. with a 50 mm throw. The content of one of the 2nd preculture flasks (2% v/v) is introduced sterilely into a 50 l stainless steel fermenter containing 30 l of preculture medium (plant preculture). The fermentation conditions for the plant preculture are as follows: 600 r.p.m. (single six-bladed turbine stirrer, 115 mm diameter), 4 baffles; head pressure: 0.3 bar; aeration 1 liter of air per liter of medium per minute, temperature 28° C., 48 hours duration.

The agar medium and the preculture medium are the same except for the presence or absence of agar. The same preculture medium was used for all preculture stages. Composition of preculture medium (g/l):

| yeast nitrogen base (Difco) | 8.4 |
| --- | --- |
| L-asparagine.$H_2O$ | 11.6 |
| L-histidin | 1.0 |
| glucose (separately sterilized) | 2.0 |

Composition of agar medium:
same as preculture medium plus 20 g agar/l.
b) The Production Fermentation (300 l scale)

5% (v/v, 15 l) of the grown plant preculture are introduced sterilely into a 600 l fermenter containing 300 l of sterile fermentation production medium. The fermentation conditions for the 300 l production medium are as follows: 450 r.p.m. (single six-bladed stirrer, diameter 230 mm); 4 baffles; head pressure: 0.3 bar; air-throughput: 0–9 hours; 0.25 liters of air per liter of medium per minute, 9 hours-harvest: 1 l of air per liter of medium per minute; temperature:.28° C., duration 24–48 hours. $OD_{600}$ 15–20. Yield: 15–25 mg/l (test methods: HPLC and thrombin tests).

| peptone | 5 |
| --- | --- |
| yeast extract | 10 |
| sucrose | 40 |
| $(NH_4)_2SO_4$ | 6 |
| $MgSO_4.7H_2O$ | 1 |
| NaCl | 0.1 |
| $KH_2PO_4$ | 2 |
| $CaCl_2.2H_2O$ | 0.013. | pH before sterilization ~6.0
antifoam: UCON LB 625 as required.

EXAMPLE 31

Isolation of Desulphatohirudin from the 300 l Culture Broth

The culture broth (cf. Example 30) having a pH value of 3.3 is cooled to 17° C. The cells are separated by a Westfalia SA-14 de-sludging device (400–600 l/h). The thick sludge is discarded. The slightly turbid supernatant is filtered through a series of Skan filter cartouches (first: pore width 5 μm; second: pore width 1 μm; third: pore width 0.22 μm), brought to pH 7.5 with NaOH and applied to a DEAE anion exchange column. The column is washed with sodium acetate (20 mM, pH 4.5) and eluted with sodium acetate (20 mM, pH 3.1). The solution (15 l) is brought to pH 7.5 with NaOH and concentrated to a final volume of 1.8 l in a circulation evaporator. An aliquot of 1 l is applied to a Sephadex G-25 column (bed volume: 8 l; the column being equilibrated with water). Fractions containing desulphatohirudin are identified by HPLC. The desulphatohirudin fraction (2.5 l) is concentrated with a rotavap in high vacuum to a final volume of 200 ml and is lyophilized.

An aliquot (2 g) of the raw material is dissolved in 50 ml of water, brought to pH 7.5 with NaOH and applied to a Q Sepharose fast flow column (bed volume: 200 ml). The column is washed with ammonium formiate (100 mM, pH 3.9). 25 ml fractions are taken and tested for desulphatohirudin by HPLC. Fraction containing desulphatohirudin (1–65) are pooled (125 ml) and concentrated with a rotavap in high vacuum to a final volume of 10 ml. The concentrated solution is applied to a Sephadex G-25 column (Amicon, the column being equilibrated with water) for desalting. The obtained clear solution 125 ml) is lyophilized. The resulting solid consists of pure desulphatohirudin.

EXAMPLE 32

Construction of Plasmid pJDB207/PHO5-EGL

The nucleotide sequence coding for eglin C, a polypeptide of 70 aminoacids from leech has been synthesized in vitro, subcloned and expressed in *E. coli* as described in European Patent Application No. 146,785. The exact in frame fusion of the eglin coding sequence to the sequence coding for the PHO5 signal peptide is achieved in a completely analogous way as described for hirudin in Examples 15 and 16. A single clone with the correct orientation of the insert in the vector is referred to as pJDB207/PHO5-EGL. *Saccharomyces cerevisiae* strain GRF18 is transformed as usual. Transformants are selected and cultuted as described in Example 29. No eglin C is detectable in the culture broth.

What is claimed is:

1. A method for the production of desulphatohirudin compounds with hirudin activity comprising the steps of:
   (a) culturing under appropriate nutrent conditions yeast cells transformed with a hybrid vector, the hybrid vector comprising:
      one to four DNA inserts each comprising a yeast promoter selected from the group consisting of a PHO5 promoter, a GAPDH promoter, or a functional fragment thereof, and a hybrid promoter comprising upstream activation sequences of the PHO5 gene and downstream promoter elements including a functional TATA box of the GAPDH gene,
      a DNA segment consisting of a first DNA sequence encoding the PHO5 or invertase signal peptide upstream of and in reading frame with a second DNA sequence coding for mature desulphatohirudin wherein the DNA segment is under transcriptional control of the yeast promoter, and a DNA sequence containing eukaryotic transcription termination signals,
      and a selective gene marker,
   wherein about 90 percent or more of the desulphatohirudin compounds are secreted into the culture medium as measured by high pressure liquid chromatography, and
   (b) isolating the proteins with hirudin activity from the culture medium.

2. Method according to claim 1 characterized in that there is used yeast transformed with a hybrid vector having one to four DNA inserts each comprising the PHO5 promoter, a DNA segment consisting of the PHO5 signal sequence upstream of and in reading frame with a DNA sequence coding for mature desulphatohirudin, which DNA segment is under transcriptional control of the PHO5 promoter, and the 3' flanking sequence of the PHO5 gene.

3. Method according to claim 1 characterized in that there is used yeast transformed with a hybrid vector having one to four DNA inserts each comprising the GAPDH promoter, a DNA segment consisting of the PHO5 signal sequence upstream of and in reading frame with a DNA sequence coding for mature desulphatohirudin, which DNA segment is under transcriptional control of the GAPDH promoter, and the 3' flanking sequence of the PHO5 gene.

4. Method according to claim 1 characterized in that there is used yeast transformed with a hybrid vector having one to four DNA inserts each comprising a hybrid promoter comprising upstream activation site(s) of the yeast PHO5 gene and a downstream promoter element including the TATA box of the yeast GAPDH gene, a DNA segment consisting of the PHO5 signal sequence upstream of and in reading frame with a DNA sequence coding for mature desuphatohirudin, which DNA segments is under transcriptional control of the hybrid promoter, and 3' flanking sequence of the PHO5 gene.

5. Method according to claim 1 characterized in that there is used yeast transformed with a hybrid vector having one to four DNA inserts each comprising the PHO5 promoter, a DNA segment consisting of the invertase signal sequence upstream of and in reading frame with a DNA sequence coding for mature desulphatohirudin, which DNA segment is under transcriptional control of the PHO5 promoter, and the 3' flanking sequence of the PHO5 gene.

6. Method according to claim 1 for the production of Des-(Leu$^{64}$,Gln$^{65}$)-desulphatohirudin variant HV1 having the formula Val Val Tyr Thr Asp Cys Thr Glu Ser Gly Gln Asn Leu Cys Leu Cys Glu Gly Ser Asn Val Cys Gly Gln Gly Asn Lys Cys Ile Leu Gly Ser Asp Gly Glu Lys Asn Gln Cys Val Thr Gly Glu Gly Thr Pro Lys Pro Gln Ser His Asn Asp Gly Asp Phe Glu Glu Ile Pro Glu Glu Tyr.

7. Method according to claim 1 for the production of Des-(Gln$^{65}$)-desulphatohirudin variant HV1 having the formula Val Val Tyr Thr Asp Cys Thr Glu Ser Gly Gin Asn Leu Cys Leu Cys Glu Gly Ser Asn Val Cys Gly Gln Gly Asn Lys Cys Ile Leu Gly Ser Asp Gly Glu Lys Asn Gln Cys Val Thr Gly Glu Gly Thr Pro Lys Pro Gln Ser His Asn Asp Gly Asp Phe Glu Glu Ile Pro Glu Glu Tyr Leu.

8. Method according to claim 1 for the production of desulphatohirudin variant HV1 having the formula Val Val Tyr Tyr Asp Cys Thr Glu Ser Gly Gln Asn Leu Cys Leu Cys Glu Gly Ser Asn Val Cys Gly Gln Gly Asn Lys Cys Ile Leu Gly Ser Asp Gly Glu Lys Asn Gln Cys Val Thr Gly Glu Gly Thr Pro Lys Pro Gln Ser His Asn Asp Gly Asp Phe Glu Glu Ile Pro Glu Glu Tyr Leu Gln.

9. Method according to claim 1 for the production of desulphatohirudin variant HV2 having the formula Ile Thr Tyr Thr Asp Cys Thr Glu Ser Gly Gln Asn Leu Cys Leu Cys Glu Gly Ser Asn Val Cys Gly Lys Gly Asn Lys Cys Ile Leu Gly Ser Asn Gly Lys Gly Asn Gln Cys Val Thr Gly Glu Gly Thr Pro Asn Pro Glu Ser His Asn Asn Gly Asp Phe Glu Glu Ile Pro Glu Glu Tyr Leu Gln.

10. Method according to claim 1 for the production of desulphatohirudin variant PA having the formula Ile Thr Tyr Thr Asp Cys Thr Glu Ser Gly Gln Asn Leu Cys Leu Cys Glu Gly Ser Asn Val Cys Gly Lys Gly Asn Lys Cys Ile Leu Gly Ser Gln Gly Lys Asp Asn Gln Cys Val Thr Gly Glu Gly Thr Pro Lys Pro Gln Ser His Asn Gln Gly Asp Phe Glu Pro Ile Pro Glu Asp Ala Tyr Asp Glu.

11. Method according to claim 1 for the production of des-(Val)$_2$-desulphatohirudin.

12. A method according to claim 1 wherein the functional fragments are selected from the group consisting of GAPDH-EL and GAPDH-FL.

13. A yeast hybrid vector comprising one to four DNA inserts each comprising a yeast promoter selected from the group consisting of a PHO5 promoter, a GAPDH promoter, or a functional fragment thereof, and a hybrid promoter comprising upstream activation sequences of the PHO5 gene and downstream promoter elements including a functional TATA box of the GAPDH gene, a DNA segment consisting of a first DNA sequence encoding the PHO5 or invertase signal peptide upstream of and in reading frame with a second DNA sequence coding for mature desulphatohirudin which DNA segment is under transcriptional control of the yeast promoter, and a DNA sequence containing eukaryotic transcription termination signals, and a selective gene marker;

wherein the yeast hybrid vector, when inserted into yeast cells, is capable of causing a culture of the yeast cells grown in a culture medium to produce desulphatohirudin compounds having hirudin activity and wherein about 90 percent or more of the desulphatohirudin compounds are secreted into the culture medium by the yeast cells, as measured by high performance liquid chromatography.

14. A yeast cell transformed with a hybrid vector comprising one to four DNA inserts each comprising a yeast promoter selected from the group consisting of a PHO5 promoter, a GAPDH promoter, or a functional fragment thereof, and a hybrid promoter comprising upstream activation sequences of the PHO5 gene and downstream promoter elements. including a functional TATA box of the GAPDH gene, a DNA segment consisting of a first DNA sequence encoding the PHO5 or invertase signal peptide upstream of and in reading frame with a second DNA sequence coding for mature desulphatohirudin which DNA segment is under transcriptional control of the yeast promoter, and a DNA sequence containing eukaryotic transcription termination signals, and a DNA sequence containing eukaryatic transcription termination signals, and a selective gene marker, which yeast cell is capable of producing desulphatohirudin compounds having hirudin activity and secretes about 90 percent or more of the desulphatohirudin compounds, as measured by high pressure liquid chromatography, and mutants thereof.

* * * * *

UNITED STATES PATENT AND TRADEMARK OFFICE
CERTIFICATE OF CORRECTION

PATENT NO.    : 6,410,272 B1
DATED         : June 25, 2002
INVENTOR(S)   : Meyhack et al.

It is certified that error appears in the above-identified patent and that said Letters Patent is hereby corrected as shown below:

<u>Column 59,</u>
Line 46, should read:
-- (a) culturing under appropriate nutrient conditions yeast --.

<u>Column 60,</u>
Lines 27 and 28, should read: -- desulphatohirudin, which DNA segment is under transcriptional control of the hybrid promoter, and the 3' flanking --.
Line 49, should read: -- Val Val Tyr Thr Asp Cys Thr Glu Ser Gly Gln Asn Leu --.
Line 56, should read: -- Val Val Tyr Thr Asp Cys Thr Glu Ser Gly Gln Asn Leu Cys --.

Signed and Sealed this

Seventh Day of January, 2003

JAMES E. ROGAN
*Director of the United States Patent and Trademark Office*

UNITED STATES PATENT AND TRADEMARK OFFICE
CERTIFICATE OF CORRECTION

PATENT NO.    : 6,410,272 B1
DATED         : June 25, 2002
INVENTOR(S)   : Meyhack et al.

It is certified that error appears in the above-identified patent and that said Letters Patent is hereby corrected as shown below:

<u>Title page,</u>
Item [73], should read:

-- [73] Assignee: UCP Gen-Pharma AG, Kirchberg, Switzerland and
Novartis AG, Basel, Switzerland --

Signed and Sealed this

Ninth Day of December, 2003

JAMES E. ROGAN
*Director of the United States Patent and Trademark Office*